(12) United States Patent
Tsien et al.

(10) Patent No.: US 9,695,251 B2
(45) Date of Patent: *Jul. 4, 2017

(54) ACTIVATABLE CELL PENETRATING PEPTIDES WITH QUENCHED FLUOROPHORES

(75) Inventors: Roger Y. Tsien, La Jolla, CA (US); Tao Jiang, San Diego, CA (US); Elamprakash N. Savariar, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 423 days.

This patent is subject to a terminal disclaimer.

(21) Appl. No.: 13/566,913

(22) Filed: Aug. 3, 2012

(65) Prior Publication Data
US 2013/0078188 A1    Mar. 28, 2013

Related U.S. Application Data

(63) Continuation-in-part of application No. 11/437,095, filed on May 19, 2006, now abandoned, which is a continuation-in-part of application No. 11/133,804, filed on May 19, 2005, now Pat. No. 7,985,401, which is a continuation-in-part of application No. 10/699,562, filed on Oct. 31, 2003, now Pat. No. 7,431,915, application No. 13/566,913, which is a continuation-in-part of application No. 13/384,591, filed as application No. PCT/US2010/042184 on Jul. 15, 2010, application No. 13/566,913, which is a continuation-in-part of application No. 13/384,581, filed on Feb. 16, 2012, which is a continuation-in-part of application No. 13/314,134, filed on Dec. 7, 2011, now Pat. No. 8,642,561, which is a continuation-in-part of application No. 12/244,602, filed on Oct. 2, 2008, now Pat. No. 8,110,554, application No. 13/566,913, which is a continuation-in-part of application No. 13/155,168, filed on Jun. 7, 2011, now Pat. No. 9,072,792.

(60) Provisional application No. 61/225,872, filed on Jul. 15, 2009, provisional application No. 61/514,806, filed on Aug. 3, 2011.

(51) Int. Cl.
| | |
|---|---|
| *A61K 51/00* | (2006.01) |
| *A61M 36/14* | (2006.01) |
| *C07K 19/00* | (2006.01) |
| *A61K 49/00* | (2006.01) |
| *A61K 41/00* | (2006.01) |
| *A61K 47/48* | (2006.01) |
| *A61K 49/08* | (2006.01) |
| *A61K 49/14* | (2006.01) |
| *A61K 51/08* | (2006.01) |
| *C07K 14/47* | (2006.01) |

(52) U.S. Cl.
CPC .......... *C07K 19/00* (2013.01); *A61K 41/0095* (2013.01); *A61K 47/48246* (2013.01); *A61K 47/48315* (2013.01); *A61K 47/48338* (2013.01); *A61K 49/00* (2013.01); *A61K 49/0032* (2013.01); *A61K 49/0043* (2013.01); *A61K 49/0056* (2013.01); *A61K 49/085* (2013.01); *A61K 49/14* (2013.01); *A61K 49/146* (2013.01); *A61K 51/088* (2013.01); *C07K 14/4728* (2013.01)

(58) Field of Classification Search
CPC ............... A61K 49/00; A61K 49/0032; A61K 49/0043; A61K 49/0056; A61K 49/085; A61K 49/14; A61K 49/146; A61K 51/00; A61K 51/08; A61K 51/088; A61K 41/00; A61K 41/0095; A61K 47/00; A61K 47/48246; A61K 47/48315; A61K 47/48338; C07K 14/4728; C07K 19/00; G01N 33/18; G01N 33/1826
USPC .... 424/1.11, 1.65, 1.69, 9.1, 9.6; 514/1, 1.1, 514/19.2, 19.3, 19.4, 19.5, 19.6, 21.1, 514/21.8, 21.9; 530/300, 316, 317, 329, 530/331
See application file for complete search history.

(56) References Cited

U.S. PATENT DOCUMENTS

| | | |
|---|---|---|
| 4,466,919 A | 8/1984 | Weingarten |
| 4,507,389 A | 3/1985 | Weingarten |
| 5,434,073 A | 7/1995 | Dawson et al. |
| 5,674,980 A | 10/1997 | Frankel et al. |

(Continued)

FOREIGN PATENT DOCUMENTS

| | | |
|---|---|---|
| WO | WO 01/75087 A2 | 10/2001 |
| WO | 2005/0042034 A1 | 5/2005 |
| WO | WO 2005/042034 A1 | 5/2005 |

OTHER PUBLICATIONS

Aguilera, T.A. et al., "Systemic in vivo distribution of activatable cell penetrating peptides is superior to cell penetrating peptides," *Integr Biol (Camb)*, Jun. 2009, vol. 1, No. 5-6, pp. 371-381.

(Continued)

*Primary Examiner* — D L Jones
(74) *Attorney, Agent, or Firm* — Morgan, Lewis & Bockius LLP

(57) ABSTRACT

The invention provides compositions useful as molecular probes. In particular, the invention provides activatable cell penetrating peptides comprising a fluorescence donor and a fluorescence acceptor. Exemplary fluorescence donors and fluorescence acceptors include compounds derived from cyanine. Also provided are ratiometric, multispectral, and excitation lifetime imaging methods for detecting the molecular probes provided herein.

29 Claims, 35 Drawing Sheets
(28 of 35 Drawing Sheet(s) Filed in Color)

(56) References Cited

U.S. PATENT DOCUMENTS

| | | | |
|---|---|---|---|
| 5,747,641 | A | 5/1998 | Frankel et al. |
| 5,910,300 | A | 6/1999 | Tournier et al. |
| 6,083,486 | A | 7/2000 | Weissleder et al. |
| 6,348,185 | B1 | 2/2002 | Piwnica-Worms |
| 6,592,847 | B1 | 7/2003 | Weissleder et al. |
| 7,431,915 | B2 | 10/2008 | Jiang et al. |
| 7,985,401 | B2 * | 7/2011 | Jiang et al. ............ 424/1.69 |
| 8,110,554 | B2 * | 2/2012 | Jiang et al. ............ 514/21.6 |
| 8,486,373 | B2 | 7/2013 | Weissleder et al. |
| 8,642,561 | B2 * | 2/2014 | Jiang et al. ............ 514/21.6 |
| 2001/0021763 | A1 | 9/2001 | Harris |
| 2002/0009786 | A1 | 1/2002 | Tang et al. |
| 2003/0176335 | A1 | 9/2003 | Zhang et al. |
| 2004/0009122 | A1 | 1/2004 | Klaveness et al. |
| 2004/0241096 | A1 | 12/2004 | Bogdanov et al. |
| 2005/0107583 | A1 | 5/2005 | Jiang et al. |
| 2006/0041105 | A1 | 2/2006 | Jiang et al. |
| 2007/0041904 | A1 | 2/2007 | Jiang et al. |
| 2009/0004118 | A1 | 1/2009 | Nie et al. |
| 2012/0014873 | A1 | 1/2012 | Jiang et al. |
| 2012/0134922 | A1 | 5/2012 | Tsien et al. |
| 2013/0020537 | A1 | 1/2013 | Maruno et al. |
| 2013/0176335 | A1 | 7/2013 | Sugiyama et al. |
| 2015/0031852 | A1 | 1/2015 | Liu et al. |

OTHER PUBLICATIONS

Bartles, J.R. et al., "Identification and characterization of espin, an actin-binding protein localized to the F-actin-rich junctional plaques of Sertoli cell ectoplasmic specializations," *Journal of Cell Science*, 1996, vol. 109, No. 6, pp. 1229-1239.

Bhorade, R. et al., "Macrocyclic Chelators with Paramagnetic Cations are Internalized into Mammalian Cells via a HIV-Tat Derived Membrane Translocation Peptide," *Bioconjugate Chemistry*, May 1, 2000, vol. 11, No. 3, pp. 301-305.

Bremer, C. et al., "In vivo molecular target assessment of matrix metalloproteinase inhibition," *Nature Medicine*, Jun. 2001, vol. 7, No. 6, pp. 743-748.

Bremer, C. et al., "Optical Imaging of Matrix Metalloproteinase-2 Activity in Tumors: Feasibility Study in a Mouse Model." *Radiology*, 2001, vol. 221, pp. 523-529.

Chen, B. et al., "Thrombin Activity Associated with Neuronal Damage during Acute Focal Ischemia," *The Journal of Neuroscience*, May 30, 2012, vol. 32, No. 22, pp. 7622-7631.

Chen, J. et al., "Zipper' Molecular Beacons: A Generalized Strategy to Optimize the Performance of Activatable Proteases Probes," *Bioconjugate Chemistry*, 2009, vol. 20, pp. 1836-1842.

Gallwitz, M. et al., "The Extended Cleavage Specificity of Human Thrombin," *PLoS ONE*, Feb. 2012, vol. 12, No. 2, e.31756, pp. 1-16.

Golub, T.R. et al., "Molecular Classification of Cancer: Class Discovery and Class Prediction by Gene Expression Monitoring," *Science*, Oct. 15, 1999, vol. 286, pp. 531-537.

Hutteman, M. et al., "Optimization of Near-Infrared Fluorescent Sentinel Lymph Node Mapping for Vulvar Cancer," *Am J Obstet Gynecol.*, Jan. 2012, vol. 206, No. 1, pp. 89.e1-89.e5.

Jaffer, F.A. et al., "In Vivo Imaging of Thrombin Activity in Experimental Thrombi With Thrombin-Sensitive Near-Infrared Molecular Probe," *Arteriosclerosis, Thrombosis, and Vascular Biology*, Nov. 2002, vol. 22, pp. 1929-1935.

Jiang, T. et al., "Tumor imaging by means of proteolytic activation of cell-penetrating peptides," *PNAS*, Dec. 21, 2004, pp. 17867-17872, vol. 101, No. 51.

Levenson, R. et al., "Review Article: Modern Trends in Imaging X: Spectral imaging in preclinical research and clinical pathology," *Anal Cell Pathol*, 2012, vol. 35, pp. 339-361.

Levi, J. et al., "Design, Synthesis and Imaging of an Activatable Photoacoustic Probe," *J Am Chem Soc.*, Aug. 18, 2010, vol. 132, No. 32, pp. 11264-11269.

Linder, K.E. et al., "Synthesis, In Vitro Evaluation, and In Vivo Metabolsim of Fluor/Quencher Compounds Containing IRDye 800CW and Black Hole Quencher-3 (BHQ-3)," *Bioconjugate Chemistry*, 2011, vol. 22, pp. 1287-1297.

Nguyen, Q.T. et al., "Surgery with molecular fluorescence imaging using activatable cell-penetrating peptides decreases residual cancer and improves survival," *PNAS*, Mar. 2, 2010, vol. 107, No. 9, pp. 4317-4322.

Olson, E.S. et al., "Activatable cell penetrating peptides linked to nanoparticles as dual probes for in vivo fluorescence and MR imaging of proteases," *PNAS*, Mar. 2, 2010, vol. 107, No. 9, pp. 4311-436.

Olson, E.S. et al., "In vivo characterization of activatable cell penetrating peptides for targeting protease activity in cancer," *Integr Biol (Camb)*, Jun. 2009, vol. 1, No. 5-6, pp. 382-393.

Olson, E.S. et al., "In vivo fluorescence imaging of atherosclerotic plaques with activatable cell-penetrating peptides thrombin activity," *Integr Biol*, 2012, vol. 4, pp. 595-605.

Rothbard, J. B. et al., "Conjugation of arginine oligomers to cyclosporin A facilitates topical delivery and inhibition of inflammation," *Nature Medicine*, Nov. 2000, vol. 6, No. 11, pp. 1253-1257.

Rothbard, J.B. et al., "Arginine-Rich Molecular Transporters for Drug Delivery: Role of Backbone Spacing in Cellular Uptake," *J. Med. Chem.*, 2002, vol. 45, pp. 3612-3618.

Ryppa, C. et al., "In Vitro and in vivo Evaluation of Doxorubicin Conjugates with the Divalent Peptide E-[c(RGDfK)$_2$]that Targets Integrin $\alpha v \beta_3$," *Bioconjugate Chemistry*, 2008, vol. 19, pp. 1414-1422.

Stary, H.C. et al., "A Definition of Advanced Types of Atherosclerotic Lesions and a Histological Classification of Atherosclerosis: A Report From the Committee on Vascular Lesions of the Council on Atheriosclerosis, American Heart Association," *Circulation*, 1995, vol. 92, pp. 1355-1374.

Stone, G.W. et al., "A Prospective Natural-History Study of Coronary Atherosclerosis," *The New England Journal of Medicine*, Jan. 20, 2011, vol. 364, No. 3, pp. 226-235.

Tseng, W.W. et al., "Development of an Orthotopic Model of Invasive Pancreatic Cancer in an Immunocompetent Murine Host," *Clinical Cancer Research*, Jul. 15, 2010, vol. 16, No. 14, pp. 3684-3695.

Tsien, R.Y. et al., "Practical design criteria for a dynamic ration imaging system," *Cell Calcium*, 1990, vol. 11, pp. 93-109.

Tsien, R.Y., "Indicators Based on Fluorescence Resonance Energy Transfer," Chapter 74 in *Imaging in Neuroscience and Development*, Cold Spring Harbor Laboratory Press, Cold Spring Harbor, 2005, pp. 549-556.

Tung, C.H. et al., "A Novel Near-Infrared Fluorescence Sensor for Detection of Thrombin Activation in Blood," *Chembiochem*, 2002, vol. 3, pp. 207-211.

Tung, C-H. et al., "Arginine containing peptides as delivery vectors," *Advanced Drug Delivery Reviews*, 2003, vol. 55, pp. 281-294.

Ullrich, K.J. et al., "Controluminal para-aminohippurate (PAH) transport in the proximal tubule of the rat kidney," *Pflügers Arch.*, 1989, vol. 415, pp. 342-350.

Van Berkel, S.S. et al., "Fluorogenic Peptide-Based Substrates for Monitoring Thrombin Activity," *ChemMedChem*, 2012, vol. 7, pp. 606-617.

Van Dam, G.M. et al., "Intraoperative tumor-specific fluorescence imaging in ovarian cancer by folate receptor-$\alpha$ targeting: first in-human results," *Nature Medicine*, 2011, vol. 17, pp. 1315-1319.

Van Duijnhoven, S.M.J. et al., "Tumor Targeting of MMP-2/9 Activatable Cell-Penetrating Imaging Probes is Caused by Tumor-Independent Activation," *J Nucl Med.* 2011, vol. 52, pp. 279-286.

Vartak, D.G. et al., "In vitro evaluation of functional interaction of integrin $\alpha v \beta 3$ and matrix metalloprotease-2," *Mol. Pharmaceutics*, 2009, vol. 6, No. 6, pp. 1856-1867.

Wang, Y. et al., "Visualizing the mechanical activation of Src," *Nature*, Apr. 21, 2005, pp. 1040-1045, vol. 434.

Wender, P.A. et al., "The design, synthesis, and evaluation of molecules that enable or enhance cellular uptake: Peptoid molcular transporters," *PNAS*, Nov. 21, 2000, vol. 97, No. 24, pp. 13003-13008.

(56) References Cited

OTHER PUBLICATIONS

Whitney, M. et al., "Parallel in Vivo and in Vitro Selection Using Phage Display Indentifies Protease-dependent Tumor-targeting Peptides," *The Journal of Biological Chemistry*, Jul. 16, 2010, vol. 285, No. 29, pp. 22532-22541.
Zhu, L. et al., "Dual-Functional, Receptor-Targeted Fluorogenic Probe for In Vivo Imaging of Extracellular Protease Expressions," *Bioconjugate Chemistry*, Jun. 15, 2011, vol. 22, No. 6, pp. 1001-1005.
Proimmune, "think peptides® the source for all peptides for your research," 2012, pp. 1-15.
Arnold, D. et al., "Substrate specificity of cathepsins D and E determined by N-terminal and C-terminal sequencing of peptide pools," Eur. J. Biochem., 1997, vol. 249, pp. 171-179.
Scherer, R.L. et al., "Optical imaging of matrix metalloproteinase-7 activity *in vivo* using a proteolytic nanobeacon," *Mol Imaging*, 2008, vol. 7, No. 3, pp. 118-131.
Van Vlerken, L.E. et al., "Poly(ethylene glycol)-modified Nanocarriers for Tumor-targeted and Intracellular Delivery," *Pharmaceutical Research*, Aug. 2007, vol. 24, No. 8, pp. 1404-1414.

* cited by examiner

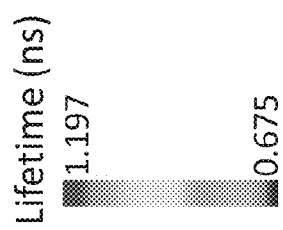
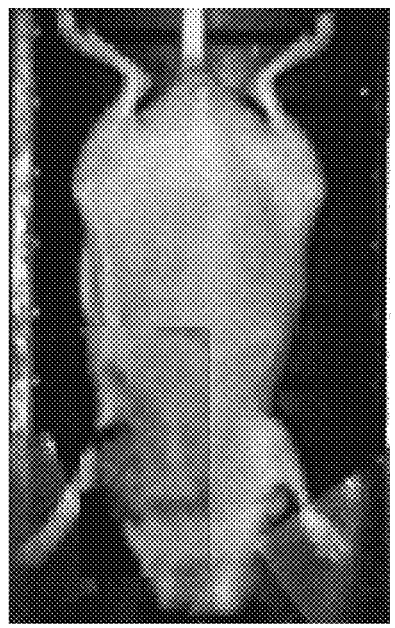
*FIG. 5B*
*FIG. 5D*
*FIG. 5A*
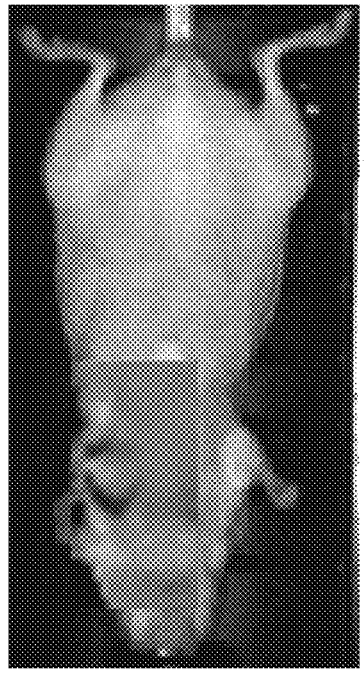
*FIG. 5C*

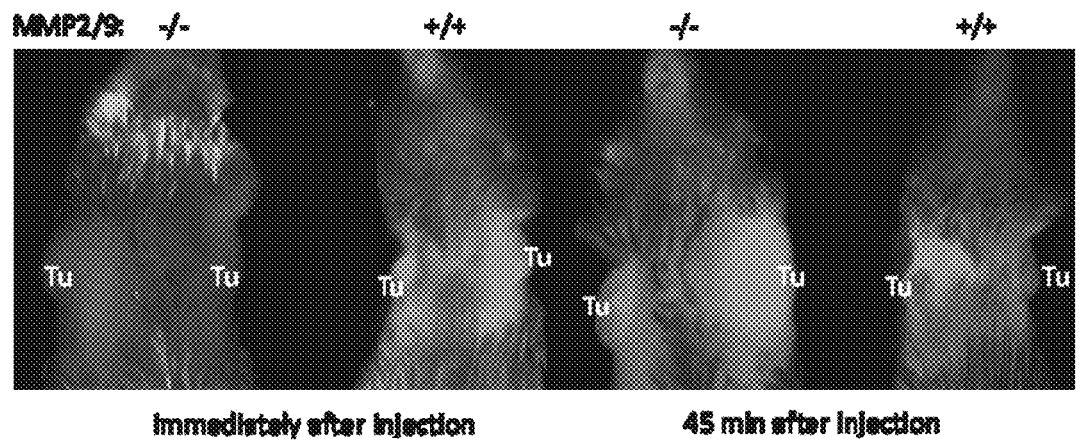
FIG. 8
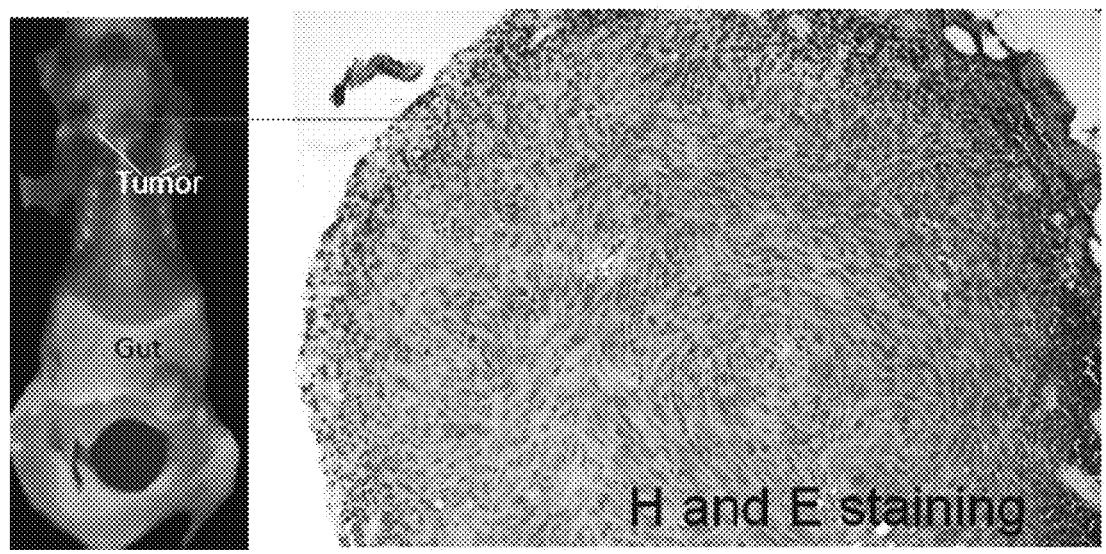
FIG. 9A
FIG. 9B

Scheme 3 - Synthesis of RACPP2

Scheme 4 - Synthesis of RACPP3

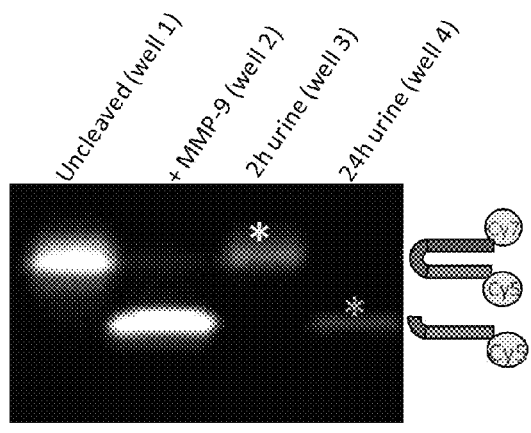 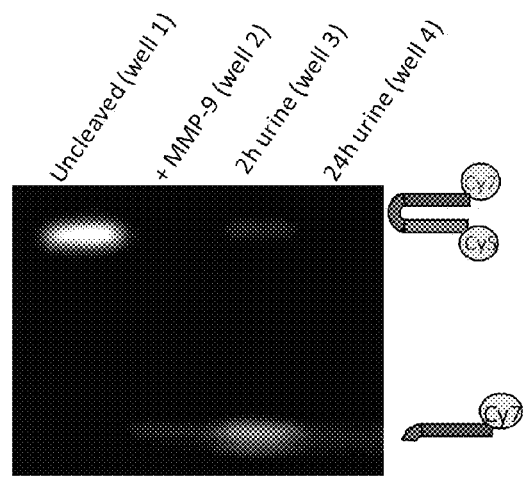
*FIG. 15A*  *FIG. 15B*
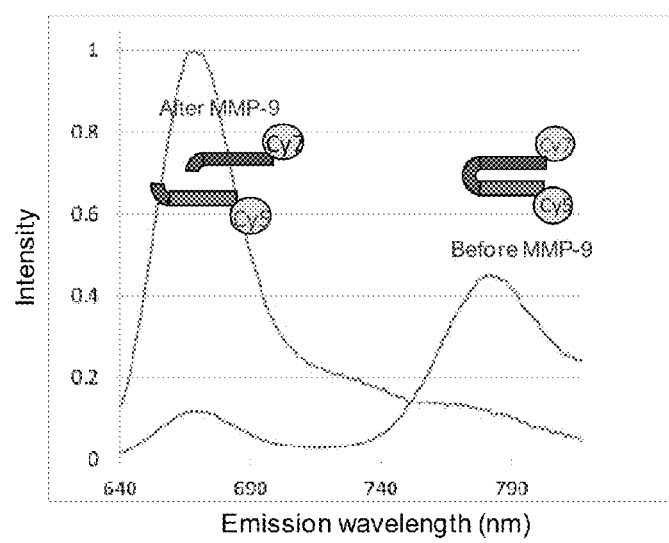
*FIG. 15C*

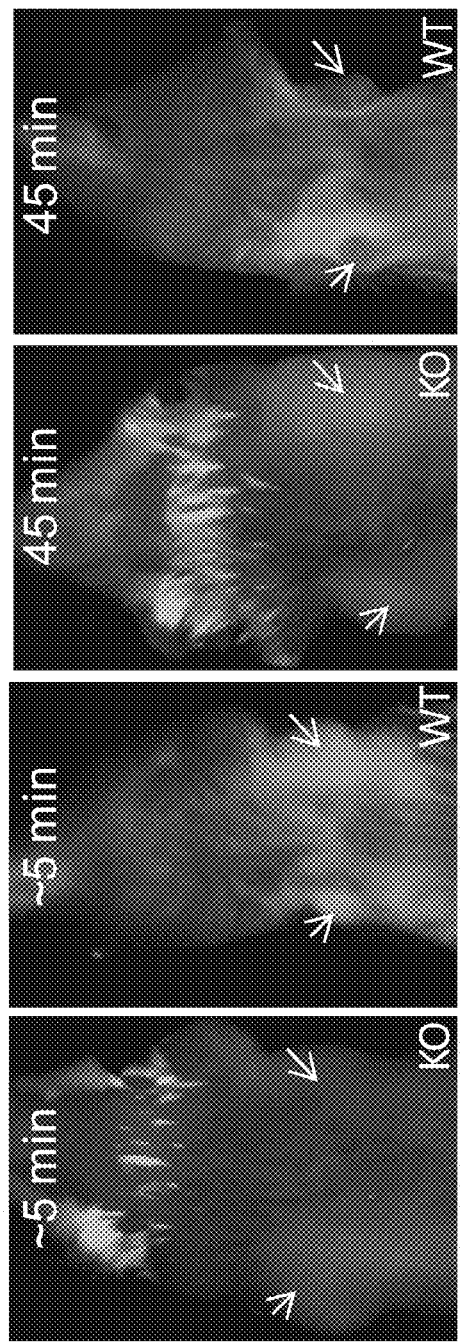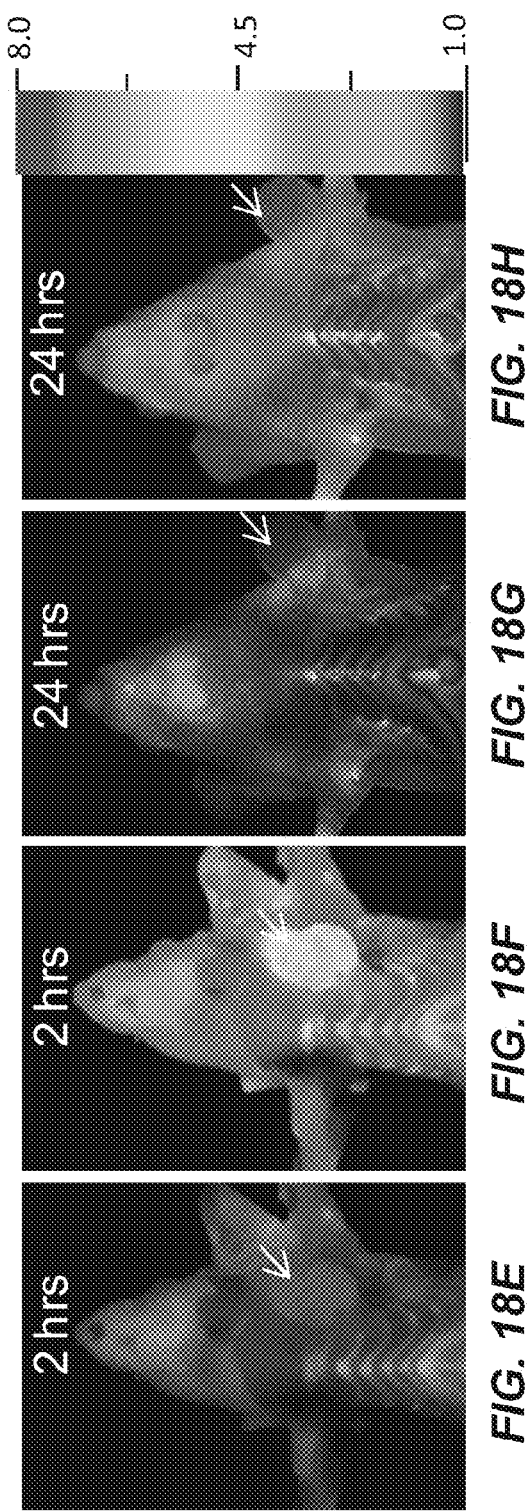

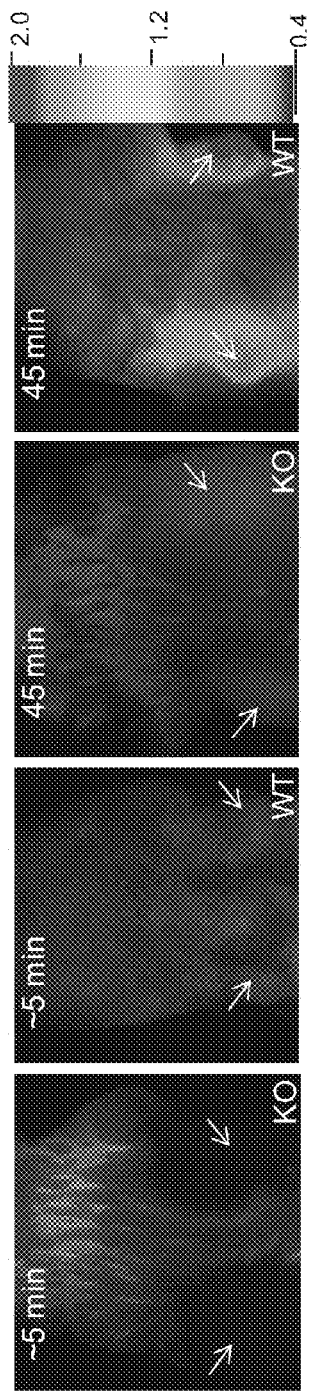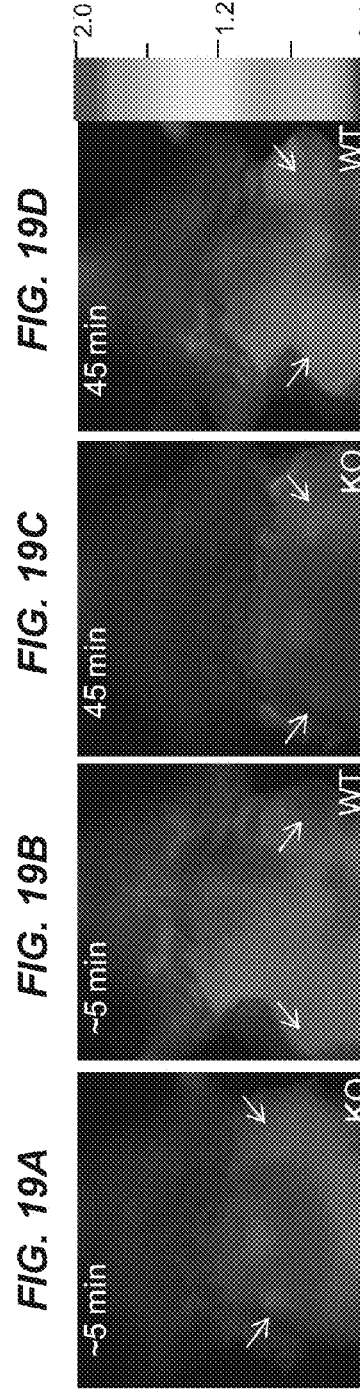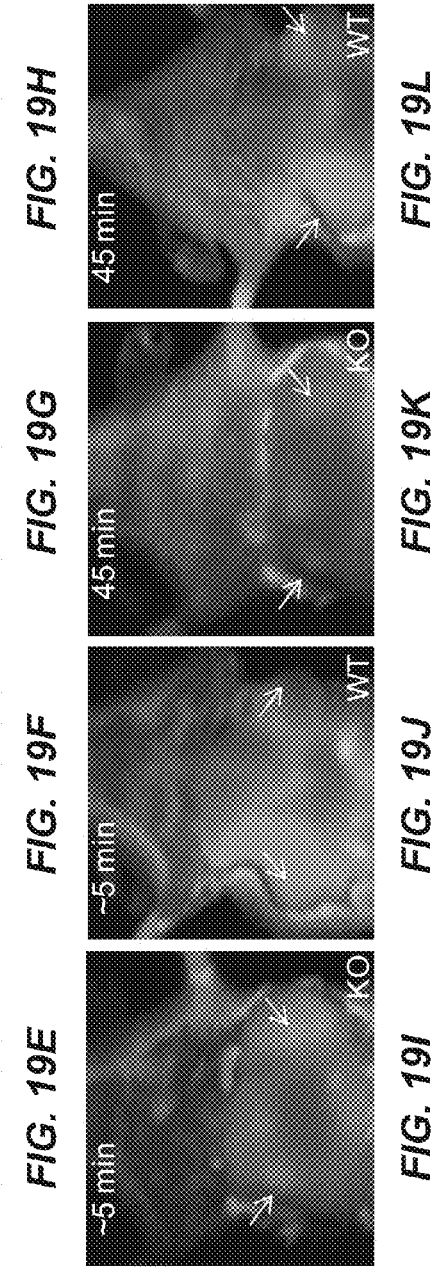

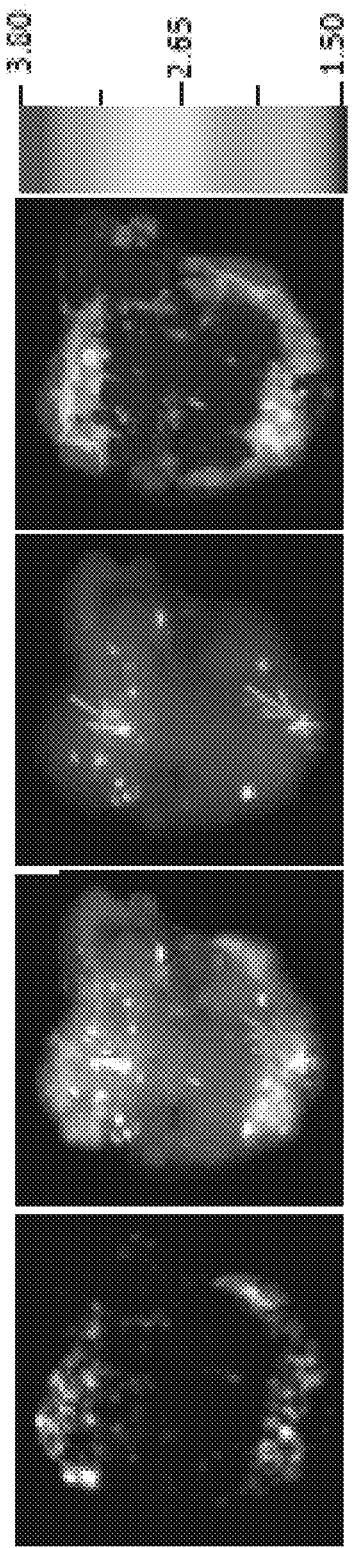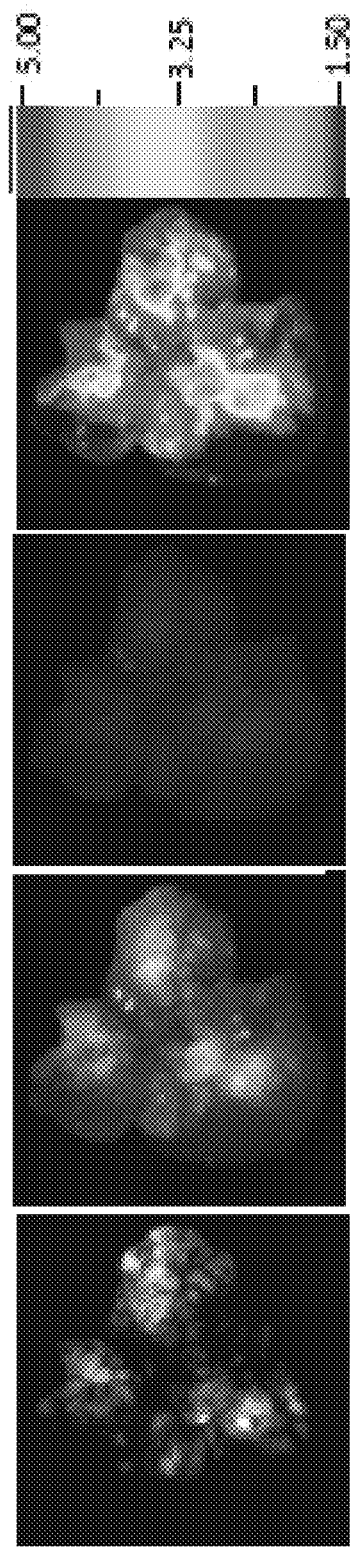
FIG. 21A  FIG. 21B  FIG. 21C  FIG. 21D
FIG. 21E  FIG. 21F  FIG. 21G  FIG. 21H Solid phase peptide synthesis and HPLC purification $NH_2$-e9-c(S-StBu)-(Substrate)-r9-c-$CONH_2$ (1, 6, 11, 16)
Cy5-Mal, NMM, DMSO $NH_2$-e9-c(S-StBu)-(Substrate)-r9-c(Cy5)-$CONH_2$ (2, 7, 12, 17)
$Et_3P$ $NH_2$-e9-c(SH)-(Substrate)-r9-c(Cy5)-$CONH_2$ (3, 8, 13, 18)
Mal-Peg12, NMM, DMSO $NH_2$-e9-c(S-Peg12)-(Substrate)-r9-c(Cy5)-$CONH_2$ (4, 9, 14, 19)
Cy7-NHS, NMM, DMSO Cy7-NH-e9-c(S-Peg12)-(Substrate)-r9-c(Cy5)-$CONH_2$ (RACPPs 5, 10, 15, 20)

1-5, Substrate = oDPRSFL
6-10, Substrate = oPPRSFL
11-15, Substrate = peg6
16-20, Substrate = oPLGC(Me)AG.

FIG. 26

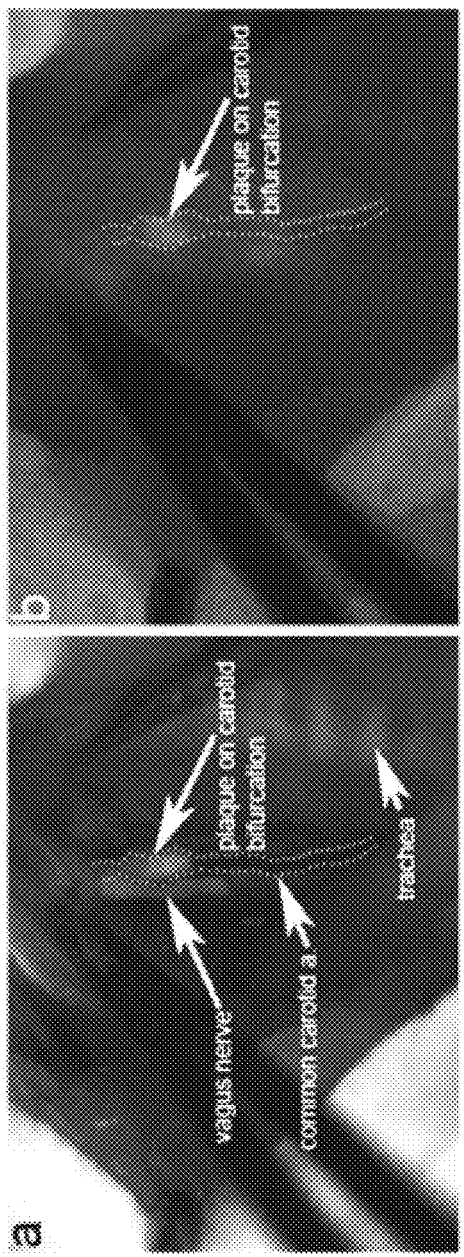
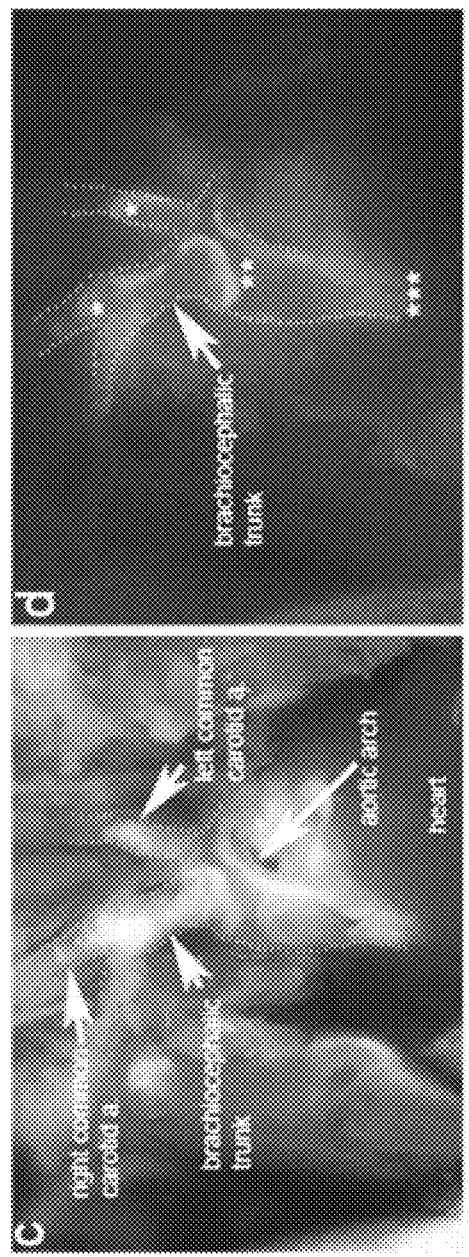
FIG. 33A  FIG. 33B  FIG. 33C  FIG. 33D

ACTIVATABLE CELL PENETRATING PEPTIDES WITH QUENCHED FLUOROPHORES

CROSS-REFERENCE TO RELATED APPLICATION

The present application is a continuation-in-part of U.S. patent application Ser. No. 11/437,095, filed May 19, 2006, which is a continuation in part of U.S. patent application Ser. No. 11/133,804, filed May 19, 2005 and issued as U.S. Pat. No. 7,985,401, which is a continuation-in-part of U.S. patent application Ser. No. 10/699,562, filed Oct. 31, 2003 and issued as U.S. Pat. No. 7,431,915, the disclosures of which are hereby expressly incorporated by reference in their entireties for all purposes. The present application is also a continuation-in-part of U.S. patent application Ser. No. 13/384,591, filed Jul. 5, 2010 Feb. 16, 2012, which is a U.S. National Phase of International Patent Application No. PCT/US2010/042184, filed Jul. 15, 2010, which claims the benefit of U.S. Provisional Application Ser. No. 61/225,872, filed Jul. 15, 2009, the contents of which are hereby expressly incorporated by reference in their entireties for all purposes. The present application is also a continuation-in-part of U.S. patent application Ser. No. 13/384,581, filed Jul. 15, 2010, which claims the benefit of U.S. Provisional Application Ser. No. 61/225,872, filed Jul. 15, 2009, the contents of which are hereby expressly incorporated by reference in their entireties for all purposes. The present application also claims the benefit of U.S. Provisional Application Ser. No. 61/514,806, filed Aug. 3, 2011, the content of which is hereby expressly incorporated herein by reference in its entirety for all purposes. The present application is also a continuation-in-part of U.S. patent application Ser. No. 13/314,134, filed Dec. 7, 2011, which is a continuation of U.S. patent application Ser. No. 12/244,602, filed Oct. 2, 2008 and issued as U.S. Pat. No. 8,110,554. The present application is also a continuation-in-part of U.S. patent application Ser. No. 13/155,168, filed on Jun. 7, 2011.

STATEMENT OF GOVERNMENT SUPPORT

This work was supported by a grant from the US Army (W81XWH-09-1-0699) and the National Institute of Health (CA128346). The Government has certain rights in this invention.

BACKGROUND OF THE INVENTION

Cancer staging depends both on evaluation of both the primary tumor and metastatic disease. In the management of many cancers such as prostate or head and neck squamous cell carcinoma (HNSCC), the extent of lymph node metastasis can often only be fully evaluated after the patient has undergone surgical removal of all anatomically susceptible lymph nodes for pathological examination. Therefore, development of molecularly targeted imaging for more accurate detection of metastatic nodes during initial disease staging and surgery would be one of the most effective means to improve accuracy in staging and minimize morbidity associated with unnecessary lymph node dissections.

Matrix metalloproteinases (MMPs) play crucial roles in cancer invasion and metastasis (Bauvois, B., *Biochim Biophys Acta* 1825, 29-36 (2012)). While other MMPs are also of interest, MMP-2 and -9 are currently the species with the best-established associations with tumor grade/poor prognosis and with relatively specific substrate sequences. Although MMP-2,-9 are also increased in inflammation/wound healing, absolute levels of these gelatinases in the head and neck have been used to differentiate between benign papillomas versus carcinoma of the larynx (Uloza, V. et al., *Eur Arch Otorhinolaryngol* 268, 871-878 (2011)). Increased MMP-2,-9 expression has been shown to correlate with cancer grade (Wittekindt, C. et al., *Acta Otolaryngol* 131, 101-106 (2011), the content of which is hereby expressly incorporated by reference in its entirety for all purposes) and decreased survival (Liu, W. W. et al., *Otolaryngol Head Neck Surg* 132, 395-400 (2005); Mallis, A. et al., *Eur Arch Otorhinolaryngol* 269, 639-642 (2012), the contents of which are hereby expressly incorporated by reference in their entireties for all purposes). In carcinoma of the tongue, increased MMP-2,-9 expression has been shown to correlate with incidence of lymph node metastases (Zhou, C. X. et al., *Aust Dent J* 55, 385-389 (2010), the content of which is hereby expressly incorporated by reference in its entirety for all purposes). We have previously described Activatable Cell Penetrating Peptides (ACPPs), which rely on tumor-associated MMP-2,-9 to unmask the adhesiveness of Cell Penetrating Peptides (CPPs) (Olson, E. S. et al., *Integrative Biology* 1, 382-393 (2009); Aguilera, T. A. et al., *Integrative Biology* 1, 371-381 (2009), the contents of which are hereby expressly incorporated by reference in their entireties for all purposes). Using fluorescently labeled ACPPs, improved surgical margin detection, decreased residual tumor burden, and improved survival in animal models of melanoma and breast cancer (Nguyen, Q. T. et al., *Proc Natl Acad Sci USA* 107, 4317-4322 (2010)) is shown.

Thrombin is a serine protease and a key regulator of blood coagulation. It is responsible for the proteolytic cleavage and activation of multiple coagulation factors including Factor V, VIII, XI as well as fibrinogen and protein C (E. W. Davie and J. D. Kulman, *Seminars in Thrombosis and Hemostasis* 2006, 32 Suppl 1, 3-15; J. A. Huntington, *Journal of Thrombosis and Haemostasis* 2005, 3, 1861-1872). Thrombin also cleaves and activates protease activated receptors (PARs) which are highly expressed on platelets, endothelial cells, myocytes and neurons (Vu T. K., et al., *Cell* 1991, 64, 1057-1068; Coughlin S. R., *Nature* 2000, 407, 258-264; Gallwitz M., et al., *PloS One* 2012, 7, e31756). Thrombin is a major therapeutic target for thrombosis and stroke intervention/prevention through indirect inhibitors such as heparin or warfarin, hirudin (divalent) and argatroban (monovalent) (Spyropoulos A. C., *Thrombosis Research* 2008, 123 Suppl 1, S29-35; Nutescu E. A., et al., *Cardiology Clinics* 2008, 26, 169-187, v-vi).

In addition to its role in thrombosis and stroke (Chen B, et al., *Stroke; a journal of cerebral circulation* 2010, 41, 2348-2352; Liu D. Z., et al., *Annals of neurology* 2010, 67, 526-533; Xue M. and Del Bigio M. R., *Stroke; a journal of cerebral circulation* 2001, 32, 2164-2169; Nishino A., et al., *Journal of Neurotrauma* 1993, 10, 167-179), thrombin is reported as a relevant player in cardiovascular disease (Leger A. J., et al., *Circulation* 2006, 114, 1070-1077; Aikawa E., et al., *Circulation* 2007, 116, 2841-2850), renal injury (Gupta A., et al., *Current drug targets* 2009, 10, 1212-1226), and cancer (Garcia-Lopez M. T., et al., *Current medicinal chemistry* 2010, 17, 109-128).

A number of fluorophore labeled peptide probes are known in the art. Chen et al.[7] describe zipper molecular beacons (ZMB) comprising an asymmetrical polyarginine/polyglutamate electrostatic "zipper" hairpin-linked fluorophore-quencher pair. However, Chen et al tested their probes only in protein-free buffers or conditioned media, not in animals. They had difficulty in getting the cleaved probes to dissociate from each other, probably because of the greater hydrophobicity of their donor (pheophorbide) and quencher (BHQ3) compared to ours (Cy5 and Cy7 respectively). In the absence of bulk tissues or high protein concentrations, the hydrophobicity of their dyes probably kept the cleavage fragments glued together. Because their quencher (BHQ3) was nonfluorescent, and they showed no lifetime measurements, they missed the specific spectroscopic signatures of enzyme-mediated cleavage. Furthermore, BHQ-3 has been shown to be too unstable and easily metabolized for in vivo imagine.

Activatable cell penetrating peptides (ACPPs) target various cargoes including fluorescent imaging agents to sites of protease activity in vivo (Jiang T., et al., *PNAS U.S.A.* 2004, 101, 17867-17872; Olson E. S., et al., *Integrative Biology: Quantitative Biosciences from Nano to Macro* 2009, 1, 382-393; Olson E. S., et al., *PNAS U.S.A.* 2010, 107, 4311-4316; Aguilera T. A., et al., *Integrative Biology: Quantitative Biosciences from Nano to Macro* 2009, 1, 371-381). ACPPs consist of a polycationic cell penetrating peptide attached to a cargo and a polyanionic inhibitory domain with a protease cleavable linker. Probe activation and cargo uptake depends on localized proteolysis of the linker sequence that connects the polyanionic and polycationic domains, which converts the probe to an adherent form. This method provides detection of spatially localized enzymatic activity in living tissues via accumulation of cleaved probe.

ACPPs have been previously reported that target MMPs (Jiang T., et al., PNAS U.S.A. 2004, 101, 17867-17872; Olson E. S., et al., *Integrative Biology: Quantitative Biosciences from Nano to Macro* 2009, 1, 382-393, the contents of which are hereby expressly incorporated by reference in their entireties for all purposes) and elastases (Whitney M., et al, *The Journal of Biological Chemistry* 2010, 285, 22532-22541, the content of which is hereby expressly incorporated by reference in its entirety for all purposes) to cancer. A thrombin activated ACPP with cleavage sequence (SEQ ID NO:1) DPRSFL, from the PAR1 receptor was recently reported for monitoring thrombin activation in atherosclerotic plaques (Olson E. S., et al., *Integrative Biology: Quantitative Biosciences from Nano to Macro* 2012, 4, 595-605, the content of which is hereby expressly incorporated by reference in its entirety for all purposes). This ACPP is efficiently cleaved by thrombin and accumulates in atherosclerotic plaques with increasing signal depending on plaque load. An optimized and more selective thrombin cleavable ACPP with a substrate sequence of (SEQ ID NO:2) PPRSFL has also been used to measure thrombin activation after brain injury (Chen B., et al., *The Journal of Neuroscience: the Official Journal of the Society for Neuroscience* 2012, 32, 7622-7631, the content of which is hereby expressly incorporated by reference in its entirety for all purposes).

Each of these ACPPs include a single fluorophore (Cy5) and therefore quantitative measurement required time to allow uncleaved peptide to wash out of the target tissue before contrast developed. Probes based on fluorescence dequenching have previously been used to detect thrombin activity during clot formation, but many factors other than enzyme activity also affect fluorescence intensity, and diffusion of the agent after cleavage limits signal intensity at the site of protease activation (Jaffer F. A., et al., *Arteriosclerosis, Thrombosis, and Vascular Biology* 2002, 22, 1929-1935; Tung C. H., et al., *Chembiochem: a European Journal of Chemical Biology* 2002, 3, 207-211, the contents of which are hereby expressly incorporated by reference in their entireties for all purposes).

Much work has been done with simpler FRET substrates lacking the polycationic and polyanionic domains characteristic of ACPPs, thus with a fluorescent donor and quencher linked by an enzyme-cleavable sequence[8]. Almost all this work has been done for in vitro enzyme assays, because this simple design has no inherent provision for hindering diffusion and washout of the cleavage product containing the dequenched donor fluorophore. Therefore loss of spatial resolution after cleavage is a great concern for in vivo imaging.

BRIEF SUMMARY OF THE INVENTION

Although FRET substrates for proteases have long been popular, the combination of ACPPs with FRET brings many important advantages. Enzymatic cleavage not only produces a large spectroscopic shift but also converts a diffusible substrate into an adhesive product, which remains localized at the site of cleavage to confer spatial resolution. The hairpin structure holds the donor and acceptor fluorophores (e.g., Cy5 and Cy7) at a distance conducive to FRET, rather than hydrophobically-driven stacking and mutual static quenching. Therefore cleavage causes a large (e.g., ~40×) change in emission ratio regardless of the substrate sequence or enzyme being sensed. Long wavelength fluorescent donors and acceptors (e.g., Cy5 and Cy7) are ideal for in vivo imaging, where excitation and emission wavelengths should be well above 600 nm to avoid the strong absorbencies of endogenous hemes. These properties are all optimized for the demanding application of in vivo imaging, with high spatial and temporal resolution using minimum probe concentration. For strictly in vitro assays, much smaller and simpler molecules may suffice (van Berkel S. S., et al., *ChemMedChem* 2012, 7, 606-617).

Accurate identification of whether or not a given lymph node contain cancer invasion is critical during cancer surgery. Current methods for sentinel lymph node (SLN) identification only localize the lymph node anatomically without any information regarding cancer involvement. To enable rapid molecular detection of metastatic lymph nodes during surgery, previously described ACPPs tagged with a single fluorophore (e.g., Cy5) have been augmented with a second fluorophore (e.g., Cy7) which acts as an acceptor for FRET emission. Protease attack simultaneously disrupts fluorescence resonance energy transfer and releases a highly adhesive donor fluorophore-labeled CPP (e.g., Cy5-labeled CPP). As demonstrated herein, systemic injection of these ratiometric ACPPs (RACPPs) results in MMP-2,-9 dependent tumor and metastatic lymph node contrast at 45 min and 2 h post-injection, respectively.

In one aspect, the present disclosure provides ratiometric ACPPs that combine the triggered retention inherent to ACPPs with the advantages of spectral imaging to detect spatial and temporal changes in thrombin activity in vivo within minutes of probe injection.

Ratiometric imaging represents a significant advantage over previously described single wavelength intensity measurements because it allows cancer specific discrimination relatively independent of dose, pharmacokinetics, optical variables, and thresholding. The advantages of ratiometric vs. single-intensity measurements are well known (Tsien, R. Y. & Harootunian, A. T. *Cell Calcium* 11, 93-109 (1990)) in fluorescence microscopy and flow cytometry, but have hitherto been neglected in intraoperative molecular imaging. The time to develop sensitive cancer to background contrast (1-2 hours) allows intraoperative real time assessment of lymph node status and represents a significant advance over current SLN detection methods, which identify node location without any information regarding cancer invasion.

In one aspect, the present disclosure provides a compound having the structure:

PAP-CL-PCP wherein: PAP is a polyanionic peptide comprising a fluorescence acceptor; CL is a first linker, wherein the first linker is cleavable; and PCP is a polycationic peptide comprising a fluorescence donor comprising a cyanine.

In one embodiment of the compositions described above, the compound further comprises a targeting moiety. In a specific embodiment of the compositions described above, the targeting moiety is attached via a second linker. In a more specific embodiment of the compounds described above, the second linker is attached to a first derivatized amino acid in the polyanionic peptide. In a more specific embodiment of the compositions described above, the second linker comprises a water soluble polymer, e.g., poly(ethyleneglycol). In one embodiment of the compositions described above, the first derivatized amino acid is derivatized cysteine.

In one embodiment of the compositions described above, the fluorescence donor is attached to a second derivatized amino acid in the polycationic peptide. In one aspect of the compositions described above, the second derivatized amino acid is derivatized cysteine.

In one embodiment of the compositions described above, the polyanionic peptide comprises nine glutamine residues.

In embodiment of the compositions described above, the polycationic peptide comprises nine arginine residues.

In one embodiment of the compositions described above, the second derivatized amino acid is derivatized cysteine In one embodiment of the compositions described above, the cleavable linker is an MMP-9 or MMP-2 substrate.

In one embodiment of the compositions described above, the second derivatized amino acid is derivatized cysteine. one or both of the fluorescence donor and the fluorescence acceptor independently have a structure according to

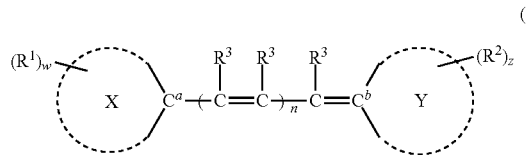

(I)

wherein the dotted lines encircling X and Y are each independently selected from atoms necessary for the formation of one ring to three fused rings having 4 to 7 atoms in each ring; at least one atom in the ring comprising $C^a$ is a nitrogen; at least one atom in the ring comprising $C^b$ is a nitrogen; the indices w and z are integers independently selected from 0 to the number of atoms necessary for the formation of X or Y, with the proviso that w and z cannot both be 0; each $R^3$ is a member independently selected from H, $OR^{30}$, $SR^{30}$, $NR^{30}R^{30}$, halogen, CN, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; two $R^3$ groups, together with the atoms to which they are attached, can be optionally joined to form a ring; the index n is an integer selected from 0, 1, 2, 3 and 4; $R^1$ and $R^2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, $SO_3$, $NO_2$, CN, P(O)$(OR^4)(OR^5)$, $D^1R^6$, $NR^7R^8$ and $C(D^2)R^9$; $D^1$ is a member selected from O and S; $D^2$ is a member selected from O, S and NH; $R^4$ and $R^5$ are members independently selected from H, substituted or unsubstituted $C_1$-$C_4$ alkyl, substituted or unsubstituted $C_1$-$C_4$ heteroalkyl; at least one of $R^4$ and $R^5$ is H; $R^6$, $R^7$ and $R^8$ are members independently selected from H, substituted or unsubstituted alkyl and substituted or unsubstituted heteroalkyl; $R^7$ and $R^8$, together with the nitrogen to which they are attached, can be optionally joined to form a member selected from a reactive functional group, —NHNH$_2$, —N=N=N, —N=C=S and —N=C=O; $R^9$ is a member selected from H, substituted or unsubstituted alkyl, substituted or unsubstituted heteroalkyl, a reactive functional group, $NR^{10}R^{11}$ and $OR^{12}$; $R^{16}$ and $R^{11}$ are members independently selected from H, substituted or unsubstituted alkyl and substituted or unsubstituted heteroalkyl; $R^{12}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and C(O)$R^{13}$; $R^{13}$ is a member selected from substituted or unsubstituted alkyl and substituted or unsubstituted heteroalkyl; and each $R^{30}$ is independently selected from H, a negative charge and a salt counterion.

In one embodiment of the compositions described above, the second derivatized amino acid is derivatized cysteine, the fluorescence donor is Cy5.

In one embodiment of the compositions described above, the second derivatized amino acid is derivatized cysteine, the fluorescence acceptor is Cy7.

In one embodiment of the compositions described above, the second derivatized amino acid is derivatized cysteine, the fluorescence acceptor is a nonfluorescent quencher.

In another aspect, the present disclosure provides a method for detecting a tumor, comprising: (a) contacting the tumor with an RACPP compound described herein, the compound characterized by a fluorescence resonance energy transfer (FRET) property; and (b) detecting a change in the FRET property of the compound after contact with the tumor.

In one embodiment of the methods described above, the detecting step comprises detecting an increase in a ratio of donor emission to acceptor reemission or detecting an increase in donor excited state lifetime.

In another aspect, the present disclosure provides a method for detecting activity of a proteolytic enzyme in a subject, comprising: (a) administering to the subject a compound having the structure:

PAP-CL-PCP wherein: PAP is a polyanionic peptide comprising an acceptor fluorophore; CL is a first linker comprising a peptide sequence cleavable by the proteolytic enzyme; and PCP is a polycationic peptide comprising a donor fluorophore, wherein the donor fluorophores is capable of participating in FRET with the acceptor fluorophore; (b) illuminating a region of interest on the subject with light having a first wavelength, the first wavelength capable of exciting the donor fluorophore but not the acceptor fluorophore; and (c) detecting fluorescent emissions from the donor and acceptor fluorophores.

In another aspect, the present disclosure provides a method for detecting a cancerous tissue in a subject, comprising: (a) administering to the subject a compound having the structure:

PAP-CL-PCP wherein: PAP is a polyanionic peptide comprising an acceptor fluorophore; CL is a cleavable linker comprising a peptide sequence cleavable by an enzyme selected from MMP-2, MMP-9, and an elastase; and PCP is a polycationic peptide comprising a donor fluorophore, wherein the donor fluorophores is capable of participating in FRET with the acceptor fluorophore; (b) illuminating a region of interest on the subject with light having a first wavelength, the first wavelength capable of exciting the donor fluorophore but not the acceptor fluorophore; and (c) detecting fluorescent emissions from the donor and acceptor fluorophores.

In one embodiment of the methods described above, the cancerous tissue is detected in real-time during a surgical procedure.

In another aspect, the present disclosure provides a method for detecting a blood clot in a subject, comprising: (a) administering to the subject a compound having the structure:

PAP-CL-PCP wherein: PAP is a polyanionic peptide comprising an acceptor fluorophore; CL is a cleavable linker comprising a peptide sequence cleavable by thrombin; and PCP is a polycationic peptide comprising a donor fluorophore, wherein the donor fluorophores is capable of participating in FRET with the acceptor fluorophore; (b) illuminating a region of interest on the subject with light having a first wavelength, the first wavelength capable of exciting the donor fluorophore but not the acceptor fluorophore; and (c) detecting fluorescent emissions from the donor and acceptor fluorophores.

In one embodiment of the methods described above, the blood clot is detected in real-time during a surgical procedure.

In another aspect, the present disclosure provides a method for detecting an atherosclerotic plaque in a subject, comprising: (a) administering to the subject a compound having the structure:

PAP-CL-PCP wherein: PAP is a polyanionic peptide comprising an acceptor fluorophore; CL is a cleavable linker comprising a peptide sequence cleavable by thrombin; and PCP is a polycationic peptide comprising a donor fluorophore, wherein the donor fluorophores is capable of participating in FRET with the acceptor fluorophore, (b) illuminating a region of interest on the subject with light having a first wavelength, the first wavelength capable of exciting the donor fluorophore but not the acceptor fluorophore; and (c) detecting fluorescent emissions from the donor and acceptor fluorophores.

In one embodiment of the methods described above, the atherosclerotic plaque is detected in real-time during a surgical procedure.

In one embodiment of the methods described above, the detecting step comprises: (1) detecting fluorescent emission at a first wavelength near or at an emission maximum of the donor fluorophore; and (2) detecting fluorescent emission at a second wavelength near or at an emission maximum of the acceptor fluorophore.

In one embodiment of the methods described above, the method further comprises: (d) reporting a value for the ratio of fluorescent emissions at the first and second wavelengths at one or more regions of interest on the subject.

In one embodiment of the methods described above, the reporting step comprises displaying an image of the one or more regions of interest on the subject, the image being psuedocolored according to the value of the ratio of fluorescent emissions at the first and second wavelengths.

In one embodiment of the methods described above, the step of detecting fluorescent emissions from the donor and acceptor fluorophores comprises: (1) capturing a multispectral image of a region of interest on the subject; and (2) deconvoluting the multispectral image to determine the component fluorescent emission contributions from the donor and acceptor fluorophores.

In one embodiment of the methods described above, the method further comprises: (d) displaying a multispectral image of a region of interest on the subject, the multispectral image comprising information on the fluorescent emissions of the donor and acceptor fluorophores.

In one embodiment of the methods described above, the multispectral image displayed is pseudocolored according to one or more threshold values. In one embodiment of the methods described above, the multispectral image is pseudocolored according to a continuous gradient of component contributions.

In one embodiment of the methods described above, the acceptor fluorophore is a cyanine. In a specific embodiment of the methods described above, the acceptor fluorophore is Cy7.

In one embodiment of the methods described above, the donor fluorophore is a cyanine. In a specific embodiment of the methods described above, the donor fluorophore is Cy5.

In one embodiment of the methods described above, the first linker comprises a peptide having an amino acid sequence selected from (SEQ ID NO:3) PLGCAG and (SEQ ID NO:4) RLQLKL.

In one embodiment of the methods described above, the first linker comprises a peptide having an amino acid sequence selected from (SEQ ID NO:2) PPRSFL and (SEQ ID NO:1) DPRSFL.

In one embodiment of the methods described above, the compound further comprises a targeting moiety. In a specific embodiment of the methods described above, the targeting moiety is attached to the compound via a second linker. In a more specific embodiment of the methods described above, the second linker is attached to a first derivatized amino acid in the polyanionic peptide. In a more specific embodiment of the methods described above, the second linker comprises a water soluble polymer, e.g., poly(ethyleneglycol).

In one embodiment of the methods described above, the fluorescence donor is attached to a second derivatized amino acid in the polycationic peptide.

In one embodiment of the methods described above, the polyanionic peptide comprises nine glutamine residues.

In one embodiment of the methods described above, the polycationic peptide comprises nine arginine residues.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1 compares in vivo imaging contrast achieved using a standard ACPP with contrast obtained using a FRET-ACPP, as disclosed herein.

FIG. 5 shows in vivo fluorescence lifetime imaging of HT-1080 tumors in mice using FRET-ACPP 2 (5A and 5B) and FRET-ACPP 3 (5C and 5D) substrates.

FIG. 8 shows in vivo multispectral imaging of syngenic MMTV-PyMT mammary tumors (Tu) in mice whose MMP-2 and MMP-9 are wild-type (+/+) or deficient (−/−) using the FRET-ACPP 2 substrate. Deconvoluted pixels are displayed as green (Cy5-Cy7 FRET), red (Cy5 fluorescence only), or light blue (variable autofluorescence of fur) to indicate the source of the detected fluorescence.

FIG. 9A shows an in vivo emission ratio image of a mouse containing an MBA-MDA 231 tumor, after injection of the FRET-ACPP 1 substrate. The deconvoluted pixels are displayed as blue (highest FRET efficiency), green (intermediate FRET efficiency), yellow (intermediate FRET efficiency), or red (lowest FRET efficiency), indicating the extent of FRET-ACPP 1 substrate cleavage in vivo.

FIG. 9B shows hematoxylin/eosin (H and E) staining of the indicated region in FIG. 9A, showing the lowest FRET efficiency.

FIG. 12 shows in vivo multispectral imaging of HT-1080 mouse xenographs using targeted FRET-ACPP substrates. The mice were imaged 2 hours and 15 minutes after IV injection of the FRET-ACPP substrates and after skin removal.

FIG. 15 shows 10% tricine polyacrylamide gels (A, B) demonstrating Cy5 (A) and Cy7 (B) emission images with uncleaved (well 1) and cleaved RACPP2 (well 2) and urine samples from mice 2 hr (well 3) and 24 hr (well 4) following IV injection of RACPP2. Note that at the 2 hour time point, there is no cleaved r9 (labeled with Cy5) fragment in the urine (A, yellow asterisk), consistent with tumor rather than systemic cleavage of RACPP2. However, at the 24 hour time point, the r9 fragment is present in the urine (A, blue asterisk), albeit at much lower level, consistent with loss of tumor specific contrast at later times. MMP-9 treated sample in well 2 was diluted by ~four-fold compared to well 1. (C) Emission spectra of RACPP2 obtained in a cuvet spectrofluorometer before (red line) and after (blue line) treating it with MMP-9 in mouse plasma.

FIG. 18 A-D show spectrally classified images of mice bearing syngeneic MMTV-PyMT derived 8119 mammary tumors, whose MMP-2,-9 levels are normal (labeled WT) or deficient (KO) following systemic IV RACPP1 injection. KO (A) and WT (B) mice showed high FRET ~5 min post injection. Significant loss of FRET was seen 45 min post injection in WT (C) but not in KO (D). Pseudocolor red indicates a high ratio of Cy5:Cy7 emission (e.g., presence of the cleaved probe), pseudocolor green indicates a low ratio of Cy5:Cy7 emission (e.g., presence of the uncleaved probe only), while light blue indicates variable autofluorescence from fur. Spectrally classified (E, G) and ratio (F, H) images of mice bearing HT-1080 tumors show tumor contrast 2 hr (E, F) after IV injections of RACPP2, but this contrast washes out by 24 hr when most tissues only contain cleaved product (G, H).

FIG. 19 shows Cy5/Cy7 ratiometric and spectral images of syngeneic 8119 tumor bearing mice whose MMP-2,-9 levels either are normal (WT) or deficient (KO) following IV injection with either RACPP1 (A-D) or uncleavable control (E-L). Ratio images obtained after 5 min (A, B) from KO (A) or WT (B) mice did not show tumor contrast. RACPP1 produced high tumor contrast 45 min following IV injection in WT (D) but not in KO mice (C). Uncleavable control did not produce ratio (E-H) or spectral (I-L) contrast at 5 min (E, F, I, J) or 45 min (G, H, K, L) following injection in KO (E, G, I, K) or WT (F, H, J, L) mice. In spectral images (I-L) the green pseudocolor on the tumor regions indicates the presence of uncleaved probe, pseudocolor cyan indicates the variable autofluorescence. White arrows indicate tumor regions. Zymogram gel analysis verified the presence of MMP-2,-9 activity in tumor samples from WT, but not in KO models (data not shown).

FIG. 21 shows various images of livers containing PyMT 8119 GFP positive metastases, harvested from mice 2 hr after IV injection of RACPP1 (MMP-2,-9-selective, A-D) or RACPP3 (elastase-sensitive, E-H). (A, E) GFP fluorescence images. (B, F) Cy5 fluorescence images obtained by exciting Cy5 at 620 nm. (C, G) Cy7 emission images obtained by exciting Cy5. (D, H) Cy5/Cy7 emission ratio images. Ratio images showed better correlation with GFP reference emission images than either Cy5 or Cy7 independent images. The ratio contrast for metastases relative to normal liver was higher for RACPP3 (H) than for RACPP1 (D). Arrows exemplify two of the many nontumor regions (as judged by lack of GFP fluorescence), where both Cy5 and Cy7 fluorescence intensities were high, resulting in relatively low ratios.

Figures 25A, 25B, 25C:
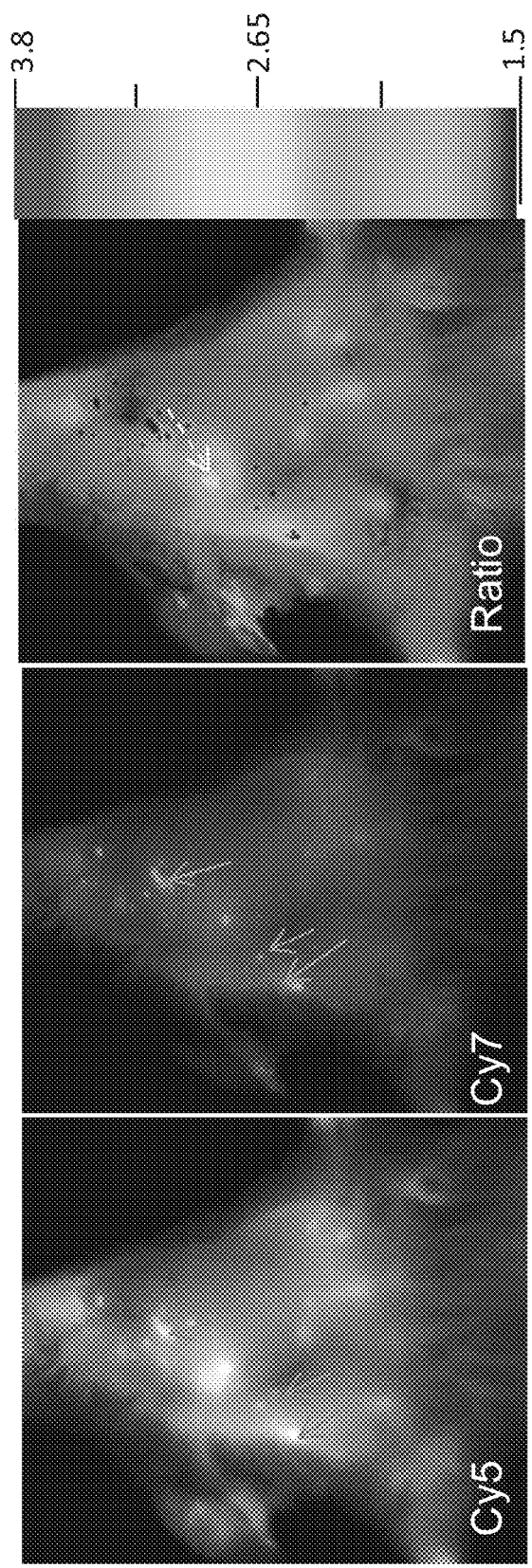
Figure 27A:
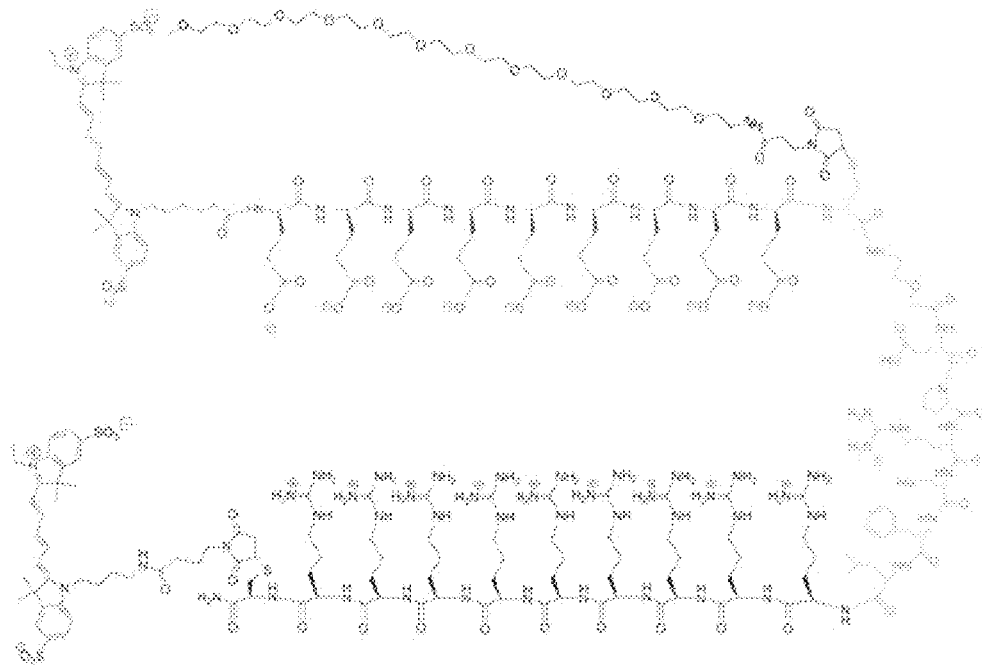
Figure 27B:
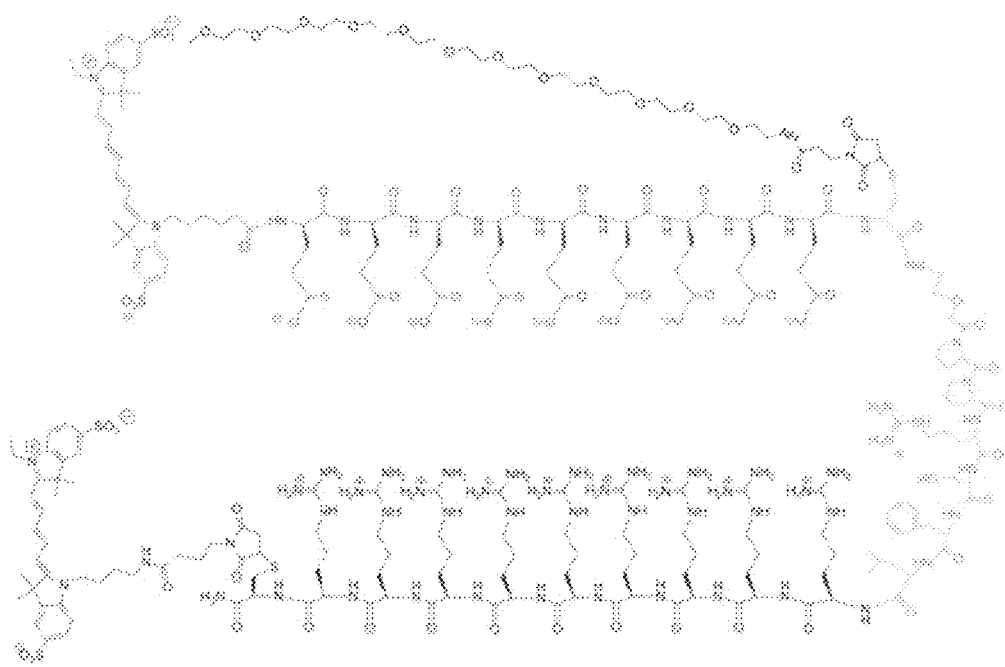
Figure 27C:
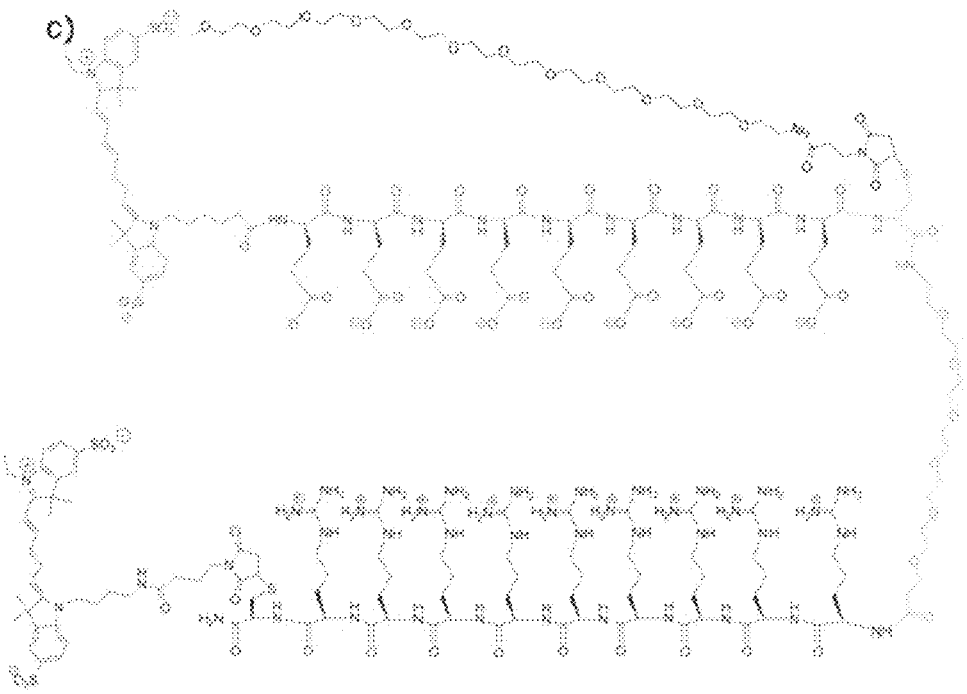
Figure 27D:
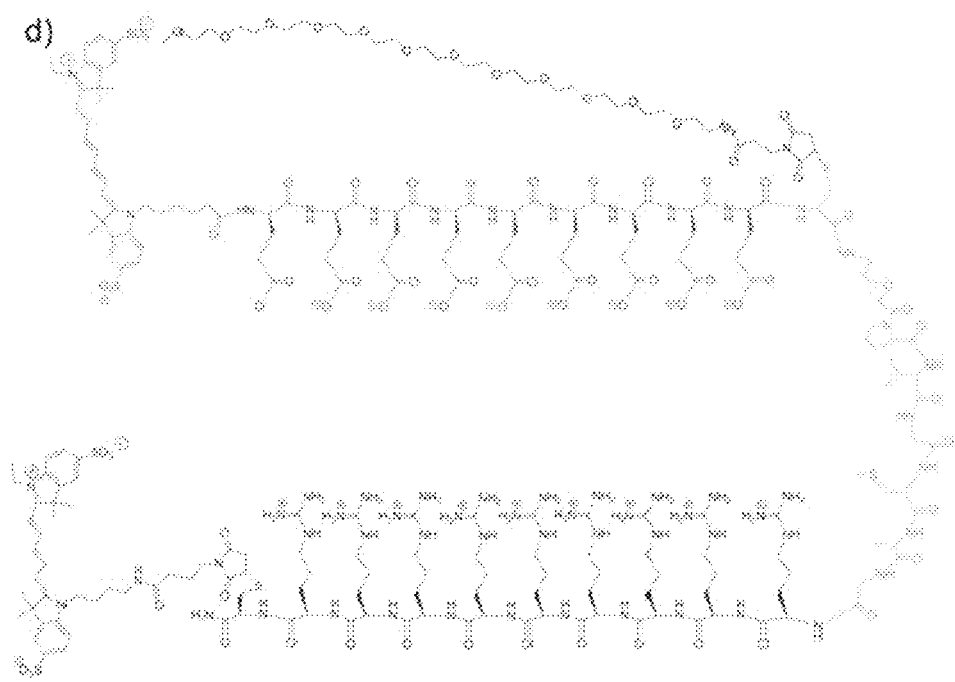

FIG. 25 shows images of Cy5 (A), Cy7 (B) emission by exciting Cy5, Cy5/Cy7 emission ratio (C) obtained at 2 hr following IV injection of RACPP1 into mice bearing 8119 primary auricular tumor with metastatic cervical lymph node. Many high fluorescence intensity spots (seen in both A and B, blue arrows) are cancelled out in ratio image, indicating the absence of cancer invasion in these areas. In contrast, both the primary tumor (C, white solid arrow) and the cervical lymph node with histologically confirmed cancer invasion (C, white dotted arrow) show high Cy5/Cy7 ratio contrast, emphasizing the advantage of ratiometric imaging.

FIG. 26 outlines the general method for the synthesis of RACPP peptide substrates according to one embodiment.

FIG. 27 provides the chemical structures of RACPP peptide substrates (SEQ ID NO:1) $RACPP_{DPRSFL}$ (compound 5; A), (SEQ ID NO:2) $RACPP_{PPRSFL}$ (compound 10; B), $RACPP_{peg6}$ (compound 15; C), and (SEQ ID NO:7) $RACPP_{PLGC(Me)AG}$ (compound 20; D).

Figure 28A:
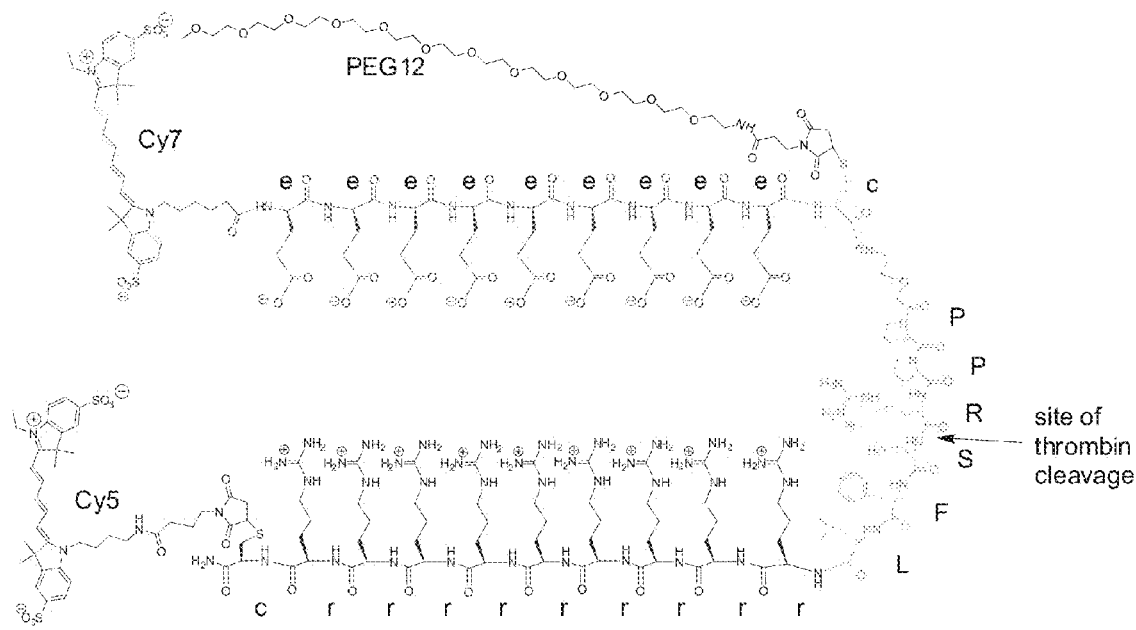

FIG. 28A provides the chemical structure of (SEQ ID NO:2) $RACPP_{PPRSFL}$. A polyanionic domain (red) is connected via PPRSFL, a thrombin-cleavable linker (green), to a polyarginine domain (blue) conjugated to Cy5.

Figure 28B:
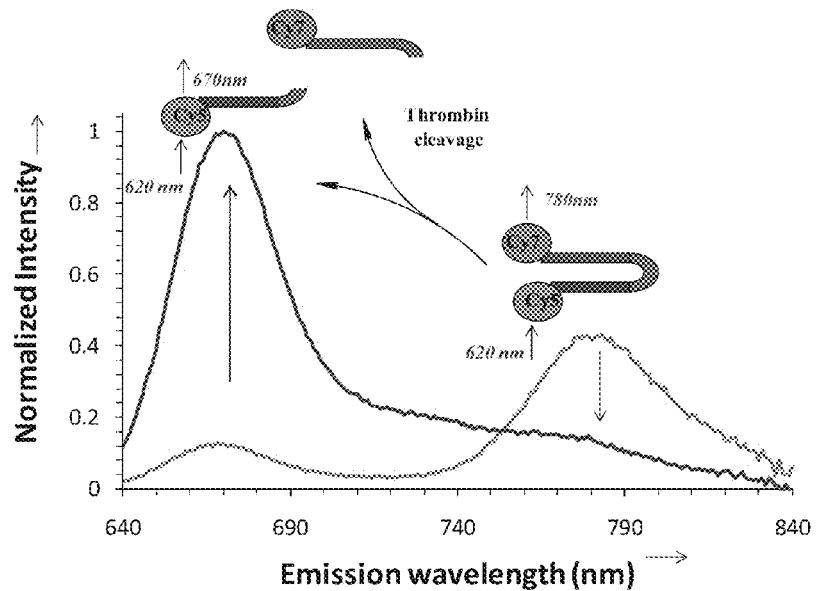

FIG. 28B shows the emission spectrum of (SEQ ID NO:2) $RACPP_{PPRSFL}$, measured in mouse plasma in a cuvet spectrofluorometer, before (red curve) and after (blue curve) treatment with thrombin. Before cleavage Cy5 is quenched by Cy7, which re-emits at 780 nm. After cleavage Cy7 no longer quenches Cy5, so the 670 nm peak from Cy5 increases and Cy7 re-emission disappears. The residual shoulder from 710 to 840 nm is largely from Cy5.

Figure 29:
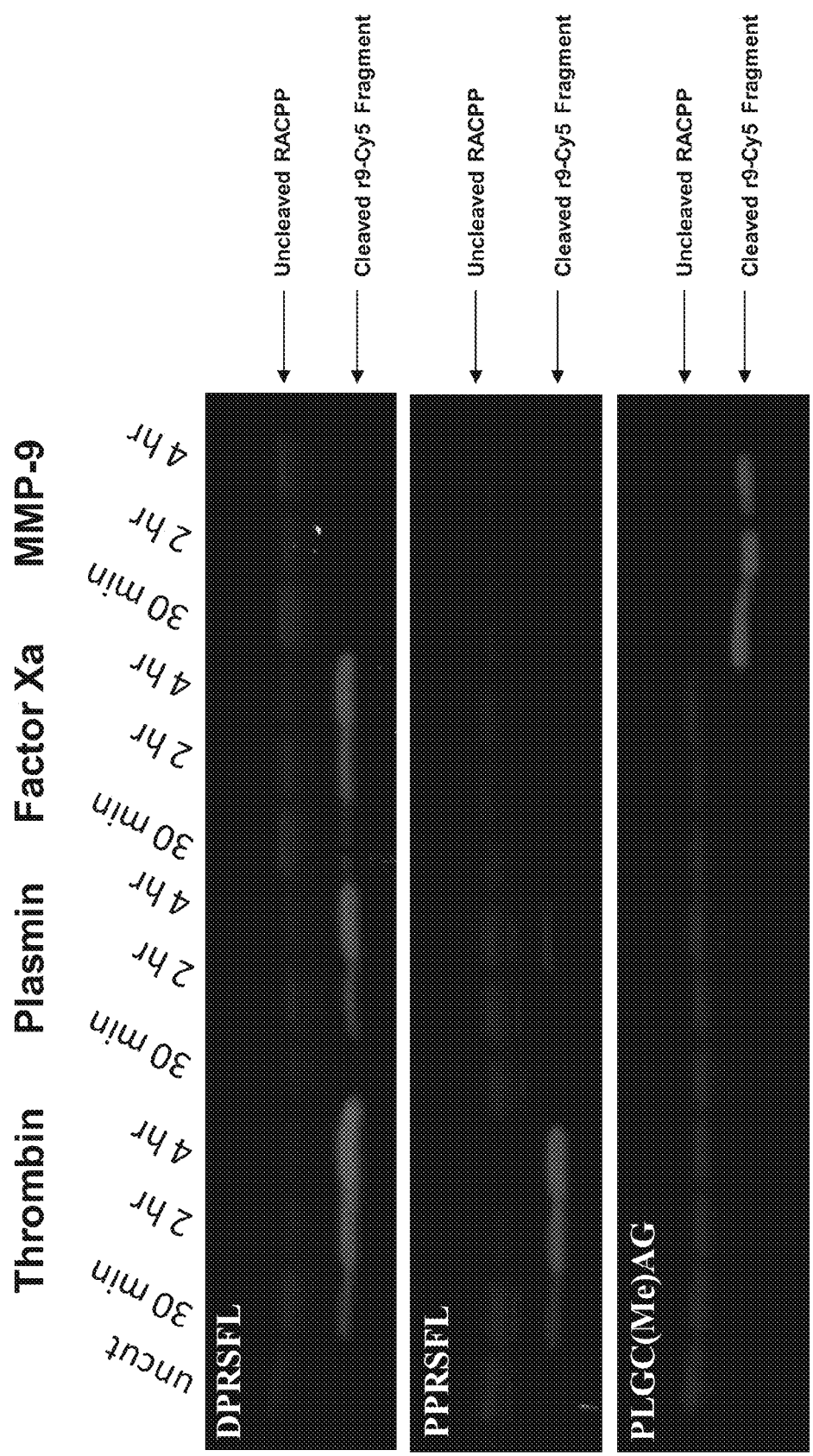

FIG. 29 shows SDS-PAGE analysis of RACPP peptide cleavage by purified thrombin, plasmin, factor Xa, and MMP-9. Three RACPPs (top: (SEQ ID NO:1) DPRSFL, middle: (SEQ ID NO:2) PPRSFL, and bottom panel: (SEQ ID NO:7) PLGC(Me)AG) were separately exposed to purified enzymes for the times indicated. Peptide cleavage products were separated by electrophoresis using tricine-SDS polyacrylamide gels and imaged using the Maestro with 620 nm excitation, and emission collected for Cy5 (660 to 720 nm) or Cy7 (760 to 830 nm). Ratiometric images were synthesized by dividing the Cy5 emission with Cy7 emission and pseudocolored from blue (ratio minimum) to red (ratio maximum). In this gel, the polyanion released by enzyme attack is nearly invisible because it only bears Cy7.

Figure 30:
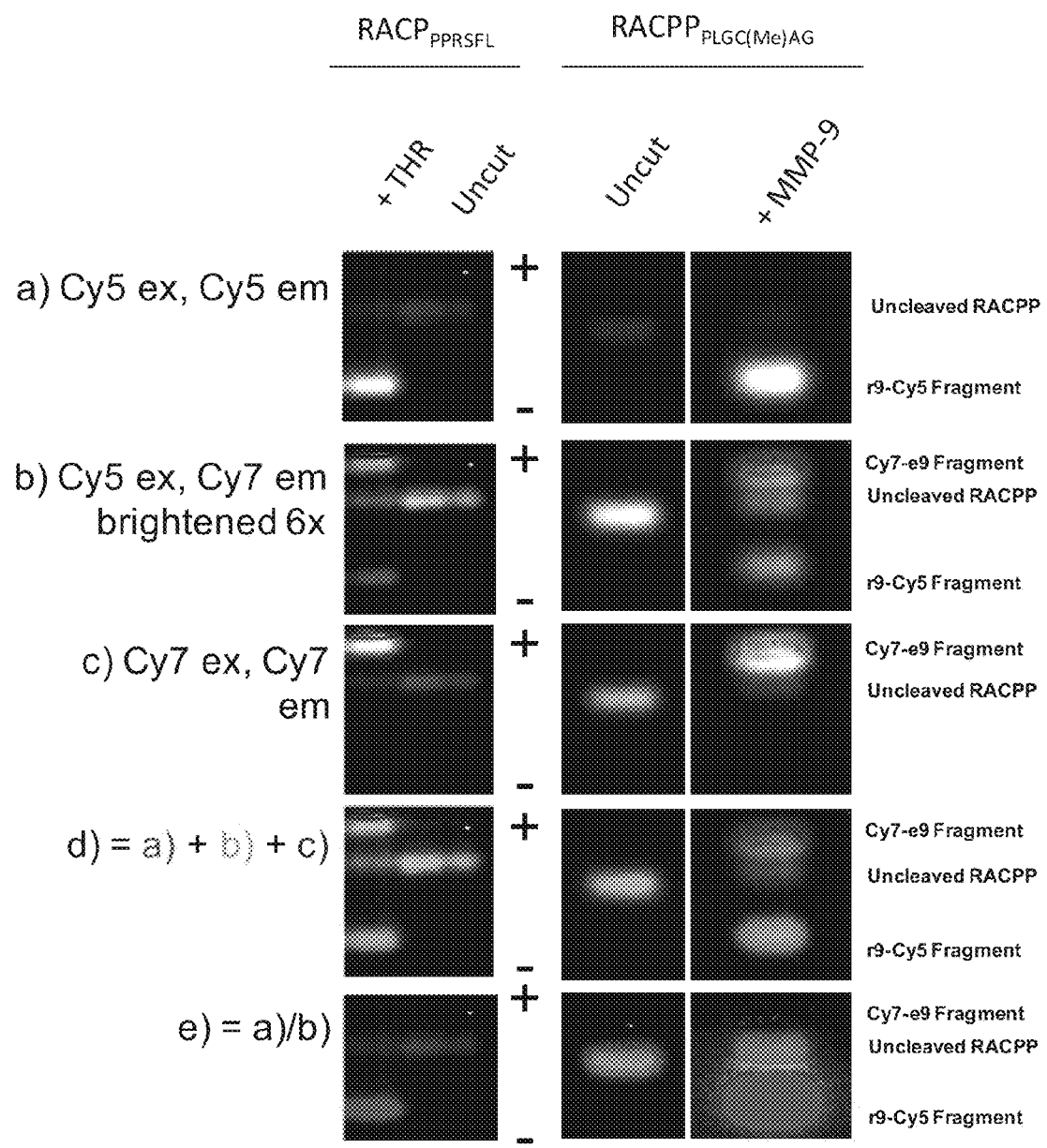

FIG. 30 shows PEHA-Acetate agarose gel electrophoretic analysis of (SEQ ID NO:2) $RACPP_{PPRSFL}$ (5) and (SEQ ID NO:7) $RACPP_{PLGC(Me)AG}$ (20) cleavage by 100 nM MMP-9 or thrombin. Digested peptides were separated on 4% agarose gels in 50 mM pentaethylenehexamine-acetate at pH 5.6. Gels were imaged for a) Cy5 fluorescence, b) Cy7 fluorescence upon exciting Cy5, brightened 6-fold, and c) Cy7 fluorescence. Panel d) is an overlay of a) in red, b) in green, and c) in blue. Panel e) is a pseudocolor Cy5/Cy7 emission ratio image of panels a) and b). The two RACPPs were run on separate gels with the electrophoretic polarity shown between them. The thin white separation in the (SEQ ID NO:7) $RACPP_{PLGC(Me)AG}$ gel marks where irrelevant lanes and specular reflections were excised for clarity.

Figure 31A:
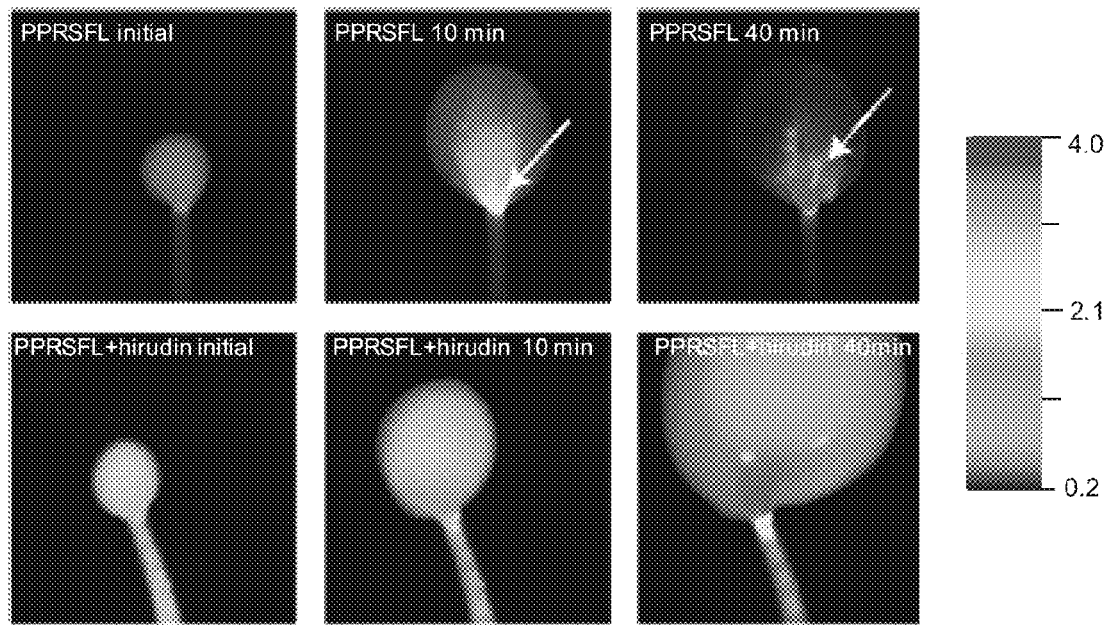

FIG. 31 shows the detection of thrombin activity in developing blood clots. (A) Ratiometric fluorescent images showing changes in Cy5/Cy7 emission ratios from tail clots of mice that had been injected with either (SEQ ID NO:2) $RACPP_{PPRSFL}$ (top row) or (SEQ ID NO:2) $RACPP_{PPRSFL}$ with prior injection of hirudin (bottom row). Initial images (left column) were taken within five minutes of injury followed by images at 10, 20, and 40 minutes post injury (20 minute images not shown). A Cy5/7 ratio increase was detectable at 10 minutes as shown by the arrow (top row/middle) and reached 4 fold by 40 minutes (top right) for (SEQ ID NO:2) $RACPPP_{PRSFL}$. Pre-treatment with hirudin attenuates Cy5/7 ratio changes throughout 40 minutes of clotting (bottom row). (B) Graph showing quantitative analysis of images shown in FIG. 31A with additional animals that were injected with either (SEQ ID NO:2) $RACPP_{PPRSFL}$ (n=5), (SEQ ID NO:2) $RACPP_{PPRSFL}$ with hirudin (n=3), $RACPP_{peg6}$ (n=3), or (SEQ ID NO:7) $RACPP_{PLGC(Me)AG}$ (n=4). Fluorescent intensities were acquired from rectangular areas that extended from the width of the tip of the cut tail to the edge of the blood clot using ImageJ. Cy5 fluorescent intensities were divided by Cy7 intensities and the ratios were plotted as mean±SD for each treatment group.

Figure 31B:
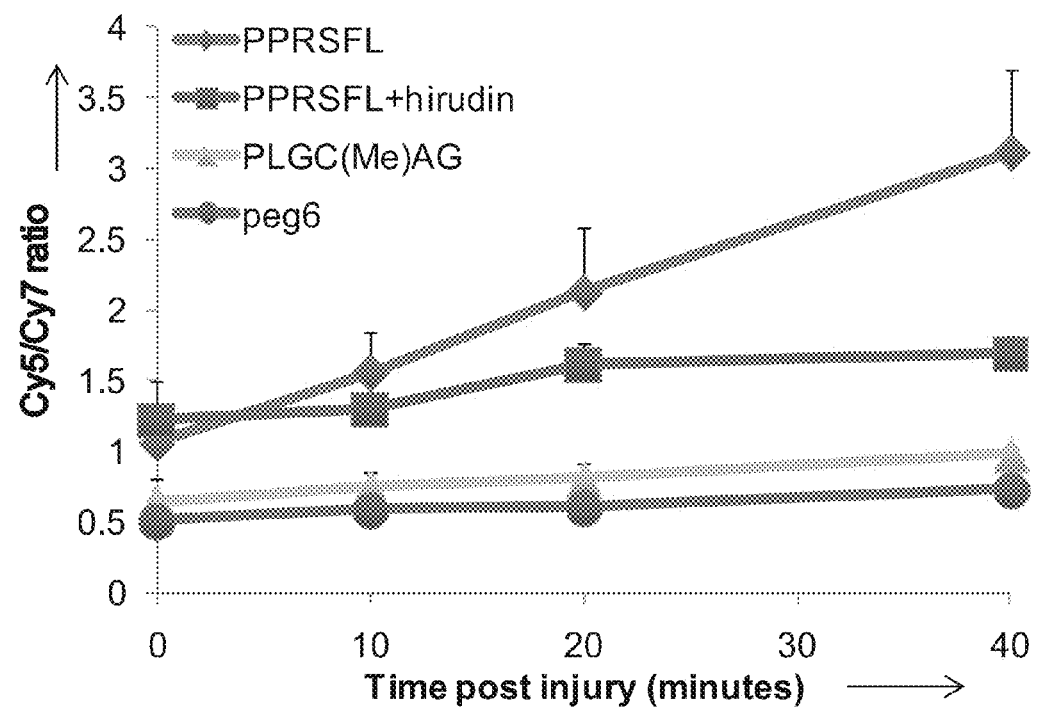
Figure 32:
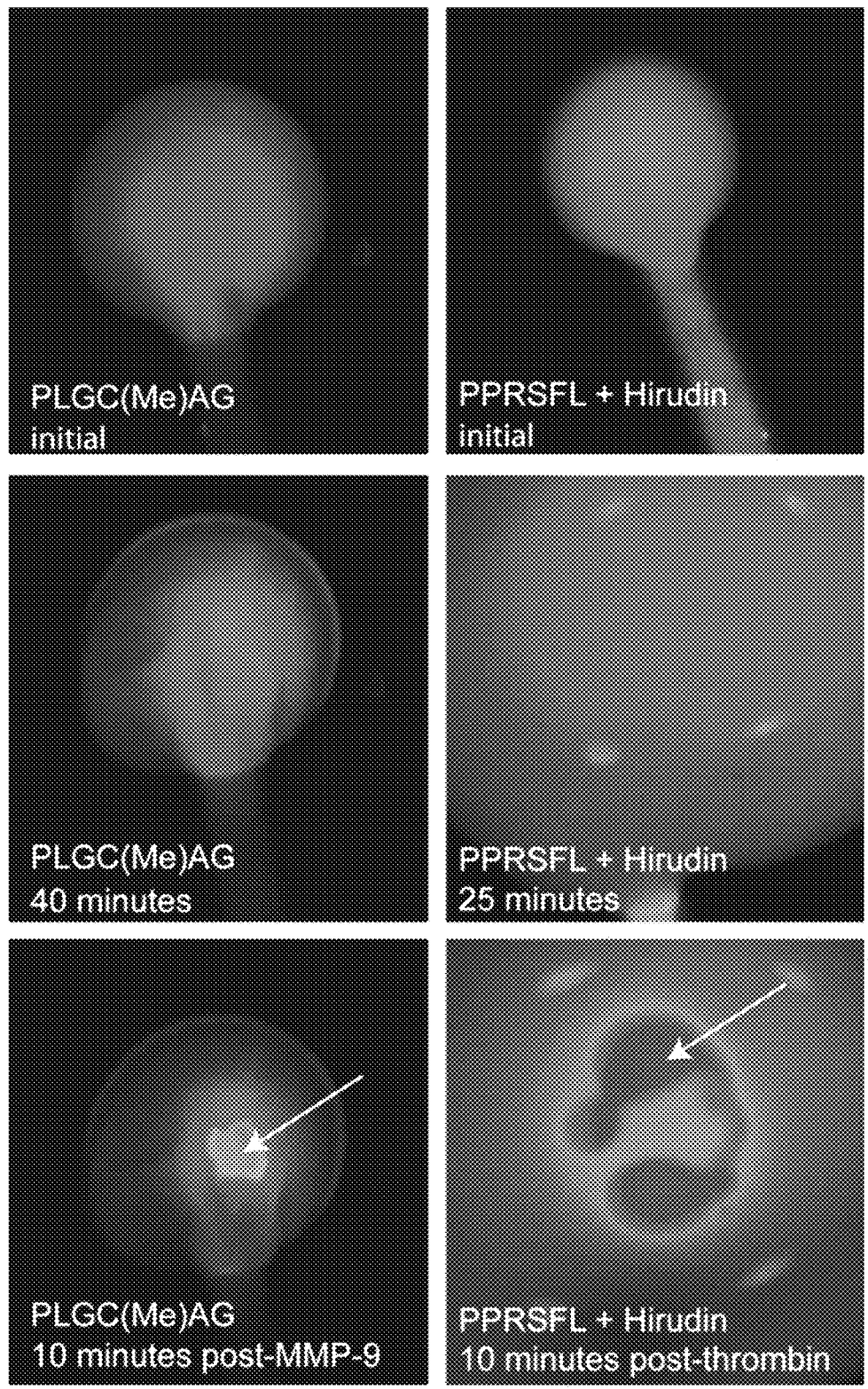

FIG. 32 shows ratiometric fluorescent images of exudates from tail injuries in mice injected with RACPPs ((SEQ ID NO:7) PLGC(Me)AG (20) or (SEQ ID NO:2) PPRSFL (5) with hirudin), before and after the addition of exogenous enzyme. Images were taken 5 minutes after injection (top row), 40 minutes ((SEQ ID NO:7) $RACPP_{PLGC(Me)AG}$), or 25 minutes post injury ((SEQ ID NO:2) $RACPP_{PPRSFL}$) (middle row), or 10 minutes after local addition of either MMP-9 (1 μl of 1.5 μM, bottom left) or thrombin (10 μl of 5 μM, bottom right). In each case there was little ratio change until the addition of exogenous enzyme (bottom row). Addition of the appropriate enzyme caused an increase of Cy5/Cy7 emission ratio (arrows). Color scale is identical to FIG. 31.

FIG. 33 shows the detection of thrombin activity in atherosclerotic plaques. (A) In vivo imaging of the carotid artery in ApoE$^{-/-}$ mice after 3 months of high fat diet following systemic injection with (SEQ ID NO:1) $RACPP_{DPRSFL}$ showing an atherosclerotic plaque at the bifurcation with white light reflectance. (B) Fluorescence imaging of the same carotid artery (stippled lines) showing variable Cy5/Cy7 ratios within the visible plaque, indicating heterogeneity in thrombin levels within the plaque. Note that the vagus nerve immediately adjacent to the carotid artery has a similar whitish opacity as the plaque within the carotid bifurcation on white light reflectance but can be easily differentiated with fluorescence imaging by its lack of probe uptake. (C) Ex vivo image of ApoE$^{-/-}$ mice after 3 months of high fat diet following systemic injection with $RACPP_{DPRSFL}$ showing extensive atherosclerotic plaques at the level aortic arch, brachiocephalic trunk and bilateral carotid arteries. (D) Fluorescence ratio imaging of the same vessels (contained within the stippled lines) showing variable Cy5/Cy7 ratios indicating heterogeneity in thrombin levels within the visible plaques. Cy5/Cy7 ratios were low (green color-lower thrombin activity) for plaques at the mid-level of the brachiocephalic trunk (arrow) compared to plaques with higher ratios (orange/red color-higher thrombin activity) at the root of the aorta (three asterisks), brachiocephalic trunk (double asterisks) or within the right and left carotid arteries (single asterisks).

DETAILED DESCRIPTION OF THE INVENTION

I. Introduction

Activatable cell penetrating peptides (ACPPs) are peptide-based molecules in which a polycationic sequence, for example comprising 8-12 arginines in one embodiment, is connected by an enzyme cleavable linker to a polyanionic sequence, typically comprising a matching number of glutamates[1-6]. We now disclose a new subclass of ACPP with a donor fluorophore attached to the polycationic peptide and an acceptor fluorophore attached to the polyanionic peptide, such that in the intact ACPP, there is efficient fluorescence resonance energy transfer (FRET) from the donor to the acceptor. Upon enzymatic cleavage of the linker, this FRET is disrupted while the adhesiveness of the polycation is unmasked. Loss of FRET can be monitored by standard methods, such as an increase in ratio of donor emission to acceptor re-emission or an increase in donor excited state lifetime. These FRET-ACPP substrates are useful, for example, in monitoring the extracellular enzymatic activity at diseased locations in live animals (e.g., human patients) in real-time by either measuring the ratio of donor to acceptor emissions or donor lifetime.

This technique represents a significant advance over existing non-ratiometric activatable protease sensors for both research and clinical use. Until now, injectable activatable or "smart" sensors for in vivo optical imaging have all signaled protease activity as simple increases in fluorescence. Microscopists have long realized the superiority of ratiometric readouts, particularly ratios of intensities at two wavelengths where a single molecular probe gives opposite signs of response. As we show experimentally herein, ratioing cancels out many artifacts that confound single-intensity measurements. However, it has been very difficult to find long-wavelength donor-acceptor pairs that give efficient FRET in small molecules with significant re-emission from the acceptor, as required for an emission ratiometric response. Typically, the two large chromophores used in these FRET substrates stack hydrophobically and quench each other. Advantageously, the molecular architecture of the FRET-ACPP substrates provided herein permits efficient re-emission from the acceptor fluorophore (e.g., Cy7) and provide a non-genetic solution for fast and sensitive in vivo quantitation and localization of a wide variety of lytic activities.

This technology also represents a significant advance compared to current sentinel lymph node detection methods, which give no information regarding cancer invasion. Future intraoperative implementation of FRET-ACPP should decrease the incidence of positive margins, minimize time spent waiting for a pathologist to scrutinize frozen-sectioned margins, and streamline intraoperative decision making by providing real-time knowledge of lymph-node status during surgery.

In an optional variation of the core design, the acceptor fluorophore can be replaced by a nonfluorescent quencher, which can be as small as a nitrophenyl group. Such small quenchers simplify synthesis and may improve stability and pharmacokinetics, but sacrifice dual-emission ratioing.

In an independent variation, the ACPP can incorporate a ligand for a receptor that is preferably associated closely with the enzyme that cleaves the ACPP linker. This ligand pre-concentrates the ACPP in the immediate vicinity of the enzyme and thus increases the rapidity and specificity of cleavage.

The invention provides compounds that can be used as fluorescent probes. In one aspect, the invention provides a compound having the structure:

PAP-CL-PCP wherein PAP is a polyanionic peptide comprising a fluorescence acceptor, CL is a cleavable linker and PCP is a polycationic peptide comprising a fluorescence donor comprising a cyanine.

II. Definitions

The articles "a," "an" and "the" as used herein do not exclude a plural number of the referent, unless context clearly dictates otherwise. The conjunction "or" is not mutually exclusive, unless context clearly dictates otherwise. The term "include" refers to non-exhaustive examples.

The term "peptide" can refer to two or more amino acids joined by at least one peptide bond. The constituent amino acids can be any combination of D- and L-isomers.

A "polyanionic peptide" refers to a polypeptide comprising two or more anionic amino acids, i.e., amino acids having negatively charged sidechains. Preferably, a polyanionic peptide has 6, 7, 8, 9, 10, 11, 12 or 13 anionic amino acids. In exemplary embodiments, the anionic amino acids are contiguous. In exemplary embodiments, the polyanionic peptide comprises 9 glutamate residues.

A "polycationic peptide" refers to a polypeptide comprising two or more cationic amino acids, i.e., amino acids having positively charged sidechains. Preferably, a polycationic peptide has 6, 7, 8, 9, 10, 11, 12 or 13 cationic amino acids. In exemplary embodiments, the cationic amino acids are contiguous. In exemplary embodiments, the polyanionic peptide comprises nine arginine residues.

A polyanionic peptide, a polycationic peptide or a cleavable linker optionally includes one or more "derivatized amino acids", which are amino acids that comprise either (a) a targeting linker and a targeting moiety or (b) a fluorophore. In exemplary embodiments, a derivatized amino acid is attached to the N or C terminus of the polyanionic peptide, polycationic peptide or cleavable linker. In exemplary embodiments, a derivatized amino acid is cysteine. Examples include compounds wherein a polyanionic peptide is given by $PAP^1$-$D^1$ and a polycationic peptide is given by $PCP^2$-$D^2$ wherein $PAP^1$ is a sequence of contiguous anionic amino acids, $D^1$ is an amino acid (such as cys) that is attached to a targeting linker and a targeting moiety, $PCP^2$ is a sequence of contiguous cationic amino acids and $D^2$ is an amino acid (such as cys) that is attached to a fluorophore, such as a fluorescence donor.

In some embodiments, the compound comprises a targeting moiety. A targeting moiety is also referred to as a "ligand" herein. The targeting moiety is any moiety serves to target or direct the molecule to which it is attached to a particular tissue or cellular location or molecule. For example, a targeting moiety may be used to target a molecule to a specific target protein or enzyme, or to a particular cellular location, to a particular cell type or to a diseased tissue. As will be appreciated by those in the art, the localization of proteins within a cell is a simple method for increasing effective concentration. For example, shuttling an imaging agent and/or therapeutic into the nucleus confines them to a smaller space thereby increasing concentration. Finally, the physiological target may simply be localized to a specific compartment, and the agents must be localized appropriately.

The targeting moiety can be a small molecule (e.g., MW<500D), which includes both non-peptides and peptides. Examples of a targeting moiety also include amino acids, peptides, polypeptides (including proteins), nucleic acids (e.g., aptamers), oligonucleotides, carbohydrates, lipids, hormones, growth factors, lectins, receptors, receptor ligands, cofactors and the like. Targets of a targeting moiety can include a complementary nucleic acid, a receptor, an antibody, an antigen or a lectin, for example.

In exemplary embodiments, a targeting moiety binds to a receptor, such as integrin. In exemplary embodiments, a targeting moiety is a peptide. In exemplary embodiments, a targeting moiety has a sequence given in FIG. 3, wherein the targeting moiety is referred to as a targeting ligand or a ligand.

In exemplary embodiments, a targeting moiety can bind to a target with high binding affinity. In other words, a targeting moiety with high binding affinity to a target has a high specificity for or specifically binds to the target. In some embodiments, a high binding affinity is given by a dissociation constant $K_d$ of about $10^{-7}$ M or less. In exemplary embodiments, a high binding affinity is given by a dissociation constant $K_d$ of about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less or about $10^{-15}$ M or less. A compound may have a high binding affinity for a target if the compound comprises a portion, such as a targeting moiety, that has a high binding affinity for the target.

A "targeting linker" refers to any moiety useful for attaching a targeting moiety to another molecule, such as the compounds disclosed herein. Examples of a targeting linker include 0-order linkers (i.e., a bond), substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Further exemplary targeting linkers include substituted or unsubstituted ($C_1$, $C_2$, $C_3$, $C_4$, $C_5$, $C_6$, $C_7$, $C_8$, $C_9$ or $C_{10}$)alkyl, substituted or unsubstituted heteroalkyl, —C(O)NR'—, —C(O)O—, —C(O)S—, and —C(O)CR'R", wherein R' and R" are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, a targeting linker includes at least one heteroatom. Exemplary linkers also include —C(O)NH—, —C(O), —NH—, —S—, —O—, and the like.

In some embodiments, the targeting linker is a solubilizing moiety. A typical solubilizing moiety is hydrophilic and allows increased solubilization of the compound to which it is attached. Examples include linear or branched hydrophilic moieties comprising at least one polymeric moiety. In another example, a targeting linker is selected from poly (alkylene oxides) (i.e., polyethers), polyalcohols, polysaccharides (e.g., polysialic acid), polyamino acids (e.g., polyglutamic acid, polylysine), polyphosphoric acids, polyamines and derivatives thereof. Exemplary poly(alkylene oxides) include polyethylene glycol (PEG) and polypropylene glycol (PPG). PEG derivatives include those, in which the terminal hydroxyl group is replaced with another moiety, such as an alkyl group (e.g., methyl, ethyl or propyl). In one example, the hydrophilic moiety is methyl-PEG (mPEG).

In exemplary embodiments, the targeting linker is poly (ethyleneglycol). Both linear and branched PEG moieties can be used as the targeting linker. In an exemplary embodiment, PEG has between 1000 and 5000 subunits. In an exemplary embodiment, PEG has between 100 and 500 subunits. In an exemplary embodiment, PEG has between 10 and 50 subunits. In an exemplary embodiment, PEG has between 1 and 25 subunits. In an exemplary embodiment, PEG has between 15 and 25 subunits. In an exemplary embodiment, PEG has between 5 and 100 subunits. In an exemplary embodiment, PEG has between 1 and 500 subunits.

A "cleavable linker" is any moiety that can be hydrolyzed or radicalized. A "cleavable linker" is also sometimes referred to herein as a "substrate" according to context. Examples include peptides, polypeptides (including proteins), nucleic acids, oligonucleotides, carbohydrates, lipids, hormones, growth factors, lectins, receptors, receptor ligands, cofactors and the like. In exemplary embodiments, a cleavable linker is a substrate of an enzyme that is capable of cleaving the substrate. Exemplary enzymes include an MMP, such as MMP-9 or MMP-2, elastases, and thrombin. In exemplary embodiments, the cleavable linker is a polypeptide. A cleavable linker may optionally include a spacer between the cleavable linker and the rest of the compound to which it is attached. Thus, one example is the peptide (SEQ ID NO:5) oPLGC(Me)AG, which is cleaved by MMP-9, wherein o is 5-amino-3-oxopentanoyl, a short hydrophilic spacer.

The term "fluorescence donor" is any compound that emits photons through a fluorescence mechanism. A "fluorescence acceptor" refers to any compound that absorbs photons, such as those emitted by a fluorescence donor. In some embodiments, a fluorescence acceptor may also act as a fluorescence donor. In some embodiments, a fluorescence acceptor is nonfluorescent. Examples include quenchers such as a nitrophenyl moiety.

In some embodiments, a fluorescence donor and/or fluorescence acceptor is a cyanine. The term "cyanine" refers to a structure according to Formula I that is attached to a compound of the invention:

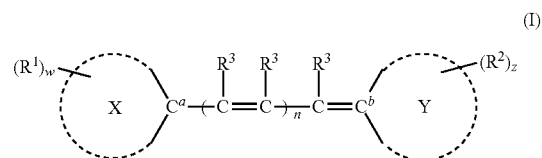

(I)

wherein the dotted lines encircling X and Y are each independently selected from atoms necessary for the formation of one ring to three fused rings having 4 to 7 atoms in each ring. At least one atom in the ring comprising $C^a$ is a nitrogen, and at least at least one atom in the ring comprising $C^b$ is a nitrogen. The indices w and z are integers independently selected from 0 to the number of atoms necessary for the formation of X or Y, with the proviso that w and z cannot both be 0. Each $R^3$ is a member independently selected from H, $OR^{30}$, $SR^{30}$, $NR^{30}R^{30}$, halogen, CN, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Two $R^3$ groups, together with the atoms to which they are attached, can be optionally joined to form a ring. The index n is an integer selected from 0 to 4. $R^1$ and $R^2$ are members independently selected from $R^1$ and $R^2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, $SO_3$, $NO_2$, CN, $P(O)(OR^4)(OR^5)$, $D^1R^6$, $NR^7R^8$ and $C(D^2)R^9$. $D^1$ is a member selected from O and S. $D^2$ is a member selected from O, S and NH. $R^4$ and $R^5$ are members independently selected from H, substituted or unsubstituted $C_1$-$C_4$ alkyl, substituted or unsubstituted $C_1$-$C_4$ heteroalkyl. At least one of $R^4$ and $R^5$ is H. $R^6$, $R^7$ and $R^8$ are members independently selected from H, substituted or unsubstituted alkyl and substituted or unsubstituted heteroalkyl. $R^7$ and $R^8$, together with the nitrogen to which they are attached, can be optionally joined to form a member selected from a reactive functional group, $-NHNH_2$, $-N=N=N$, $-N=C=S$ and $-N=C=O$. $R^9$ is a member selected from H, substituted or unsubstituted alkyl, substituted or unsubstituted heteroalkyl, a reactive functional group, $NR^{10}R^{11}$ and $OR^{12}$. $R^{16}$ and $R^{11}$ are members independently selected from H, substituted or unsubstituted alkyl and substituted or unsubstituted heteroalkyl. $R^{12}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and $C(O)R^{13}$. $R^{13}$ is a member selected from substituted or unsubstituted alkyl and substituted or unsubstituted heteroalkyl. Each $R^{30}$ is independently selected from H, a negative charge and a salt counterion.

In some embodiments, at least one $R^1$ and at least one $R^2$ are each $SO_3$.

In a one embodiment, $-(C(R^3)=C(R^3))_n-C(R^3)=$ is a member selected from:

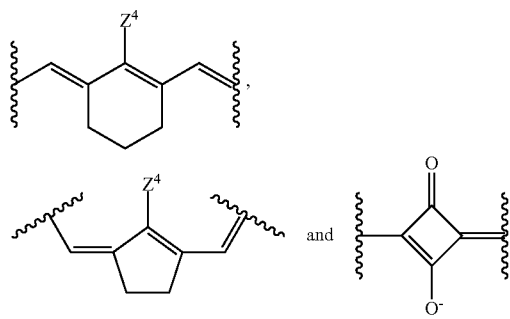

wherein $Z^4$ is a member selected from H, $OR^{30}$, $SR^{30}$, $NR^{30}R^{30}$, halogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In exemplary embodiments, $Z^4$ is H.

Additional cyanines that can be attached to the polypeptides disclosed herein are provided by US/2007/0021621 A1, without the requirement that the X and Y rings be substituted with $-P(O)(OH)(OH)$ or an ion thereof. In some embodiments, the X and Y rings are substituted by $SO_3$.

The term "alkyl", by itself or as part of another substituent, means a straight or branched chain hydrocarbon radical, which may be fully saturated, mono- or polyunsaturated. For convenience, the term alkyl may refer to divalent (i.e., alkylene) and other multivalent radicals in addition to monovalent radicals. Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like. An unsaturated alkyl group is one having one or more double bonds or triple bonds (i.e., alkenyl and alkynyl moieties). Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

Typically, an alkyl (or alkylene) group will have from 1 to 30 carbon atoms, That is, in some embodiments, alkyl refers to an alkyl having a number of carbons selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$ and any combination thereof. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroalkyl", by itself or in combination with another term, means an alkyl in which at least one carbon is replaced with an atom other than carbon (i.e., a heteroatom). In some embodiments, the heteroatom is selected from O, N and S, wherein the nitrogen and sulfur atoms may optionally be oxidized and the nitrogen heteroatom may optionally be quaternized. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N and S. The heteroatoms O, N and S may be placed at any interior position of the heteroalkyl group and may also be the position at which the heteroalkyl group is attached to the remainder of the molecule. In some embodiments, depending on whether a heteroatom terminates a chain or is in an interior position, the heteroatom may be bonded to one or more H or $C_1$, $C_2$, $C_3$, $C_4$, $C_5$ or $C_6$ alkyl according to the valence of the heteroatom. Examples include $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH=CH-O-CH_3$, $-CH_2-CH=N-OCH_3$, and $-CH=CH-N(CH_3)-CH_3$. Up to two heteroatoms may be consecutive, such as, for example, $-CH_2-NH-OCH_3$. The term "heteroalkylene" may be use to refer a divalent radical derived from heteroalkyl. Unless otherwise stated, no orientation of the linking group is implied by the direction in which a divalent group is written. For example, the formula $-C(O)_2R'-$ represents both $-C(O)_2R'-$ and $-R'C(O)_2-$.

The terms "cycloalkyl" and "heterocycloalkyl", by themselves or in combination with other terms refer to cyclic versions of "alkyl" and "heteroalkyl", respectively. For heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl and the like.

The terms "halo" or "halogen" refer to fluorine, chlorine, bromine and iodine. Additionally, terms such as "haloalkyl," are meant to include monohaloalkyl and polyhaloalkyl.

The term "aryl" refers to a polyunsaturated, aromatic hydrocarbon that can be a single ring or multiple rings (preferably 1, 2 or 3 rings) that are fused together or linked covalently. For convenience, the term aryl may refer to divalent (i.e., arylene) and other multivalent radicals in addition to monovalent radicals. In some embodiments, aryl is a 3, 4, 5, 6, 7 or 8 membered ring that is optionally fused to one or two other 3, 4, 5, 6, 7 or 8 membered rings.

The term "heteroaryl" refers to aryl containing 1, 2, 3 or 4 heteroatoms selected from N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

In some embodiments, any alkyl, heteroalkyl, cycloalkyl, heterocycloalkyl, aryl and heteroaryl may be substituted. Preferred substituents for each type of radical are provided below.

Substituents for alkyl, heteroalkyl, cycloalkyl and heterocycloalkyl radicals (including those groups often referred to as alkylene, alkenyl, heteroalkylene, heteroalkenyl, alkynyl, cycloalkenyl, and heterocycloalkenyl) are generically referred to as "alkyl group substituents". In some embodiments, an alkyl group substituent is selected from —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR'", —S(O)R', —S(O)$_2$R', —S(O)$_2$NR'R", —NRSO$_2$R', —CN and —NO$_2$. Embodiments of R', R", R'" and R"" are provided below. Substituents for aryl and heteroaryl groups are generically referred to as "aryl group substituents". In some embodiments, an aryl group substituent is selected from —R', —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR'", —S(O)R', —S(O)$_2$R', —S(O)$_2$NR'R", —NRSO$_2$R', —CN, —NO$_2$ and —N$_3$. In some embodiments, R', R", R'" and R"" are each independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In some embodiments, R', R", R'" and R"" are each independently selected from hydrogen, unsubstituted alkyl, unsubstituted heteroalkyl, unsubstituted cycloalkyl, unsubstituted heterocycloalkyl, unsubstituted aryl and unsubstituted heteroaryl. In some embodiments, R', R", R'" and R"" are each independently selected from hydrogen and unsubstituted alkyl (e.g., $C_1$, $C_2$, $C_3$, $C_4$, $C_5$ and $C_6$ alkyl).

Two substituents on adjacent atoms of an aryl or heteroaryl ring may optionally be replaced with a substituent of the formula -T-C(O)—(CRR')$_q$—U—, wherein T and U are independently selected from —NR—, —O—, —CRR'— and a single bond, and q is an integer selected from 0, 1, 2 and 3. Alternatively, two of the substituents on adjacent atoms of an aryl or heteroaryl ring may optionally be replaced with a substituent of the formula -A-(CH$_2$)$_r$—B—, wherein A and B are independently selected from CRR'—, —O—, —NR—, —S—, —S(O)—, —S(O)$_2$—, —S(O)$_2$NR'— and a single bond, and r is an integer selected from 1, 2, 3 and 4. One of the single bonds of the new ring so formed may optionally be replaced with a double bond. Alternatively, two of the substituents on adjacent atoms of the aryl or heteroaryl ring may optionally be replaced with a substituent of the formula —(CRR'), —X—(CR"R'")$_d$—, where s and d are independently integers selected from 0, 1, 2 and 3, and X is selected from —O—, —NR'—, —S—, —S(O)—, —S(O)$_2$— and —S(O)$_2$NR'—. The substituents R, R', R" and R'" are preferably independently selected from hydrogen and substituted or unsubstituted ($C_1$-$C_6$)alkyl.

Unless otherwise specified, the symbol "R" along with any superscript is a general abbreviation that represents a substituent group that is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound includes more than one R, R', R", R' and R"" group, they are each independently selected.

For groups with exchangeable or acidic protons, the ionized form is equally contemplated. For example, —COOH also refers to —COO$^-$ while —SO$_3$H also refers to —SO$_3^-$.

"Ring" as used herein means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. The ring optionally included a heteroatom. Thus, the term "5- to 7-membered ring" includes, for example pyridinyl and piperidinyl.

The terms cell penetrating peptide (CPP), membrane translocating sequence (MTS) and protein transduction domain are used interchangeably. As used herein, the terms mean a peptide (polypeptide or protein) sequence that is able to translocate across the plasma membrane of a cell. In some embodiments, a CPP facilitates the translocation of an extracellular molecule across the plasma membrane of a cell. In some embodiments, the CPP translocates across the plasma membrane by direct penetration of the plasma membrane, endocytosis-mediated entry, or the formation of a transitory structure The terms "polypeptide," "peptide" and "protein" are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds. As used herein, the terms "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a β-ester, a thioamide, phosphonamide, carbamate, hydroxylate, and the like (see, e.g., Spatola, (1983) Chem. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be either D amino acids or L amino acids. In peptide sequences throughout the specification, lower case letters indicate the D isomer of the amino acid (conversely, upper case letters indicate the L isomer of the amino acid).

In some embodiments, a FRET-ACPP substrate includes one or more non-standard amino acids, for example, hydroxylysine, desmosine, isodesmosine, and/or phosphoserine. In some embodiments, a FRET-ACPP substrate includes one or more modified amino acids, including post-translationally modified amino acids. Non-limiting examples of modified amino acids include methylated amino acids (e.g., methyl histidine, methylated forms of lysine), acetylated amino acids, amidated amino acids, formylated amino acids, hydroxylated amino acids, phosphorylated amino acids, or other modified amino acids. In some embodiments, a FRET-ACPP substrate includes one or more peptide mimetic moieties, including portions linked by non-peptide bonds and amino acids linked by or to non-amino acid portions. Non-limiting examples of peptide mimetics include peptoids, carbamates, vinyl polymers, or other molecules having non-peptide linkages but having an acidic portion cleavably linked to a basic portion having a cargo moiety.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "administer," "administering", "administration," and the like, as used herein, refer to the methods that may be used to enable delivery of agents or compositions to the desired site of biological action. These methods include, but are not limited to parenteral injection (e.g., intravenous, subcutaneous, intraperitoneal, intramuscular, intravascular, intrathecal, intravitreal, infusion, or local). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "surgery" as used herein, refers to any methods for that may be used to manipulate, change, or cause an effect by a physical intervention. These methods include, but are not limited to open surgery, endoscopic surgery, laparoscopic surgery, minimally invasive surgery, and robotic surgery.

The following symbols, where used, are used with the indicated meanings: Fl=fluorescein; aca=ahx=X=aminocaproic acid linker (—HN—(CH$_2$)$_5$—CO—); C=L-cysteine; E=L-glutamate; R=L-arginine; D=L-aspartate; K=L-lysine; A=L-alanine; r=D-arginine; c=D-cysteine; e=D-glutamate; P=L-proline; L=L-leucine; G=glycine; V=valine; I=isoleucine; M=methionine; F=phenylalanine; Y=tyrosine; W=tryptophan; H=histidine; Q=glutamine; N=asparagine; S=serine; and T=threonine.

III. Cyanine Fluorophores

Exemplary cyanines include Cy5 and Cy7, which are general classes of cyanines.

In exemplary embodiments, Cy7 is attached to the N-terminus of the compound of the invention and Cy5 is attached to a derivatized amino acid, such as a derivatized cysteine. For example, Cy7 can be attached to the N-terminus of a polyanionic peptide.

In some embodiments, a fluorescence donor is attached to a compound of the invention by synthesizing the compound of the invention with Cy5-maleimide.

In exemplary embodiments, Cy5-maleimide has the structure:

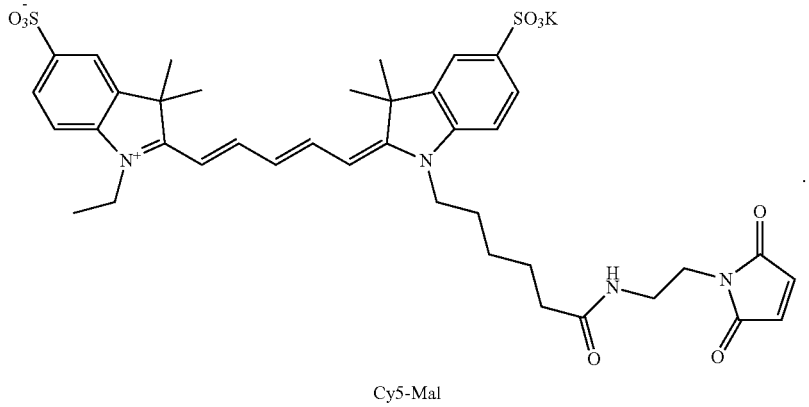

Cy5-Mal

In exemplary embodiments, the fluorescence donor is Cy5 having the structure

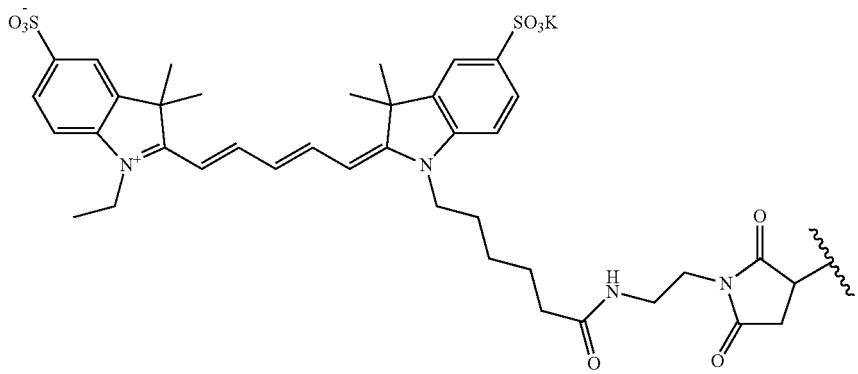

In some embodiments, a fluorescence acceptor is attached to a compound of the invention by synthesizing the compound of the invention with Cy7-NHS.

In exemplary embodiments, Cy7-NHS has the structure:

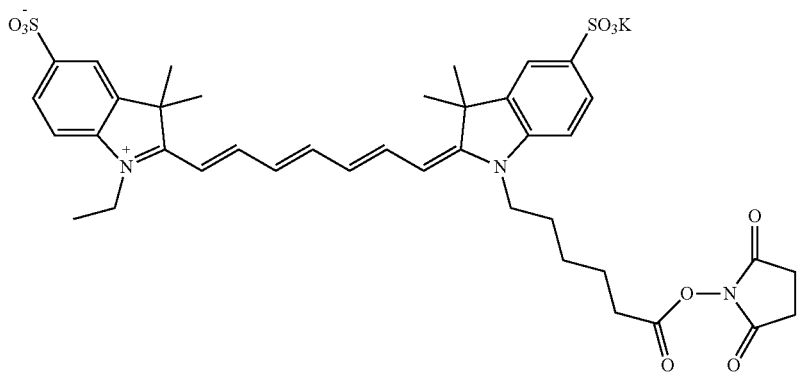

Cy7-NHS

In exemplary embodiments, the fluorescence acceptor is Cy7 having the structure

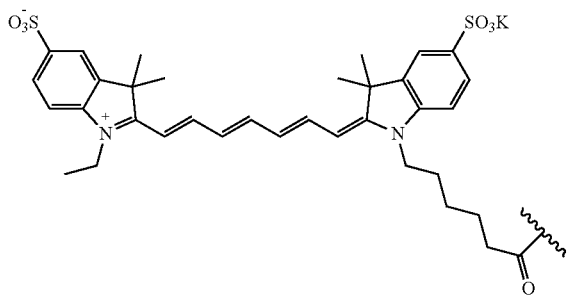

Figure 3:
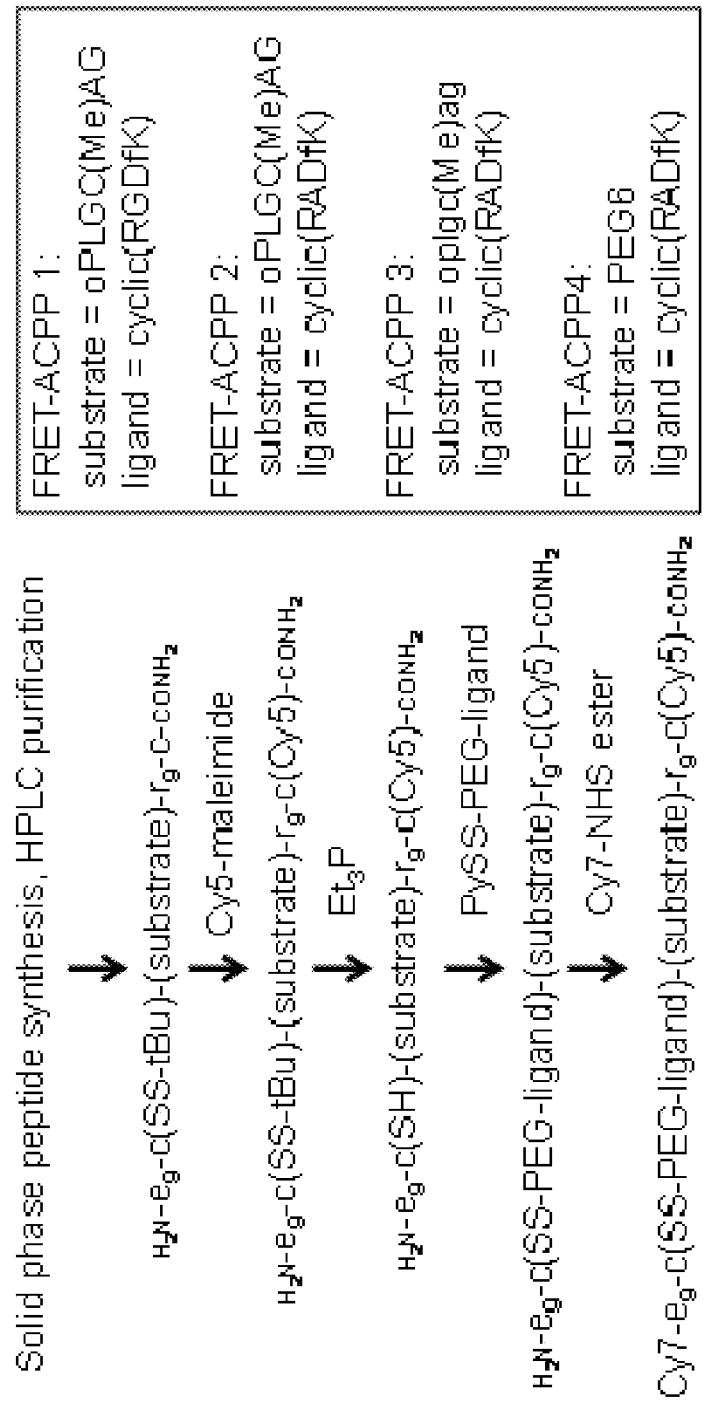
FIG. 3 illustrates a method for the synthesis of FRET-ACPPs, in one embodiment.

In exemplary embodiments, the compound has a structure selected from those shown in FIG. 3.

IV. Ratiometric Activatable Cell Penetrating Peptides (RACPPs)

The present disclosure is based in part on the finding that the cellular uptake of polycationic molecules with multiple basic amino acids can be inhibited by the addition of a portion having multiple negative charges at physiological pH, such as a peptide portion having multiple acidic amino acids. Thus, an embodiment of the invention provides compounds including a peptide portion A of between about 2 to about 20 acidic amino acids linked by a cleavable linker X to a peptide portion B of between about 5 to about 20 basic amino acids, so that while the peptide portion A is linked to the peptide portion B, uptake of the molecule into cells is inhibited or prevented. The acidic portion A may include some amino acids that are not acidic amino acids, or other moieties as well. Similarly, the basic portion B may include some amino acids that are not basic amino acids, or other moieties as well. After cleavage of linker X so that peptide portion A may separate from the peptide portion B. Portion B is subsequently able to enter a cell, the inhibition due to portion A having been removed. The cleavable linker X is preferably cleavable under physiological conditions.

In one aspect, the present disclosure provides a compound having the structure:

PAP-CL-PCP wherein: PAP is a polyanionic peptide comprising a fluorescence acceptor; CL is a first linker, wherein the first linker is cleavable; and PCP is a polycationic peptide comprising a fluorescence donor. In some embodiments, the compound has an optional targeting moiety attached via an optional second linker. In some embodiments, either or both of the fluorescence acceptor and donor are cyanines.

Disclosed herein, in certain embodiments, is a molecule of the structure T-X$^1$—(C-A-X$^2$—B-D), wherein: C is an acceptor fluorophore; A is a peptide with a sequence comprising 5 to 9 consecutive acidic amino acids selected from aspartates and glutamates; X$^2$ is a cleavable linker; B is a peptide with a sequence comprising 5 to 20 consecutive basic amino acids; D is a donor fluorophore capable of participating in FRET with acceptor fluorophore C; X$^1$ is an optional linker; and T is an optional targeting agent, wherein X$^1$ is bound to A.

Acceptor Fluorophore (C)

In some embodiments, C/fluorescence acceptor is a fluorescent moiety, such as a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. No. 4,452,720, U.S. Pat. No. 5,227,487, and U.S. Pat. No. 5,543,295, the contents of which are hereby expressly incorporated by reference in their entireties for all purposes.

In some embodiments, C/fluorescence acceptor is a fluorescein dye. Non-limiting examples of fluorescein dyes include 5-carboxyfluorescein, fluorescein-5-isothiocyanate and 6-carboxyfluorescein; examples of other fluorescein dyes can be found, for example, in U.S. Pat. No. 6,008,379, U.S. Pat. No. 5,750,409, U.S. Pat. No. 5,066,580, and U.S. Pat. No. 4,439,356, the contents of which are hereby expressly incorporated by reference in their entireties for all purposes. In some embodiments, C/fluorescence acceptor and/or D/fluorescence donor are rhodamine dyes. Non-limiting examples of rhodamine dyes include tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the trade name of TEXAS RED®). Other rhodamine dyes can be found, for example, in U.S. Pat. No. 6,080,852, U.S. Pat. No. 6,025,505, U.S. Pat. No. 5,936,087, U.S. Pat. No. 5,750,409, the contents of which are hereby expressly incorporated by reference in their entireties for all purposes.

In some embodiments, C/fluorescence acceptor is a cyanine. Non-limiting examples of cyanine dyes include Cy3, Cy3B, Cy3.5, Cy5, Cy5.5, Cy 7. In some embodiments, C is a fluorophore of structure (I):

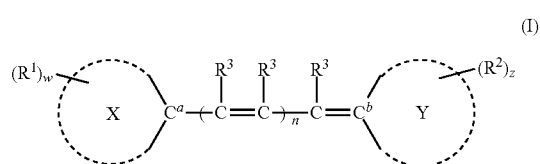

(I)

wherein the dotted lines encircling X and Y are each independently selected from atoms necessary for the formation of one ring to three fused rings having 4 to 7 atoms in each ring; at least one atom in the ring comprising C$^a$ is a nitrogen; at least one atom in the ring comprising C$^b$ is a nitrogen; the indices w and z are integers independently selected from 0 to the number of atoms necessary for the formation of X or Y, with the proviso that w and z cannot both be 0; each R$^3$ is a member independently selected from H, OR$^{30}$, SR$^{30}$, NR$^{30}$R$^{30}$, halogen, CN, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; two R$^3$ groups, together with the atoms to which they are attached, can be optionally joined to form a ring; the index n is an integer selected from 0, 1, 2, 3 and 4; R$^1$ and R$^2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, $SO_3$, $NO_2$, CN, P(O)(OR$^4$)(OR$^5$), D$^1$R$^6$, NR$^7$R$^8$ and C(D$^2$)R$^9$; D$^1$ is a member selected from O and S; D$^2$ is a member selected from O, S and NH; R$^4$ and R$^5$ are members independently selected from H, substituted or unsubstituted C$_1$-C$_4$ alkyl, substituted or unsubstituted C$_1$-C$_4$ heteroalkyl; at least one of R$^4$ and R$^5$ is H; R$^6$, R$^7$ and R$^8$ are members independently selected from H, substituted or unsubstituted alkyl and substituted or unsubstituted heteroalkyl; R$^7$ and R$^8$, together with the nitrogen to which they are attached, can be optionally joined to form a member selected from a reactive functional group, —NHNH$_2$, —N=N=N, —N=C=S and —N=C=O; R$^9$ is a member selected from H, substituted or unsubstituted alkyl, substituted or unsubstituted heteroalkyl, a reactive functional group, NR$^{10}$R$^{11}$ and OR$^{12}$; R$^{10}$ and R$^{11}$ are members independently selected from H, substituted or unsubstituted alkyl and substituted or unsubstituted heteroalkyl; R$^{12}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and C(O)R$^{13}$; R$^{13}$ is a member selected from substituted or unsubstituted alkyl and substituted or unsubstituted heteroalkyl; and each R$^{30}$ is independently selected from H, a negative charge and a salt counterion.

In some embodiments, C/fluorescence acceptor is Cy5, Cy5.5, Cy7, IRDYE 800CW, or ALEXA647. In a specific embodiment, C is Cy7.

Polyanionic Peptide (A)

In some embodiments, A/polyanionic peptide has a sequence comprising 4 to 20, or any intermediate range thereof, consecutive acidic amino acids. In one embodiment, A comprises from 5 to 9 consecutive acidic amino acids. In one embodiment, an acidic amino acid is negatively charged at pH 6.0. In one embodiment, an acidic amino acid has a side chain with a pKa of less than 6.0. Non-limiting examples of acid amino acids include aspartic acid, glutamic acid, phosphoserine, and phosphothreonine. In a specific embodiment, A comprises 5 to 9 consecutive glutamates, aspartates, or a mixture thereof. In some embodiments, A comprises one or more D-amino acids. In a specific embodiment, A consists of D-amino acids.

In some embodiments, A is 8 consecutive glutamates (i.e., EEEEEEEE, E$_8$, eeeeeeee, or e$_8$), B is nine consecutive arginines (i.e., RRRRRRRRR, R$_9$, rrrrrrrrr, or r$_9$).

In some embodiments, A includes non-standard amino acids, for example, hydroxylysine, desmosine, isodesmosine, or other non-standard amino acids. Portion A may include modified amino acids, including post-translationally modified amino acids for example, methylated amino acids (e.g., methyl histidine, methylated forms of lysine), acetylated amino acids, amidated amino acids, formylated amino acids, hydroxylated amino acids, phosphorylated amino acids, or other modified amino acids. Portion A may also include peptide mimetic moieties, including portions linked by non-peptide bonds and amino acids linked by or to non-amino acid portions.

Polycationic Peptide (B)

In some embodiments, B/polycationic peptide has a sequence comprising 5 to 20, or any intermediate range thereof, consecutive basic amino acids. In one embodiment, B comprises from 5 to 9 consecutive basic amino acids. In one embodiment, a basic amino acid is positively charged at pH 6.0. Non-limiting examples of basic amino acids include lysine, arginine, and histidine. In a specific embodiment, B comprises 5 to 9 consecutive lysines, arginines, histidine, or a mixture thereof. In some embodiments, B comprises one or more D-amino acids. In a specific embodiment, B consists of D-amino acids.

In some embodiments, B includes non-standard amino acids, for example, hydroxylysine, desmosine, isodesmosine, or other non-standard amino acids. Portion B may include modified amino acids, including post-translationally modified amino acids for example, methylated amino acids (e.g., methyl histidine, methylated forms of lysine), acetylated amino acids, amidated amino acids, formylated amino acids, hydroxylated amino acids, phosphorylated amino acids, or other modified amino acids. Portion A may also include peptide mimetic moieties, including portions linked by non-peptide bonds and amino acids linked by or to non-amino acid portions.

In some embodiments, A has a sequence comprising 8 to 9 consecutive glutamates and B has a sequence comprising 9 consecutive arginines. In some embodiments, A and B comprise D-amino acids.

Portions A and B may include either L-amino acids or D-amino acids. In certain embodiments, D-amino acids are preferred because they minimize immunogenicity and non-specific cleavage by background peptidases or proteases. Cellular uptake of oligo-D-arginine sequences is known to be as good, or better, than that of oligo-L-arginines.

The generic structures PAP-CL-PCP, PCP-CL-PAP, C-A-X$^2$—B-D, and D-B—X$^2$-A-C are equally effective. Accordingly, in certain embodiments, A can be positioned at either the amino- or carboxy-terminus. Similarly, in certain embodiments, B can be positioned at either the amino- or carboxy-terminus. In other embodiments, where X is a peptide cleavable by a protease, it may be preferable to join the C-terminus of X to the N-terminus of B, so that the new amino terminus created by cleavage of X contributes an additional positive charge that adds to the positive charges already present in B.

Cleavable linker (X$^2$/CL)

Cleavable linker X$^2$/CL serves to connect acidic portion A/polyanionic peptide with basic portion B/polycationic peptide. A cleavable linker X may include, for example, between about 2 to about 100 atoms, or between about 6 to about 30 atoms. Cleavable linker portion X may include amino acid residues and may be a peptide linkage of between about 1 to about 30, or between about 2 to about 10 amino acid residues. A cleavable linker X suitable for the practice of the invention may be a flexible linker. In preferred embodiments, a cleavable linker X suitable for the practice of the invention is a flexible linker, and may be about 6 to about 24 atoms in length. In embodiments of the invention, X may include a peptide linkage. In one embodiment, a cleavable linker X includes aminocaproic acid.

In some embodiments, X$^2$/CL is cleaved in the extracellular space. In some embodiments, X$^2$ is cleaved by a protease, a matrix metalloproteinase, or a combination thereof. In some embodiments, X$^2$ comprises a peptide having an amino acid sequence selected from: (SEQ ID NO:8) PLGLAG, (SEQ ID NO:9) PLGLA X wherein X is any amino acid, (SEQ ID NO:7) PLGC(me)AG, (SEQ ID NO:10) ESPAYYTA, and (SEQ ID NO:4) RLQLKL, (SEQ ID NO:11) RLQLK(AC), (SEQ ID NO:2) PPRSFL, and (SEQ ID NO:1) DPRSFL.

In some embodiments, linker X$^2$/CL may be designed for cleavage in the presence of particular conditions or in a particular environment. In preferred embodiments, X$^2$/CL is cleavable under physiological conditions. Cleavage of such a linker may, for example, be enhanced or may be effected by particular pathological signals or a particular environment related to cells in which cargo delivery is desired. The design of linker $X^2$/CL for cleavage by specific conditions, such as by a specific enzyme, allows the targeting of cellular uptake to a specific location where such conditions obtain. Thus, one important way that CPP molecules having features described herein provide specific targeting of cellular uptake to desired cells, tissues, or regions is by the design of the linker portion $X^2$/CL to be cleaved by conditions near such targeted cells, tissues, or regions. After cleavage of $X^2$/CL, the B-D portions of the molecule are liberated to form a simple conjugate of B and D. In some embodiments, activated conjugate B-D retains a relatively small, inert residual portion of linker $X^2$/CL.

In some embodiments, linker $X^2$/CL is cleavable by conditions found in the extracellular environment, such as acidic conditions which may be found near cancerous cells and tissues or a reducing environment, as may be found near hypoxic or ischemic cells and tissues; by proteases or other enzymes found on the surface of cells or released near cells having a condition to be treated, such as diseased, apoptotic or necrotic cells and tissues; or by other conditions or factors. An acid-labile linker may be, for example, a cis-aconitic acid linker. Other examples of pH-sensitive linkages include acetals, ketals, activated amides such as amides of 2,3-dimethylmaleamic acid, vinyl ether, other activated ethers and esters such as enol or silyl ethers or esters, imines, iminiums, enamines, carbamates, hydrazones, and other linkages.

In some embodiments, linker $X^2$/CL is an amino acid or a peptide. A peptide linker may be of any suitable length, such as, for example, about 3 to about 30, or preferably about 6 to about 24 atoms in sequence (e.g., a linear peptide about 1 to 10 or preferably about 2 to 8 amino acids long). In certain embodiments, the cleavable peptide linker includes an amino acid sequence recognized and cleaved by a protease, so that proteolytic action of the protease cleaves linker $X^2$/CL.

One important class of signals is the hydrolytic activity of matrix metalloproteinases (MMPs), which are very important in the invasive migration of metastatic tumor cells. MMPs are also believed to play major roles in inflammation and stroke. MMPs are reviewed in Visse et al., *Circ. Res.* 92:827-839 (2003). In some embodiments, linker $X^2$/CL contains a peptide sequence cleaved by an MMP protease (e.g., MMP-2 or MMP-9). Thus, in certain embodiments, imaging and uptake of the ACPP substrates described herein is directed at tissues and/or organs having active MMPs in the extracellular environment.

For example, in one embodiment, linker $X^2$/CL includes the amino-acid sequence (SEQ ID NO:8) PLGLAG, which may be cleaved by the metalloproteinase enzyme MMP-2 (a major MMP in cancer and inflammation). Cleavage of such a linker $X^2$/CL occurs between the central G and L residues, causing cell uptake to increase by 10 to 20-fold. A great deal is known about the substrate preferences of different MMPs, so that linkers $X^2$/CL may be designed to be preferentially sensitive to particular subclasses of MMPs, or to individual members of the large MMP family of proteinases. For example, in some embodiments, a linker $X^2$/CL is designed to be cleaved by membrane-anchored MMPs. In some embodiments, this is preferred because their activity remains localized to the outer surface of the expressing cell. In alternative embodiments, a linker $X^2$/CL is designed to be cleaved by a secreted MMP is preferred.

In some embodiments, cleavable linker $X^2$/CL includes a peptide cleavage sequence capable of being cleaved by an extracellular enzyme or physiological condition. Non-limiting examples of cleavage sequences suitable for use in a cleavable linker $X^2$/CL include: a sequence cleavable by MMP-9, for example, (SEQ ID NO:12) PR(S/T)(L/I)(S/T); a sequence cleavable by MMP-11, for example, (SEQ ID NO: 12) PR(S/T)(L/I)(S/T) or (SEQ ID NO: 13) GGAAN-LVRGG; a sequence cleavable by MMP-14, for example, (SEQ ID NO:14) SGRIGFLRTA; a sequence cleavable by urokinase plasminogen activator (uPA), for example, (SEQ ID NO: 15) SGRSA; a sequence cleavable by lysosomal enzymes, for example, (SEQ ID NO:16) GFLG, (SEQ ID NO:17) ALAL, or FK; a sequence cleavable by a cathepsin, for example, KK, RR, or both; a sequence cleavable by cathepsin D, for example, (SEQ ID NO: 18) PIC(Et)F-F, where C(Et) indicates S-ethylcysteine (a cysteine with an ethyl group attached to the thiol) and the "-" indicates the typical cleavage site in this and subsequent sequences; a sequence cleavable by cathepsin K, for example, (SEQ ID NO:19) GGPRGLPG, a sequence cleavable by prostate-specific antigen, for example (SEQ ID NO:20) HSSKLQ; a sequence cleavable by a herpes simplex virus protease, for example, (SEQ ID NO:21) LVLA-SSSFGY; a sequence cleavable by a HIV protease, for example, (SEQ ID NO:22) GVSQNY-PIVG; a sequence cleavable by a cytomegalovirus protease, for example, (SEQ ID NO:23) GVVQA-SCRLAa sequence cleavable by thrombin, for example, f(Pip)R-S, where "f" indicates D-phenylalanine and "Pip" indicates piperidine-2-carboxylic acid (pipecolinic acid, a proline analog having a six-membered ring); a sequence cleavable by caspase-3, for example, (SEQ ID NO:24) DEVD; a sequence cleavable by interleukin 1β converting enzyme, for example, (SEQ ID NO:25) GWEHD-G.

In some embodiments, linkers suitable for use in the imaging substrates described herein are cleavable by agents other than proteases, under physiological conditions. Linkers may also be non-peptide molecules. Non-limiting examples of enzymatically and non-enzymatically cleavable moieties suitable as linkers are illustrated in FIG. 16 of U.S. Patent Application Publication Number 2007/0041904, the content of which is hereby expressly incorporated by reference in its entirety for all purposes. Examples of different cleavable linkers are shown along with an indication of conditions which lead to cleavage. For example, cleavage of the linker labeled (a) may be accomplished by beta-lactamase. Cleavage of the linker labeled (b) may be accomplished by exposure to light, such as to a single photon of violet light or to two photons of infrared light. Cleavage of the linker labeled (c) may occur under reducing conditions. Cleavage of the linkers labeled (d) and (e) may occur in acidic conditions. Action of an esterase may cleave the linker labeled (f), and a phosphatase may cleave the linker labeled (g).

Hypoxia is an important pathological signal. For example, hypoxia is thought to cause cancer cells to become more resistant to radiation and chemotherapy, and also to initiate angiogenesis. In one embodiment, linker $X^2$/CL is designed to be cleaved at or near tissues suffering from hypoxia, enabling targeting of portion B and D to cancer cells and cancerous tissues, infarct regions, and other hypoxic regions. For example, in one embodiment, linker $X^2$/CL includes a disulfide bond that is preferentially cleaved in hypoxic regions, thus targeting cargo to cells in such a region. In a hypoxic environment, for example, leaky or necrotic cells, free thiols and other reducing agents become available extracellularly, while $O_2$ concentrations, which normally keeps the extracellular environment oxidizing, are depleted. This shift in the redox balance should promote reduction and cleavage of a disulfide bond within a linker X. In addition to disulfide linkages which take advantage of thiol-disulfide equilibria, linkages including quinones that fall apart when reduced to hydroquinones may be used in a linker $X^2$/CL designed to be cleaved in a hypoxic environment.

Necrosis often leads to release of enzymes or other cell contents that may be used to trigger cleavage of a linker $X^2$/CL. In some embodiments, linker $X^2$/CL is designed for cleavage in regions of necrosis in the absence of hypoxia, for example, by calpains or other proteases that may be released from necrotic cells. Such cleavage of linkers $X^2$/CL by calpains would release the connected portions B-D from portion A, allowing multispectral, ratiometric, and/or excitation lifetime imaging, as described herein, at or near diseased cells and tissues.

Acidosis is also commonly observed in sites of damaged or hypoxic tissue, due to the Warburg shift from oxidative phosphorylation to anaerobic glycolysis and lactic acid production. In some embodiments, this local acidity is sensed by using an imaging substrate having an acid-labile linker $X^2$/CL (e.g., by including an acetal or vinyl ether linkage). Alternatively, or in addition, acidosis may be used as a trigger of cargo uptake by replacing some of the arginines within B by histidines, which only become cationic below pH 7.

In some embodiments, an imaging substrate includes more than one linker $X^2$/CL so that polyanionic peptide A is linked to polycationic peptide B by more than one linkage. In some embodiments of an imaging substrate having more than one linker $X^2$/CL, separation of portion A from the other portions of the molecule requires cleavage of all linkages $X^2$/CL. Cleavage of multiple linkers $X^2$/CL may be simultaneous or sequential. In some embodiments, multiple linkages $X^2$/CL includes linkages $X^2$/CL having different specificities, so that separation of portion A from the other portions of the molecule requires that more than one condition or environment ("extracellular signals") be encountered by the imaging substrate. Cleavage of multiple linkers $X^2$/CL thus serves as a detector of combinations of such extracellular signals. FIG. 2D of U.S. Patent Application Serial Number 2007/0041904, the content of which is hereby expressly incorporated by reference in its entirety for all purposes, shows a MTS molecule that includes two cleavable linker portions, Xa and Xb, connecting basic portion B with acidic portion A. FIG. 2E of U.S. Patent Application Serial Number 2007/0041904 shows a cyclic substrate molecule that includes two linker regions, Xa and Xb, connecting basic portion B with acidic portion A. In the MTS molecules schematically illustrated in FIGS. 2D and 2E, both linkers, Xa and Xb, must be cleaved before acidic portion A is separated from basic portion B, allowing entry of portion B and cargo portion C (e.g., a fluorophore) to enter a cell. It will be understood that a linker region may link to either a basic portion B or a cargo portion C independently of another linker that may be present, and that, where desired, more than two linker regions X may be included.

Combinations of two or more cleavable linkers $X^2$/CL may be used to further modulate the targeting and delivery of molecules to desired cells, tissue, or regions of interest. Boolean combinations of extracellular signals can be detected to widen or narrow the specificity of the cleavage of linkers $X^2$/CL if desired. Where multiple linkers $X^2$/CL are linked in parallel, the specificity of cleavage is narrowed, since each linker $X^2$/CL must be cleaved before portion A may separate from the remainder of the molecule. Where multiple linkers $X^2$/CL are linked in series, the specificity of cleavage is broadened, since cleavage on any one linker $X^2$/CL allows separation of portion A from the remainder of the molecule. For example, in order to detect either a protease OR hypoxia (i.e., to cleave $X^2$/CL in the presence of either protease or hypoxia), a linker $X^2$/CL is designed to place the protease-sensitive and reduction-sensitive sites in tandem, so that cleavage of either would suffice to allow separation of the acidic portion A. Alternatively, in order to detect the presence of both a protease and hypoxia (i.e., to cleave $X^2$/CL in the presence of both protease and hypoxia but not in the presence of only one alone), a linker $X^2$/CL is designed to place the protease sensitive site between at least one pair of cysteines that are disulfide-bonded to each other. In that case, both protease cleavage and disulfide reduction are required in order to allow separation of portion A.

Donor Fluorophore (D)

In some embodiments, D/fluorescence donor is a fluorescent moiety, such as a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. No. 4,452,720, U.S. Pat. No. 5,227,487, and U.S. Pat. No. 5,543,295, the contents of which are hereby expressly incorporated by reference in their entireties for all purposes.

In some embodiments, D/fluorescence donor is a cyanine. Non-limiting examples of cyanine dyes include Cy3, Cy3B, Cy3.5, Cy5, Cy5.5, Cy 7. In some embodiments, D is a fluorophore of structure (I):

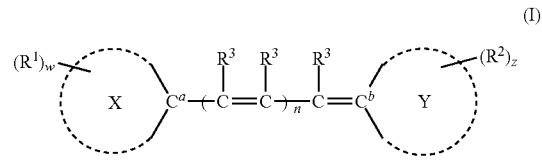

wherein the dotted lines encircling X and Y are each independently selected from atoms necessary for the formation of one ring to three fused rings having 4 to 7 atoms in each ring; at least one atom in the ring comprising $C^a$ is a nitrogen; at least one atom in the ring comprising $C^b$ is a nitrogen; the indices w and z are integers independently selected from 0 to the number of atoms necessary for the formation of X or Y, with the proviso that w and z cannot both be 0; each $R^3$ is a member independently selected from H, $OR^{30}$, $SR^{30}$, $NR^{30}R^{30}$, halogen, CN, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; two $R^3$ groups, together with the atoms to which they are attached, can be optionally joined to form a ring; the index n is an integer selected from 0, 1, 2, 3 and 4; $R^1$ and $R^2$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, $SO_3$, $NO_2$, CN, $P(O)(OR^4)(OR^5)$, $D^1R^6$, $NR^7R^8$ and $C(D^2)R^9$; $D^1$ is a member selected from O and S; $D^2$ is a member selected from O, S and NH; $R^4$ and $R^5$ are members independently selected from H, substituted or unsubstituted $C_1$-$C_4$ alkyl, substituted or unsubstituted $C_1$-$C_4$ heteroalkyl; at least one of $R^4$ and $R^5$ is H; $R^6$, $R^7$ and $R^8$ are members independently selected from H, substituted or unsubstituted alkyl and substituted or unsubstituted heteroalkyl; $R^7$ and $R^8$, together with the nitrogen to which they are attached, can be optionally joined to form a member selected from a reactive functional group, —$NHNH_2$, N=N=N, —N=C=S and N=C=O; $R^9$ is a member selected from H, substituted or unsubstituted alkyl, substituted or unsubstituted heteroalkyl, a reactive functional group, $NR^{10}R^{11}$ and $OR^{12}$; $R^{10}$ and $R^{11}$ are members independently selected from H, substituted or unsubstituted alkyl and substituted or unsubstituted heteroalkyl; $R^{12}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and $C(O)R^{13}$; $R^{13}$ is a member selected from substituted or unsubstituted alkyl and substituted or unsubstituted heteroalkyl; and each $R^{30}$ is independently selected from H, a negative charge and a salt counterion.

In some embodiments, D/fluorescence donor is Cy5, Cy5.5, Cy7, IRDYE 800CW, or ALEXA647. In a specific embodiment, C is Cy5.

Optional Linker ($X^1$)

In some embodiments, $X^1$/optional second linker comprises a water soluble polymer. In some embodiments, $X^1$ comprises a PEG. In some embodiments, $X^1$ comprises a $PEG_3$-$PEG_{24}$. In a specific embodiment, $X^1$ comprises a $PEG_{12}$.

Optional Targeting Moiety (T)

In some embodiments, T/optional targeting moiety is a targeting agent that binds to a cancer cell surface antigen. In one embodiment, T is a targeting agent that binds to an antigen selected from the group consisting of 5 alpha reductase, α-fetoprotein, AM-1, APC, APRIL, BAGE, β-catenin, Bc12, bcr-abl (b3a2), CA-125, CASP-8/FLICE, Cathepsins, CD19, $CD_2O$, CD21, CD23, CD22, CD38, CD33, CD35, CD44, CD45, CD46, CDS, CD52, CD55, CD59 (791Tgp72), CDC27, CDK4, CEA, c-myc, Cox-2, DCC, DcR3, E6/E7, EGFR, EMBP, Ena78, FGF8b and FGF8a, FLK-1/KDR, Folic Acid Receptor, G250, GAGE-Family, gastrin 17, GD2/GD3/GM2, GnRH, GnTV, gp100/Pme117, gp-100-in4, gp15, gp75/TRP-1, hCG, Heparanase, Her2/neu, HER3, Her4, HMTV, HLA-DR10, Hsp70, hTERT, IGFR1, IL-13R, iNOS, Ki 67, KIAA0205, K-ras, H-ras, N-ras, KSA, (CO17-1A), LDLR-FUT, MAGE Family (MAGE1, MAGE3, etc.), Mammaglobin, MAP17, Melan-A/, MART-1, mesothelin, MIC A/B, MT-MMP's, such as MMP2, MMP3, MMPI, MMP9, Moxl, MUC-1, MUC-2, MUC-3, and MUC-4, MUM-1, NY-ESO-1, Osteonectin, p15, P170/MDR1, p53, p97/melanotransferrin, PAI-1, PDGF, Plasminogen (uPA), PRAME, Probasin, Progenipoietin, PSA, PSM, RAGE-1, Rb, RCAS1, SART-1, SSX gene, family, STAT3, STn, TAG-72, TGF-α, TGF-β, and Thymosin β15, nucleolin, Ca15-3, astro Intestinal Tumor Antigen (Ca19-9), ovarian Tumor Antigen (Ca125), Tag72-4 Antigen (CA72-4) and carcinoembryonic antigen (CEA). In some embodiments, T is a cyclo-RGD or cyclo-RGDfK peptide.

Exemplary Peptide Substrates

In some embodiments, the compound is selected from the compounds shown in FIGS. 14 and 27.

In some embodiments, the core imaging substrate (i.e., A-$X^2$-B) has any one of a number of combinations of basic amino acids, acidic amino acids, and linkers. In addition to these core structure, in some embodiments, C- and D- are attached to A and B, respectfully, through a cysteine residue attached to the ends of the core structure. Non-limiting examples of the A-$X^2$-B core structure include:

EDA-aca-$R_5$ (SEQ ID NO: 26)

EDDDDKA-aca-$R_6$ (SEQ ID NO: 27)

EEEDDDEEEDA-aca-$R_9$ (SEQ ID NO: 28)

ededdAAeeeDDDDKA-aca-$R_{11}$ eddededeDDDDKA-aca-$R_6$-AGA-$R_6$

Ggedgddeeeeeeddeed-aca-PLGLAG-aca-$R_8$-AAA-$R_{12}$ eeddeeddKA-aca-$R_7$ eDDDDKA-aca-RGRGRRR eddddeeeeeee-aca-PLGLAGKA-aca-$R_{10}$ eeeeeeeeeeeeeeee-aca-DDDDKA-aca-$R_{20}$ eeeeeeeeeddddd-aca-DDDKA-aca-$R_{17}$ dddddddddddddddd-aca-PLGLAG-aca-$R_{14}$ EDDDDKA-aca-$R_9$ (SEQ ID NO: 29)

RRRRRRRRR-aca-EEEEEEEE (SEQ ID NO: 30)

EEE-aca-RRRRRRRRR (SEQ ID NO: 31)

EEEEEDDDKA-aca-RRRRRRRRR (SEQ ID NO: 32)

EDDDDKA-aca-RRRRRRRRR (SEQ ID NO: 33)

EEEEEDDDKARRRRRRRRR (SEQ ID NO: 34)

EEDDDDKA-aca-rrrrrrrr

DDDDDDKARRRRRRRRR (SEQ ID NO: 35)

EEDDDDKAR-aca-RR-aca-RR-aca-RR-aca-RR (SEQ ID NO: 36)

eeeeee-aca-PLGLAG-rrrrrrrrr

EDA-aca-$R_5$ (SEQ ID NO: 37)

EDDDDKA-aca-$R_6$ (SEQ ID NO: 38)

EEEDDDEEEDA-aca-$R_9$ (SEQ ID NO: 39)

ededdAAeeeDDDDKA-aca-$R_{11}$ eddededeDDDDKA-aca-$R_6$-AGA-$R_6$

Ggedgddeeeeeeddeed-aca-PLGLAG-aca-$R_8$-AAA-$R_{12}$ eeddeeddKA-aca-$R_7$ eDDDDKA-aca-RGRGRRR eddddeeeeeee-aca-PLGLAGKA-aca-$R_{10}$ eeeeeeeeeeeeeeee-aca-DDDDKA-aca-$R_{20}$ -continued eeeeeeeeeddddd-aca-DDDDKA-aca-R$_{17}$ dddddddddddddddd-aca-PLGLAG-aca-R$_{14}$ eeeeee-ahx-PLG LAG-rrrrrrrrr

EEEEEDDDDKAXRRRRRRRRR (SEQ ID NO: 40)

EEEEEDDDDKARRRRRRRRR (SEQ ID NO: 41)

EDDDDKAXRRRRRRRRR (SEQ ID NO: 42)

EEDDDDKARXRRXRRXRRXRR (SEQ ID NO: 43)

DDDDDDKARRRRRRRRR (SEQ ID NO: 44)

EEDDDDKAXrrrrrrrrr eeeeeeXPLGLAGrrrrrrrrr eeeeeeeeXPLGLAGrrrrrrrrr eeeeeeXPLGLAGrrrrrrrrr eeeeeeeeXPLGLAGrrrrrrrrr eeeeeeeeXPLGLAGrrrrrrrrr eeeeeeeeXLALGPGrrrrrrrrr rrrrrrrrrXPLGLAGeeeeeeee rrrrrrrrrXSGRSAeeeeeeee eeeeeeXSGRSAXrrrrrrrrr rrrrrrrrrc-SS-ceeeeee e$_8$-XPLGLAG-r$_9$ eeeeee-(ahx)-PLGLAG-rrrrrrrrr eeeeeeeeXPLGLAGrrrrrrrrr eeeeeeeeXLALGPG-rrrrrrrrr e$_9$-ahx-PLGLAG-r$_9$ e$_9$-XPLGLAG-r$_9$ e$_9$-XPLGLAX-r$_9$ e$_6$-XPLGLAG-r$_9$ e$_9$-PLGLAG-r$_9$ In one embodiment, a pair of compounds (e.g., a polyanionic peptide and a polycationic peptide) may be connected to form a molecular beacon, having complementary regions with a fluorophore and a fluorescent quencher associated together so that the fluorescence of the fluorophore is quenched by the quencher. One or both of the polyanionic peptide and a polycationic peptide may include the fluorophore and/or fluorescent quencher. In some embodiments, only one of the complementary regions includes a fluorophore or fluorescent quencher. In certain embodiments, the quencher moiety is part of (e.g., attached to) the cleavable linker X$^2$. In this embodiment, cleavage of linker X allows fluorescence of the fluorophore and detection of the cleavage. In certain embodiments, cellular uptake of the fluorescent portion of a molecular beacon will allow detection of the cell. For example, as illustrated in FIG. 2F of U.S. Pat. No. 7,985,401, the content of which is hereby expressly incorporated by reference in its entirety for all purposes, a quencher Q may be attached to an acidic portion A to form a MTS molecule having features Q-A-X-B-D, where D is fluorophore and is quenched by Q. The quenching of D by Q is relieved upon cleavage of X, allowing fluorescent imaging of portion B-D. The combination of fluorescence dequenching and selective uptake should increase contrast between tissues able to cleave X, compared to those that cannot cleave X.

Furthermore, the descriptions of suitable substrates, and portions thereof, provided in Examples 10, 11, and 12 of U.S. Patent Application Publication Number 2007/0041904 are hereby expressly incorporated by reference in their entireties for all purposes, as though they were reproduced herein.

Peptide Substrate Synthesis

FRET-ACPP imaging substrates described herein can be synthesized by standard synthetic techniques, for example, solid phase synthesis (e.g., solid phase peptide synthesis). An example of peptide synthesis using Fmoc is given as Example 1 in U.S. Pat. No. 7,431,915, the content of which is hereby expressly incorporated by reference in its entirety for all purposes. For example, conventional solid phase methods for synthesizing peptides may start with N-alpha-protected amino acid anhydrides that are prepared in crystallized form or prepared freshly in solution, and are used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1 to 2 reaction cycles are used for the first twelve residue additions, and 2 to 3 reaction cycles for the remaining residues.

After completing the growing peptide chains, the protected peptide resin is treated with a strong acid such as liquid hydrofluoric acid or trifluoroacetic acid to deblock and release the peptides from the support. For preparing an amidated peptide, the resin support used in the synthesis is selected to supply a C-terminal amide, after peptide cleavage from the resin. After removal of the strong acid, the peptide may be extracted into 1 M acetic acid solution and lyophilized. The peptide can be isolated by an initial separation by gel filtration, to remove peptide dimers and higher molecular weight polymers, and also to remove undesired salts The partially purified peptide may be further purified by preparative HPLC chromatography, and the purity and identity of the peptide confirmed by amino acid composition analysis, mass spectrometry and by analytical HPLC (e.g., in two different solvent systems).

V. Use of Ratiometric Activatable Cell Penetrating Peptides (RACPP) for the Detection of Cancer In one aspect, a family of novel ratiometric probes is provided for sensitive and specific molecular detection of primary tumors and lymph node metastases. In a specific embodiment, the probe includes a FRET fluorophore ratiometric pair with Cy5 as a far red fluorescent donor, which is quenched in favor of Cy7 re-emission until the intervening linker is cleaved by tumor-associated matrix metalloproteinases-2 & 9 (MMP-2,-9) or elastases, which increase the Cy5:Cy7 emission ratio 40 fold and trigger tissue retention of the Cy5-containing fragment. This large change in ratio provides a wide dynamic range in which protease activity in tumors and metastases can be quantitatively differentiated from adjacent normal tissue.

Previous attempts to develop "smart" amplifying probes for in vivo imaging of protease activity have been based on fluorescence dequenching or differential pharmacokinetic washout (Olson, E. S. et al., *Integrative Biology* 1, 382-393 (2009); Aguilera, T. A. et al., *Integrative Biology* 1, 371-381 (2009); van Duijnhoven, S. M. et al., *J Nucl. Med* 52, 279-286 (2011); Whitney, M. et al., *J Biol Chem* 285, 22532-22541 (2010); Olson, E. S. et al., *Proc Natl Acad Sci USA* 107, 4311-4316 (2010); Bremer, C. et al., *Radiology* 221, 523-529 (2001); Bremer, C. et al., *Nature Medicine* 7, 743-748 (2001); Jiang, T. et al., *Proc Natl Acad Sci USA* 101, 17867-17872 (2004); Levi, J. et al., *Journal of the American Chemical Society* 132, 11264-11269 (2010), the contents of which are hereby expressly incorporated by reference in their entireties for all purposes). Fluorescence dequenching has been widely used because the uncleaved probe starts with low signal, which minimizes nonspecific background. These probes primarily rely on dark quenchers such as BHQ-3, or concentration-dependent self-quenching (Bremer, C. et al., *Radiology* 221, 523-529 (2001); Bremer, C. et al., *Nature Medicine* 7, 743-748 (2001); Linder, K. E. et al., *Bioconjugate chemistry* 22, 1287-1297 (2011), the contents of which are hereby expressly incorporated by reference in their entireties for all purposes).

Although these strategies have varying levels of efficacy, one inherent problem with all such methods is that fluorescence intensity is highly vulnerable to factors other than MMP activity. For example, the use of a dark quencher such as BHQ-3 has recently been shown to be problematic due to the in vivo instability of BHQ-3, leading to nonspecific dequenching within a few minutes after injection (Linder, K. E. et al., supra). Analogs of RACPPs have been synthesized with pheophorbide (Chen, J. et al., *Bioconjugate chemistry* 20, 1836-1842 (2009)) or Alexa 750 (Levi, J. et al., *Journal of the American Chemical Society* 132, 11264-11269 (2010)) in place of Cy5 and BHQ-3 instead of Cy7, but these probes were non-ratiometric, failed to dissociate completely after linker cleavage (perhaps because the chromophores are relatively hydrophobic and sticky), and were not tested in vivo. Cy5 and Cy7 both carry water-solubilizing sulfonates and a net negative charge, which probably reduce their mutual affinity and non-FRET quenching. Self-quenched probes such as MMPSense are typically made from high molecular weight polymeric carriers that require a long post-injection wait time (24 hr; Technical Data Sheet, Fluorescent Imaging Agent MMPSense™ 680, PerkinElmer, Inc.) for optimal contrast development and washout of nonspecific binding, presumably due to the slow linker cleavage rate compared to small peptides. Dequenching alone cannot be differentiated from enhanced penetration and retention (EPR) or poor washout from the tumor site.

Inclusion of a metabolically stable, re-emissive acceptor gives RACPPs a major advantage over previously described single-fluorophore probes including our own ACPPs with or without attached dendrimers, in that the ratio of the two fluorescence emissions as a function of protease activity allows quantification that is independent of total probe uptake, varying washout of nonspecific binding, and thresholding (FIGS. 21B-D, 17F-H, and 25) compared to single-wavelength intensity measurements. The polycationic and polyanionic domains in RACPPs not only confer favorable pharmacokinetics (diffusible substrate before cleavage, adherent localizable product afterwards) but maintain the same ~40× increase in Cy5/Cy7 emission ratio regardless of alterations in the cleavable linker sequence. RACPPs have already been generalized to target elastases (FIG. 21E-H) and thrombin (data not shown), and should be able to report any extracellular cleavage in vivo of a linker between the polycationic and polyanionic sequences.

Another important advantage of RACPP is the rapidity of ratiometric change as indicator of cancer invasion, compared to the 6 and 24 hr optimal for non-ratiometric ACPPs by themselves (Olson, E. S. et al., *Integrative Biology* 1, 382-393 (2009); Whitney, M. et al., *J Biol Chem* 285, 22532-22541 (2010); Jiang, T. et al., *Proc Natl Acad Sci USA* 101, 17867-17872 (2004)) or attached to dendrimers (Nguyen, Q. T. et al., *Proc Natl Acad Sci USA* 107, 4317-4322 (2010); Olson, E. S. et al., *Proc Natl Acad Sci USA* 107, 4311-4316 (2010)), or 24 hr for commercially available dequenching probes (Technical Data Sheet, Fluorescent Imaging Agent MMPSense™ 680, PerkinElmer, Inc.).

Figure 24A:
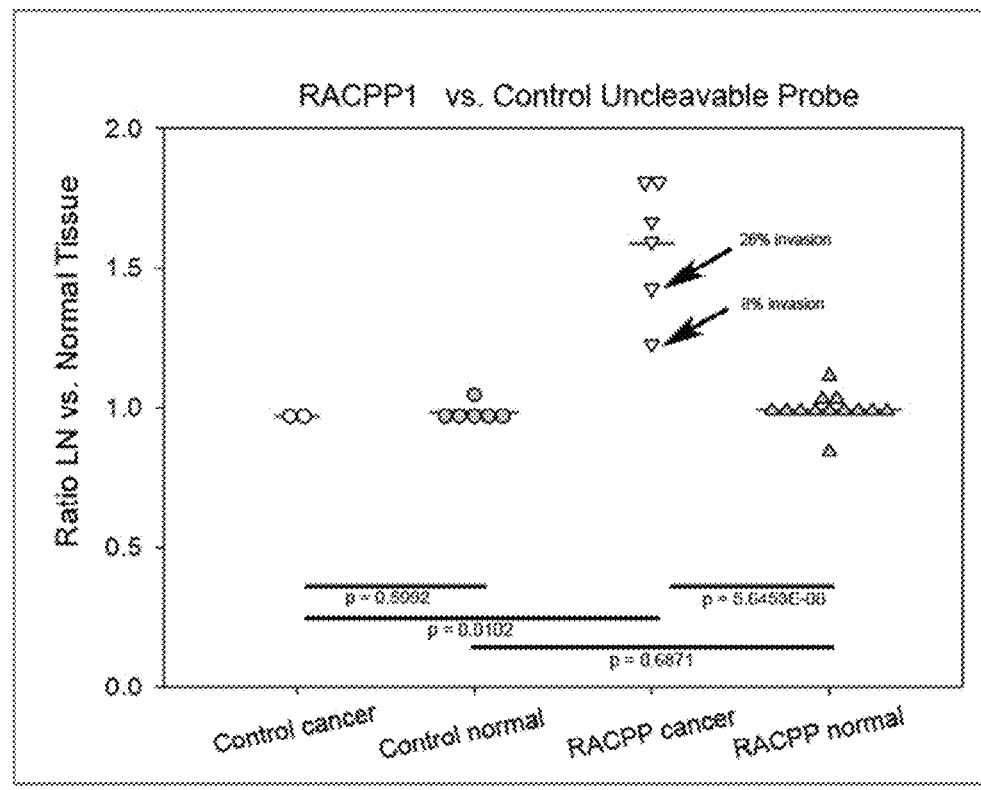
FIG. 24 illustrates (A) Cy5/Cy7 ratio of lymph nodes versus adjacent normal tissue in animals injected intravenously with either control uncleavable probe or RACPP1. Each symbol represents a separate lymph node whose status (solid=metastatic, hollow=non-metastatic) was independently determined by histology. In mice injected with control uncleavable probe, the presence (solid circles) or absence (hollow circles) of cancer invasion did not change the ratio of lymph node Cy5/Cy7 emission ratios relative to adjacent normal tissue, all values being near 1. In mice injected with RACPP1, lymph nodes with cancer invasion (solid triangles) had significantly higher ratios than lymph nodes without cancer invasion (hollow triangles). Interestingly, the ratio of Cy5/Cy7 emission ratios in nodes vs. adjacent normal tissue correlated with the degree of cancer invasion, where the lymph nodes with partial cancer invasion (arrows) showed less ratio increase (albeit still higher than any normal tissue) than lymph nodes with 100% cancer invasion. (B) Dot density graph showing higher sensitivity/specificity of RACPP1 compared to ACPPD in the differentiation between lymph nodes bearing cancer invasion (solid symbols) versus adjacent normal tissue (hollow symbols). For ACPPD, although mean Cy5 fluorescence intensity of metastatic lymph nodes relative to adjacent normal tissue (solid circles) is significantly higher (p=0.02) than for lymph nodes without metastasis (open circles), there is overlap which decreases sensitivity/specificity. Metastatic lymph nodes in mice following IV injection of RACPP1 show higher Cy5 intensity relative to adjacent normal tissue (solid triangles), Cy5/Cy7 ratio alone (solid squares) or ratios against adjacent normal tissue (solid diamonds) significantly higher (p=$7\times10^{-4}$, $8\times10^{-5}$, $7\times10^{-4}$, respectively) than nonmetastatic nodes (hollow symbols). Because metastatic and benign nodes do not overlap in the RACPP1 ratios, sensitivity and specificity can be 100%.
Figure 24B:
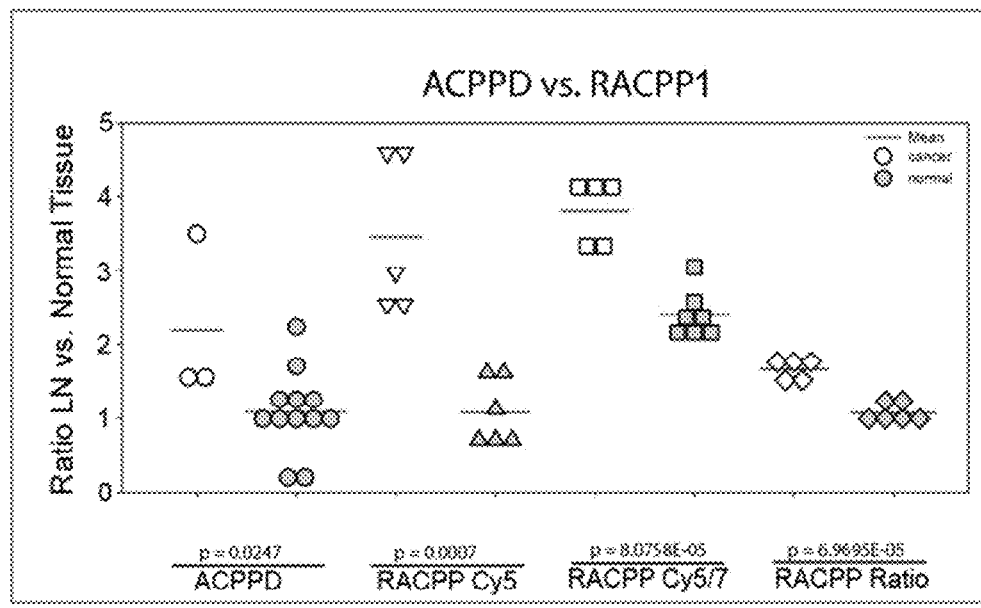

The faster time frame (1-2 hours) of the molecular detection method provided herein allows intraoperative real time assessment of lymph node status and represents a significant advance to current SLN detection methods that identify node location without any information regarding cancer invasion. Finally, the dequenching mechanism of RACPP improved the contrast of Cy5 alone compared to single fluorophore ACPPs or ACPPD enough to enhance specificity/sensitivity for cancer detection in metastatic lymph nodes (FIG. 24B). This interim improvement, though inferior to emission ratioing, is valuable because fluorescence imaging for clinical use (van Dam, G. M. et al., *Nature Medicine* 17, 1315-1319 (2011); Hutteman, M. et al. *Am J Obstet Gynecol* 206, 89 e81-85 (2012), the contents of which are hereby expressly incorporated by reference in their entirety for all purposes) is in its infancy and most instruments currently available in operating rooms can perform only single fluorophore imaging. Future intraoperative implementation of RACPPs should decrease incidence of positive margins, minimize time spent waiting for a pathologist to scrutinize frozen-sectioned margins, and streamline intraoperative decision making by providing real-time knowledge of lymph-node status during surgery.

Management of metastatic disease is integral to cancer treatment. Evaluation of metastases often requires surgical removal of all anatomically susceptible lymph nodes for ex vivo pathological examination. In one aspect, the present disclosure provides a family of novel ratiometric activatable cell penetrating peptides (RACPP), which contain fluorescent donor and acceptor fluorophores competent for FRET imaging. In a particular embodiment, the RACPP contain Cy5, as far red fluorescent donor and Cy7, as near-infrared fluorescent acceptor. Upon excitation, Cy5 emission is quenched in favor of Cy7 re-emission until the intervening linkers are cleaved by a tumor-associated protease, e.g., matrix metalloproteinases-2 & 9 (MMP-2,-9) or elastases. Such cleavage increases the emission ratio, e.g., increases the Cy5:Cy7 emission ratio 40 fold, and triggers tissue retention of the peptide fragment containing the FRET acceptor fluorophore, e.g., the Cy5-containing fragment. This ratiometric increase provides an accelerated and quantifiable metric to identify primary tumors and metastases to liver and lymph nodes with increased sensitivity and specificity. This technique represents a significant advance over existing non-ratiometric protease sensors and sentinel lymph node detection methods, which give no information regarding cancer invasion.

Figure 1A:
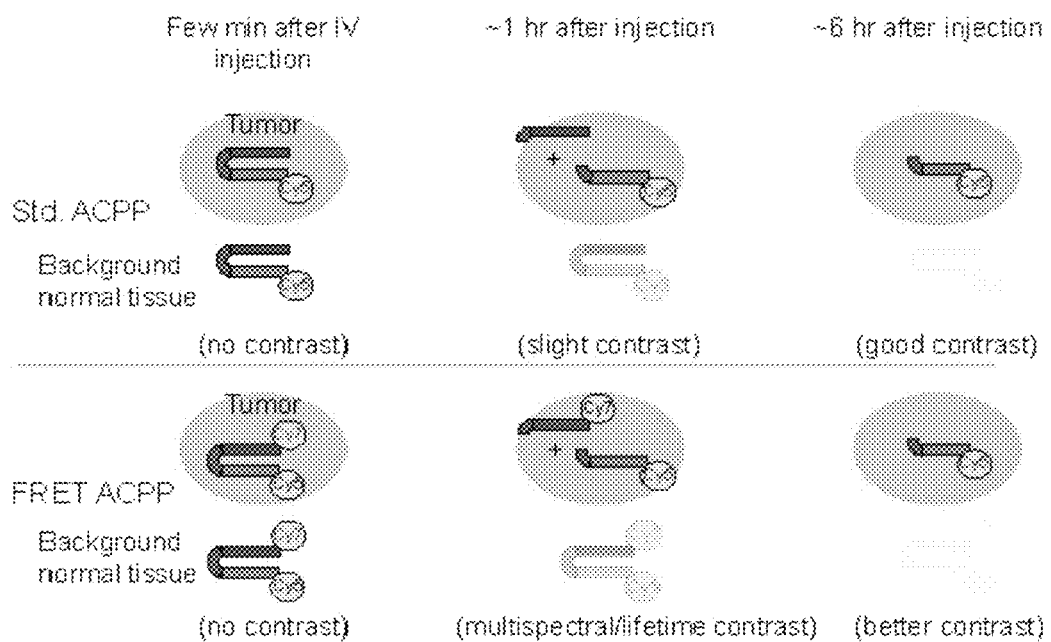
FIG. 1A shows schematics of how previous non-ratiometric ACPPs (Standard ACPP, top panels) and RACPP (bottom panels) generate contrast for tumor (ellipse) over normal tissue. Immediately after IV injection, neither configurations has had time to produce any tumor contrast (left panels). Within 1-2 hr, the standard ACPP gives modest tumor to background contrast due to incomplete pharmacokinetic washout of the uncleaved probe from normal tissues (top middle panel), whereas spectacular tumor contrast can be obtained with RACPP (bottom middle panel; pseudocolor red denotes high Cy5/Cy7 emission ratio). Excessive waiting time such as 24 hr after IV injections results in loss of tumor contrast in either configuration (right panels), due to eventual background cleavage in normal tissues and/or slow migration of cleavage product from sites of high enzymatic activity.

In one embodiment, the RACPP substrates are created by attaching a FRET donor and acceptor fluorophore pair to the polycationic and polyanionic domains of an ACPP molecule, respectively, as shown in FIG. 1A. The relatively small size of ACPP substrates enforces the donor and acceptor fluorophores remain in sufficiently close proximity to allow fluorescence resonance energy transfer (FRET), and synergistically combine fluorescence dequenching with preferential retention of the cleaved probe.

Figure 1B:
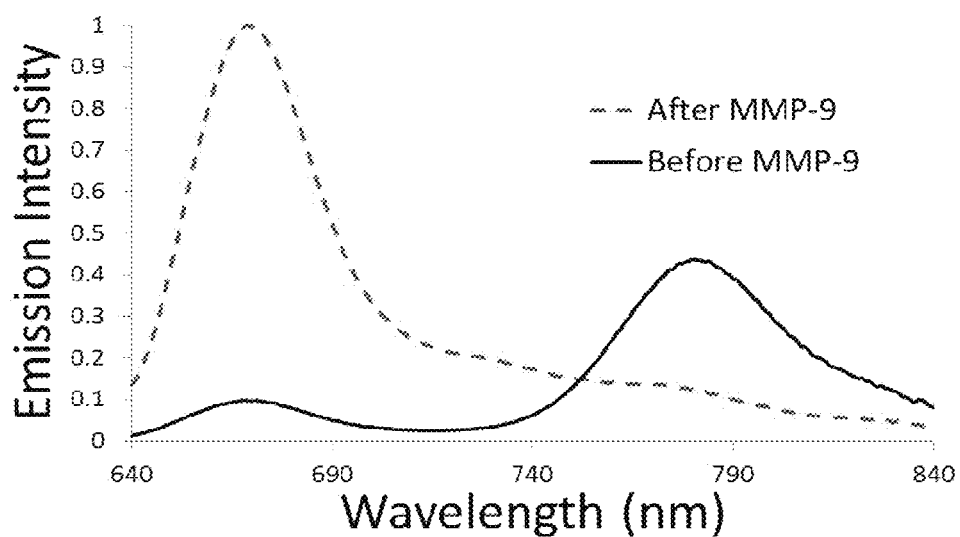
FIG. 1B illustrates the emission spectrum of RACPP1, excited at 630 nm, measured in mouse plasma in a cuvet spectrofluorometer, before (black solid curve) and after (red dashed curve) >95% complete cleavage with MMP-9. The starting spectrum shows considerable quenching of the Cy5 peak at 670 nm and re-emission from Cy7 at 780 nm, whereas the final spectrum is almost purely that of Cy5.

Determining the ratio of the donor to acceptor emissions in these RACPP substrates results in more rapid and specific tumor contrast as compared to previously described non-ratiometric ACPPs (FIG. 1A). The emission spectrum of a prototypic RACPP (RACPP1, cleavable sequence=(SEQ ID NO:7) PLGC(Me)AG) in mouse plasma (FIG. 1B, black line) shows only slight emission from Cy5 (peak~670 nm), compared to re-emission of Cy7 (peak~780 nm), consistent with efficient FRET. Addition of MMP-9 increased Cy5 emission by ~10 fold and decreased Cy7 re-emission by ~4 fold (FIG. 1B, red dashed line). The net 40-fold increase in the ratio of 670/780 nm emissions exceeds the dynamic range of the best emission ratiometric $Ca^{2+}$ indicators (Tsien, R. Y. in *Calcium as a Cellular Regulator*, 28-54, Oxford University Press, New York; 1999) or intramolecular FRET-paired fluorescent proteins (Tsien, R. Y. in *Imaging in Neuroscience and Development*, 549-556, Cold Spring Harbor Laboratory Press, Cold Spring Harbor; 2005).

In one aspect, the present disclosure provides a method for imaging a tumor and/or cancerous tissue in a subject, comprising administration of a RACPP substrate as disclosed herein to the subject.

In one aspect, the present disclosure provides a method for imaging a surgical margin for a tumor or tissue resection in a subject, comprising administration of a RACPP substrate as disclosed herein to the subject.

VI. Use of Ratiometric Activatable Cell Penetrating Peptides (RACPP) for the Detection of Thrombin Activation Extracellular proteases including thrombin are involved in numerous biological processes and play major roles in variety of human diseases. The spatial and temporal patterns of activation of proteases in vivo control their biological role in diseases and amenability to therapeutic targeting. Previously we developed activatable cell penetrating peptides (ACPPs) to monitor matrix metalloproteinase (MMP) and elastase activity in tumors, and have extended ACPPs to detect thrombin activation in atherosclerosis and brain injury.

We have now modified the thrombin ACPP to provide a FRET-dependent emission ratiometric readout. This ratio improves kinetic detection of enzyme activity because it reflects the ratio of cleaved versus uncleaved probe, while canceling out total probe concentration, illumination intensity, detection sensitivity, and tissue thickness. Because pharmacokinetic washout of uncleaved probe is not necessary in the imaging system provided herein, although the cleavage converts a diffusible substrate into an immobilized product, thrombin activity can be imaged in real time with good spatial resolution.

The new ratiometric ACPPs provided herein detect localized thrombin activation in rapidly forming blood clots minutes after probe injection, and signal is inhibited by the thrombin specific inhibitor, hirudin. Thrombin ratiometric ACPP also detected thrombin activity in sub-regions of atherosclerotic plaques, which may allow intraoperative imaging both to help treat or to avoid inadvertently disturbing such plaques.

Ratiometric-ACPPs (e.g., RACPP, structures 5, 10, 15, and 20 in FIG. 27) differ from non-ratiometric ACPPs by the attachment of a fluorescent acceptor such as Cy7 to the polyanionic domain so that in the intact, uncleaved probe, Cy5 on the polycationic domain undergoes efficient fluorescence resonance energy transfer (FRET) to the acceptor (FIG. 28A). Upon linker cleavage by thrombin, the resulting separation of the polyanionic and polycationic sequences disrupts FRET, instantly restoring the Cy5 (peak~670 nm) fluorescence and eliminating the Cy7 (peak~780 nm), re-emission. The Cy5 attached to the CPP portion of the probe is retained at the site of cleavage so that its dequenched emission remains localized. In vitro, the addition of purified thrombin to an RACPP with substrate sequence (SEQ ID NO:2) PPRSFL ((SEQ ID NO:2) RACPP$_{PPRSFL}$) diluted in plasma resulted in a 34 fold change in Cy5/Cy7 emission ratio. This ratio change is the result of an 8.8 fold increase in Cy5 emission (FIG. 28B, blue line) and a 3.8 fold decrease in Cy7 re-emission (FIG. 28B, red line).

Ratiometric ACPPs selectively cleaved by thrombin provide a sensitive probe for monitoring physiologically activated thrombin in real time. FRET from Cy5 to Cy7 within an ACPP provides a significant improvement over intensity based ACPPs or fluorescence dequenching probes by eliminating the need for washout to generate contrast at the site of cleavage and canceling many non-enzymatic factors that perturb intensity measurements at single wavelength bands.

As shown in the examples below, RACCPs were used to detect a thrombin dependent ratio change in clotting blood less than 10 min after intravenous injection of the RACP-P$_{PPRSFL}$ (10) peptide substrate. Sensitivity should be improved if a substrate can be identified that is more rapidly cleaved by thrombin. Several recent reports describe potentially new thrombin selective substrates that could be incorporated into RACPPs to increase both sensitivity and specificity (van Berkel S. S., et al., *ChemMedChem* 2012, 7, 606-617; Gallwitz M., et al., *PloS One* 2012, 7, e31756, the contents of which are hereby expressly incorporated by reference in their entireties for all purposes).

Thrombin activation is dynamically regulated in clotting blood and continues to be active even when bound to fibrin after the clot has formed. Previous work with a near-infrared fluorescent (NIRF) dequenching probe demonstrated diffuse and rapid thrombin activation within 12 minutes of tail clipping, although thrombin specificity was not tested with pharmacological inhibitors (Jaffer F. A., et al., *Arteriosclerosis, Thrombosis, and Vascular Biology* 2002, 22, 1929-1935). Signal from the dequenching probe was dispersed throughout the clot whereas our results show the highest ratio closest to the wound site, possible because of localized thrombin and probe retention at the site of cleavage. Thrombin specific antibodies can be used to localize thrombin and prothrombin antigen, but immunohistochemistry is destructive and static, and immunoreactivity does not necessarily correlate with proteolytically active thrombin. It is also demonstrated herein that the FRET probe is consistently and significantly protected from protease cleavage when hirudin is co-administered. Further studies are needed to test this probe in clinically relevant clots such as deep vein thrombosis and stroke.

Preliminary studies show (SEQ ID NO:1) RACPP$_{DPRSFL}$ (5) can sensitively detect thrombin activity in sub-regions of atherosclerotic plaques in the aorta and carotid arteries. Other clinical methods such as magnetic resonance imaging (MRI) or ultrasound can easily measure plaque burden, but accurate clinical staging of plaques typically requires post mortem pathological analysis. Our previous report showed increased fluorescence uptake of non-ratiometric thrombin cleavable ACPP in plaques with histologic features associated with more advanced disease from human studies (Olson E. S., et al., *Integrative Biology: Quantitative Biosciences from Nano to Macro* 2012, 4, 595-605; Stone G. W., et al., *The New England Journal of Medicine* 2011, 364, 226-235; Stary H. C., et al., *Circulation* 1995, 92, 1355-1374). The non-ratiometric thrombin ACPPs also showed a correlation between thrombin activity and the severity and spatial extent of damage in the penumbra of ischemic stroke (Chen B., et al., *The Journal of Neuroscience: the Official Journal of the Society for Neuroscience* 2012, 32, 7622-7631). Ratiometric ACPPs should be even better for such studies on disease etiology, because they signal thrombin activity more quickly and more reliably. For example, some zones of high enzyme activity may be so poorly perfused as to be inaccessible to the probe. With a non-ratiometric probe, those zones would be indistinguishable from regions with perfusion but low enzyme activity. With a ratiometric probe, inaccessible zones would have no signal at either wavelength, whereas perfused regions with low enzyme activity would show strong FRET and thus be clearly distinguishable.

Analogous ACPPs attached to dendrimers labeled with Gd chelates have given MRI contrast for primary tumors (Olson E. S., et al., *PNAS U.S.A.* 2010, 107, 4311-4316) and metastatic lymph nodes (Nguyen et al., unpublished). Accordingly, in one aspect, the present disclosure provides FRET-ACPP substrates attached to dendrimers labeled with a heavy metal, e.g., Gd chelates.

Endoscopic catheters can now image within arteries (Yoo H., et al., *Nature Medicine* 2011, 17, 1680-1684), so optical discrimination of atherosclerotic plaque from inside the artery could be valuable, especially if a correlation between thrombin activity and plaque vulnerability could be validated. Imaging of plaques from outside the artery as demonstrated in FIG. 33 could be valuable during surgery either to graft a bypass or to remove a nearby tumor, when it is important to avoid disturbing the plaque.

In certain embodiments, is a method of imaging thrombin activity in a subject. In some embodiments, the method comprises imaging thrombin activity after the subject has been administered an imaging substrate molecule as disclosed herein.

In some embodiments, an increase in thrombin activity over normal ranges indicates the presence of a cancer, ischemia, or an atherosclerotic plaque.

In some embodiments, the signal intensity, donor to acceptor ratio, or excitation lifetime of an imaging agent corresponds to the total atherosclerotic plaque burden, histologic stage of the atherosclerotic plaque, and provides evidence of recent plaque rupture. In some embodiments, administering an imaging substrate molecule disclosed herein allows a medical professional to image the surgical margins of an atherosclerotic plaque for removal.

In some embodiments, the signal intensity, donor to acceptor ratio, or excitation lifetime of an imaging agent corresponds to the size of the tumor. In some embodiments, administering an imaging substrate molecule disclosed herein allows a medical professional to evaluate the progression or regression of a tumor. In some embodiments, administering an imaging substrate molecule disclosed herein allows a medical professional to image the surgical margins for a tumor or tissue resection in a subject in need thereof.

In some embodiments, the signal intensity, donor to acceptor ratio, or excitation lifetime of an imaging agent corresponds to amount of ischemia and the damage to the surrounding cells. As used herein, "ischemia" means a shortage of the blood supply to an organ, (i.e. a shortage of oxygen, glucose and other blood-borne fuels). In some embodiments, ischemia is caused by occlusion of a vessel or artery (e.g., due to an embolism or thrombosis). In some embodiments, ischemia is caused by hemorrhage. In some embodiments, ischemia results in a stroke. In some embodiments, administering a selective transport molecule disclosed herein allows a medical professional to evaluate a subject's risk of developing a stroke.

In some embodiments, the image of thrombin activity is memorialized (i.e., a record is created) in print (e.g., as a photograph).

In some embodiments, image of thrombin activity is stored in a computer module. In some embodiments, the image of thrombin activity is stored in computer memory. In some embodiments, the image of thrombin activity is stored as a visual file (e.g., JPEG, MPEG, MPEG-2, H.264/MPEG-4 AVC, and SMPTE VC-1). In some embodiments, the image of thrombin activity is stored in volatile computer memory. As used herein, "volatile memory" means computer memory that requires electricity to maintain the stored information. In some embodiments, the volatile memory is random access memory (RAM), dynamic random access memory (DRAM), or static random access memory (SRAM). In some embodiments, the image of thrombin activity is stored in non-volatile computer memory. As used herein, "non-volatile memory" means computer memory that retains the stored information in the absence of electricity (e.g., hard disks, floppy disks, and magnetic tape, or optical discs). In some embodiments, the image of thrombin activity is stored on an optical disc (e.g., a Blu-Ray disc, DVD, or a CD). In some embodiments, the image of thrombin activity is stored on a magnetic storage device.

Visualizing Tumors

In some embodiments, an imaging substrate molecule disclosed herein is administered to a subject in need thereof to visualize a tumor. In some embodiments, an imaging substrate molecule disclosed herein is administered to a subject in need thereof prior to surgery. In some embodiments, an imaging substrate molecule disclosed herein is administered to a subject in need thereof prior to surgery and used to define the surgical margins of a tumor. In some embodiments, a dual modality (MR and fluorescence) imaging substrate molecule allows pre-operative staging by oncologists and radiologists, particularly for cancers such as prostate where invasion of a capsule is important, preventing surgery on patients who are non-operative candidates. In some embodiments, the anatomical and biochemical information given by the dual label imaging substrate molecule are useful for surgeons in planning complex surgical procedures. In some embodiments, tight binding of an imaging substrate molecule to the site of cleavage provides localized information regarding tumor biology that not only allows the surgeon to focus on the most invasive areas of tumor growth with intraoperative fluorescence imaging but also allows the pathologist to do the same with intraoperative histology. Following surgery, in some embodiments, the dual probe allows further evaluation for completeness of tumor removal with a second MRI.

In some embodiments, the image of a tumor is memorialized (i.e., a record is created) in print (e.g., as a photograph).

In some embodiments, image of a tumor is stored in a computer module. In some embodiments, the image of a tumor is stored in computer memory. In some embodiments, the image of a tumor is stored as a visual file (e.g., JPEG, MPEG, MPEG-2, H.264/MPEG-4 AVC, and SMPTE VC-1). In some embodiments, the image of a tumor is stored in volatile computer memory. As used herein, "volatile memory" means computer memory that requires electricity to maintain the stored information. In some embodiments, the volatile memory is random access memory (RAM), dynamic random access memory (DRAM), or static random access memory (SRAM). In some embodiments, the image of a tumor is stored in non-volatile computer memory. As used herein, "non-volatile memory" means computer memory that retains the stored information in the absence of electricity (e.g., hard disks, floppy disks, and magnetic tape, or optical discs). In some embodiments, the image of a tumor is stored on an optical disc (e.g., a Blu-Ray disc, DVD, or a CD). In some embodiments, the image of a tumor is stored on a magnetic storage device.

In some embodiments, an imaging substrate molecule disclosed herein is administered to a subject in need thereof to visualize a tumor. In some embodiments, an imaging substrate molecule disclosed herein is administered to a subject in need thereof prior to surgery. In some embodiments, a selective transport molecule disclosed herein is administered to a subject in need thereof prior to surgery and used to define a tumor or cancerous tissue.

Visualizing Atherosclerotic Plaques

In some embodiments, an imaging substrate molecule disclosed herein is administered to a subject in need thereof prior to surgery. In some embodiments, an imaging substrate molecule disclosed herein is administered to a subject in need thereof prior to surgery and used to highlight high risk plaques intraoperatively. In some embodiments, administering an imaging substrate molecule disclosed herein prior to surgery lowers patient morbidity in surgical procedures (e.g., carotid endarterectomy). In some embodiments, administering an imaging substrate molecule disclosed herein prior to surgery lowers patient morbidity in iatrogenic surgical procedures, coronary artery surgical procedures, and mesenteric artery surgical procedures. In some embodiments, administering a selective transport molecule disclosed herein prior to surgery reduces the incidence of embolic events, myocardial infarction and bowel necrosis.

In some embodiments, the image of an atherosclerotic plaque is memorialized (i.e., a record is created) in print (e.g., as a photograph).

In some embodiments, image of an atherosclerotic plaque is stored in a computer module. In some embodiments, the image of an atherosclerotic plaque is stored in computer memory. In some embodiments, the image of an atherosclerotic plaque is stored as a visual file (e.g., JPEG, MPEG, MPEG-2, H.264/MPEG-4 AVC, and SMPTE VC-1). In some embodiments, the image of an atherosclerotic plaque is stored in volatile computer memory. As used herein, "volatile memory" means computer memory that requires electricity to maintain the stored information. In some embodiments, the volatile memory is random access memory (RAM), dynamic random access memory (DRAM), or static random access memory (SRAM). In some embodiments, the image of an atherosclerotic plaque is stored in non-volatile computer memory. As used herein, "non-volatile memory" means computer memory that retains the stored information in the absence of electricity (e.g., hard disks, floppy disks, and magnetic tape, or optical discs). In some embodiments, the image of an atherosclerotic plaque is stored on an optical disc (e.g., a Blu-Ray disc, DVD, or a CD). In some embodiments, the image of an atherosclerotic plaque is stored on a magnetic storage device.

Management of Atherosclerotic Disease

In some embodiments, an imaging substrate molecule disclosed herein is administered to a subject to aid in management of atherosclerotic disease. In some embodiments, an imaging substrate molecule disclosed herein is administered to a subject to aid a medical professional in distinguishing pathologic features of a plaque with the potential to rupture and cause embolic disease. In some embodiments, an imaging substrate molecule disclosed herein is administered to a subject to aid a medical professional in distinguishing patients with plaques at high risk for rupture, or the "high risk patient." In some embodiments, an imaging substrate molecule disclosed herein is administered to a subject to aid a medical professional in characterizing the risk associated with an atherosclerotic plaque in a subject, wherein the risk is proportional to the imaging agent signal intensity. Currently tissue examination of excised carotid endarterectomy fragments includes looking for distinctive pathological features such as fissures, micro-ulcerations, microthrombi or calcified nodules. This task is much more difficult in specimens that do not contain vessel wall, leading to significant intraobserver variability in identifying the rupture potential of surgically excised plaques (e.g., those removed during carotid endarterectomy).

VII. Applications

In one aspect, the invention provides use of the compounds disclosed herein in various clinical applications. For example, the compounds can be used for real-time fluorescence guidance of surgery of diseases such as cancer and atherosclerotic plaques. Preclinical applications would include in vivo detection of enzymatic activities and screening of protease inhibitors in mice or other experimental animals.

In some embodiments, the disclosure provides methods for labeling a tissue (e.g., to define the surgical margins for a tumor resection) by administering to a patient in need there of an imaging substrate described herein. In some embodiments, the tissue is a tumor. In some embodiments, the tissue is ischemic tissue. In some embodiments, the tissue is hypoxic tissue. In some embodiments, the tissue is necrotic tissue. In some embodiments, the tissue is acidotic tissue. In some embodiments, the tissue is diseased tissue (e.g., tissue infected by an infectious agent, tissue contacted with a poisonous agent, tissue subject to an autoimmune disorder, tissue that is inflamed).

In some embodiments, the tissue is labeled for identification and removal during surgery. In some embodiments, the method of imaging the surgical margins for a tumor or tissue resection in a subject, comprises imaging the surgical margins after the subject has been administered an imaging substrate molecule disclosed herein. In some embodiments, the method of imaging a tumor in a subject comprises imaging the tumor after the subject has been administered an imaging substrate molecule disclosed herein. In some embodiments, the method of removing a tumor in a subject comprises removing the tumor after the subject has been administered an imaging substrate molecule disclosed herein.

In some embodiments, the method comprises administering an imaging substrate molecule described herein to a subject that will undergo surgery. In some embodiments, the method comprises administering an imaging substrate molecule described herein to a subject that is undergoing surgery. In some embodiments, an imaging substrate molecule described herein is administered to a patient systemically. In some embodiments, an imaging substrate molecule described herein is administered to a patient locally.

In some embodiments, an imaging substrate molecule disclosed herein is utilized at multiple stages in the evaluation and treatment of cancer. In some embodiments, a dual modality (MR and fluorescence) imaging substrate molecule allows pre-operative staging by oncologists and radiologists, particularly for cancers such as prostate where invasion of a capsule is important, preventing surgery on patients who are non-operative candidates. In some embodiments, the anatomical and biochemical information given by the dual label selective transport molecule are useful for surgeons in planning complex surgical procedures. In some embodiments, tight binding of an imaging substrate molecule to the site of cleavage provides localized information regarding tumor biology that not only allows the surgeon to focus on the most invasive areas of tumor growth with intraoperative fluorescence imaging but also allows the pathologist to do the same with intraoperative histology. Following surgery, in some embodiments, the dual probe allows further evaluation for completeness of tumor removal with a second MRI.

EXAMPLES

Example 1

FRET-ACPP Constructs

The concept underlying the FRET-ACPP imaging constructs described herein is illustrated in FIG. 1. In this figure, a tumor is represented by the ellipse embedded in background normal tissue. In this representation, Cy5 is the sole fluorophore attached to the single fluorophore ACPP construct (top). In the FRET-ACPP construct (bottom), Cy5 serves as the donor fluorophore and Cy7 is the acceptor fluorophore.

The use of FRET accelerates and increases tumor to background contrast in ACPPs. In single fluorophore ACPPs, both cleaved and uncleaved ACPP constructs contain a single Cy5 fluorophore and are spectroscopically indistinguishable from one another. In this embodiment, imaging contrast between tumor and normal tissue is visible only as fluorescence intensity and depends solely on pharmacokinetic washout of uncleaved ACPP, occurring preferentially in normal tissue. This washout takes time and depends on many factors other than enzyme activity. In FRET-ACPPs, cleavage causes an additional, instantaneous change in the fluorescence spectrum and lifetime. This spectroscopic or lifetime change is a much more specific indication of cleavage than total fluorescence intensity. Therefore FRET-ACPPs give larger, faster, and more robust contrast between sites of high and low proteolytic activity (e.g. tumors vs. background normal tissue), as compared to the contrast obtainable using single fluorophore ACPPs.

Example 2

Targeted FRET-ACPP Constructs

Figure 2:
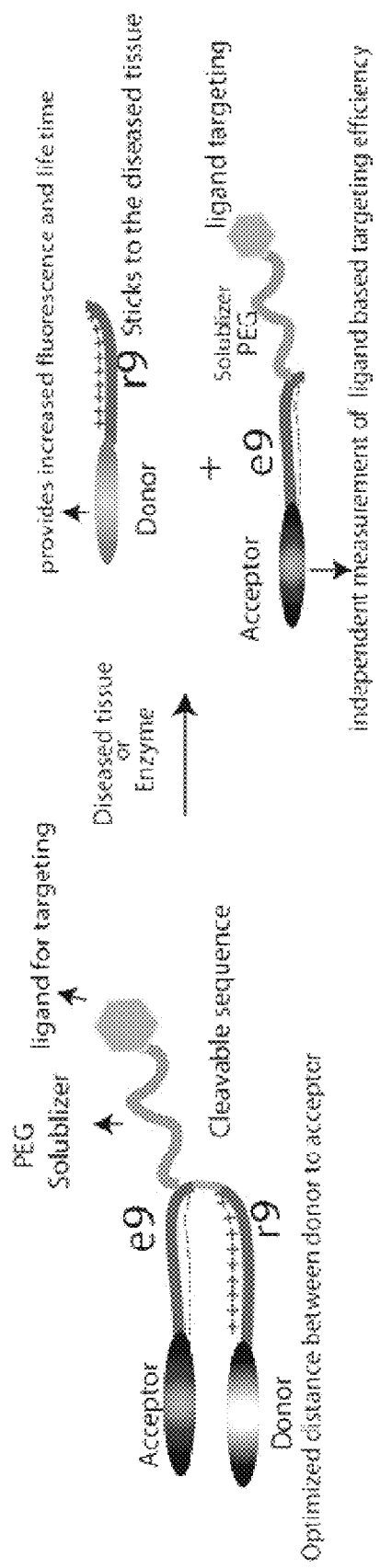
FIG. 2 illustrates another schematic of a FRET-ACPP, showing the optional extra targeting ligand (orange hexagon) attached to the polyanionic domain via a solubilizing poly(ethyleneglycol) linker (green squiggle).

As illustrated in FIG. 2, the present disclosure provides, in one embodiment, FRET-ACPP constructs containing an targeting ligand attached to the polyanionic domain. In certain embodiments, the targeting ligand is attached via a water-soluble linker, for example a PEG linker (green squiggle). The PEG linker increases solubility, helps prevent static quenching, and improves the emission spectral signature of FRET.

In one embodiment, the targeting ligand is cyclic (RGDfK), which binds to αvβ3 integrin, a known molecular partner of MMP-2. There is some literature precedent for the ability of cyclic(RGD) ligands to improve substrates for MMPs 9-11, but these examples do not include ACPPs.

Example 3

Synthesis of FRET-ACPPs

FIG. 3 illustrates a method for the synthesis of FRET-ACPPs, in one embodiment. The MMP-2/9-cleavable substrate in FRET-ACPPs 1 and 2 was chosen to be (SEQ ID NO:5) oPLGC(Me)AG, where o denotes 5-amino-3-oxopentanoyl, a short hydrophilic spacer. In the uncleavable controls 3 and 4, the linker was either oplgc(Me)ag (corresponding D-amino acids) or PEG6, which is even less cleavable but has the same number of bonds as the cleavable substrate. The targeting ligand was cyclic(RGDfK) or its inactive control, cyclic(RADfK).

Example 4

Response of FRET-ACPP 2 to MMP-9 In Vitro and Ex Vivo Tumors

Figure 4A:
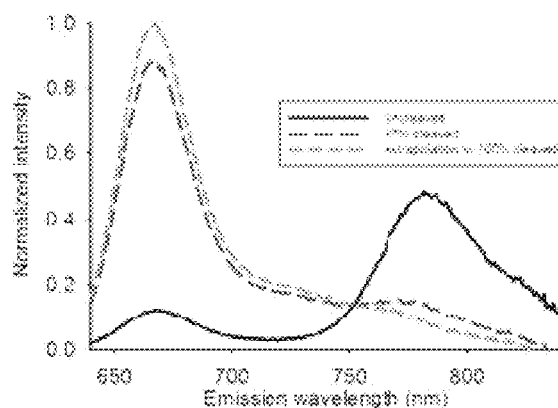
FIG. 4 shows the emission spectrum of FRET-ACPP 2, measured in mouse plasma in a cuvet spectrofluorometer, before (black solid curve) and after (red dashed curve) treatment with MMP-9.
Figure 4B:
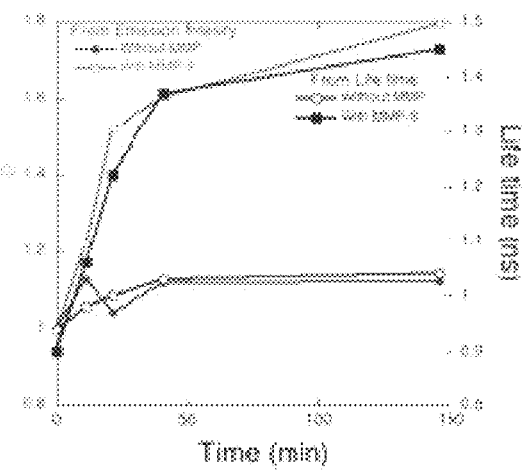

FIG. 4a shows the emission spectrum of FRET-ACPP 2, measured in mouse plasma in a cuvette spectrofluorometer, before (black solid curve) and after (red dashed curve) treatment with MMP-9. The starting spectrum shows considerable quenching of the Cy5 peak at 670 nm and re-emission from Cy7 at 780 nm. After treatment with MMP-9, analysis by HPLC showed that 87% of the peptide had been cleaved. The green dashed curve represents mathematical extrapolation to 100% cleavage, at which point the Cy5 peak increases about 7 fold, consistent with about an energy transfer efficiency of 86%. Meanwhile, the distinct emission peak at 780 nm disappears. FIG. 4b shows a parallel experiment in which the integrated intensity (red) and mean fluorescence lifetime (blue) for emission >693 nm was measured on an Optix scanner as a function of time, for samples with and without addition of MMP-9 at time zero. MMP-9 increased the lifetime of the FRET-ACPP 2 from 0.9 ns to 1.5 ns, whereas the control without MMP-9 showed an insignificant increase.

Figure 4C:
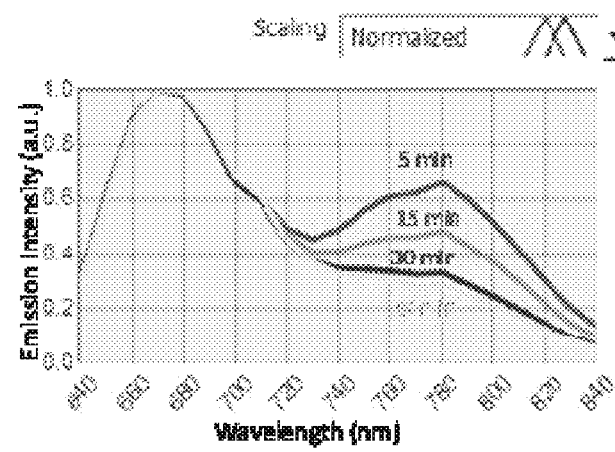
Figure 6B:
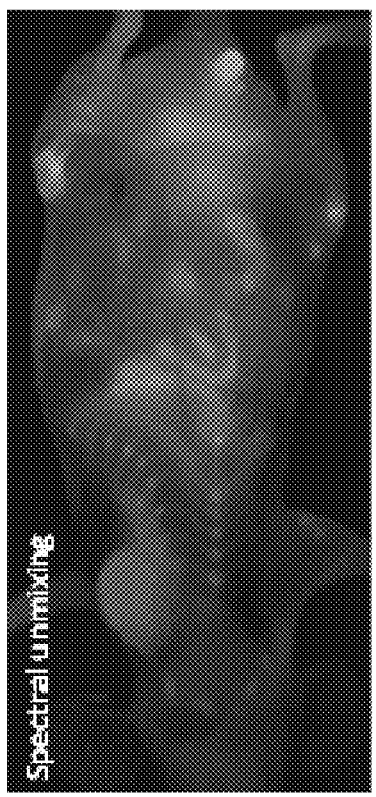
FIG. 6 shows in vivo monospectral (6A and 6C) and multispectral (6B and 6D) imaging of HT-1080 tumors in mice using FRET-ACPP 3 (6A and 6B) and FRET-ACPP 2 (6C and 6D) substrates.
Figure 6D:
Figure 6A:
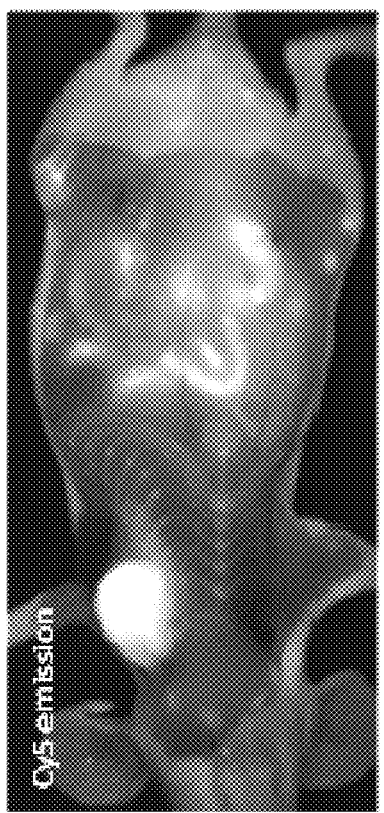
Figure 6C:

Theoretically, cleavage of the FRET-ACPP 2 should increase both intensity and lifetime by 7-fold if the Optix were monitoring only Cy5 emission, but the actual results are consistent with integrating all emission above 693 nm and thus including the pre-cleavage peak from Cy7 re-emission. FRET-ACPP 2 was then injected into HT-1080 tumors excised from mouse and imaged with a Maestro multispectral imager. As shown in FIG. 4c, the emission spectra changed to reflect progressive cleavage and loss of FRET over time, consistent with the results shown in FIG. 4a, given that the Maestro instrument used for detection inherently normalizes each successive spectrum to a maximum amplitude of 1.0. This demonstrates that the excised tumors could mimic MMP-9 in cleaving FRET-ACPP 2.

Example 5

Fluorescence Lifetime Imaging with FRET-ACPPs

FRET-ACPP 2 and FRET-ACPP 3 substrates were intravenously injected into mice containing HT-1080 tumors. The mice were imaged for lifetime fluorescence using an Optix lifetime scanner at several time points. FIG. 5A shows fluorescence lifetime imaging (FLI) using FRET-ACPP 2 a few minutes after injection. FIG. 5B shows FLI using FRET-ACPP 2 1 hour after injection. The tumors showed progressively increasing fluorescence lifetime of the FRET-ACPP 2 substrate, indicating decreased FRET (red pseudo-color in tumor) to a much greater extent than in surrounding normal tissue. As expected, an enzymatically resistant control probe (FRET-3) with D-amino acids, plgc(Me)ag, instead of L-amino acids, (SEQ ID NO:7) PLGC(Me)AG, showed far less change in lifetime or FRET efficiency in both tumor and normal tissues (FIGS. 5C and 5D).

A Maestro multispectral imager was then used to image the same mice after removal of their skin (FIG. 6). FIGS. 6A and 6C show imaging of characteristic Cy5 emission, a traditional way of monitoring single-fluorophore ACPP uptake, whereas FIGS. 6B and 6D show deconvoluted pseudocolored images of the mice. In the deconvoluted images, pixels having Cy5 emission only (cleaved FRET-ACPP substrate, indicative of tumor tissue) are represented as red, pixels having both Cy5 and Cy7 emission (uncleaved FRET-ACPP substrate, indicative of non-cancerous tissue) are represented as green, and pixels having gut autofluorescence are represented as purple. Cleavage of FRET-ACPP-2 (colored red) was largely confined to the tumor, while the probe seemed to remain intact in normal tissues (colored green) including cartilage, which shows positive contrast in the Cy5-only channels (FIGS. 6A and 6C). The control probe (FRET-ACPP 3) remained largely uncleaved in all tissues, as indicated by the green psuedocoloring.

Taking the results shown in FIGS. 5 and 6 together, fluorescence lifetime imaging using Optix and the spectral unmixing capability of the Maestro produced improved visual contrast between the tumor, normal tissues, and gut autofluorescence in only just over 1 hr after injection, whereas we usually need 6 hr after injection to develop optimal tumor:background contrast when monitoring Cy5 only in a non-FRET ACPP.

Example 6

Figure 7B:
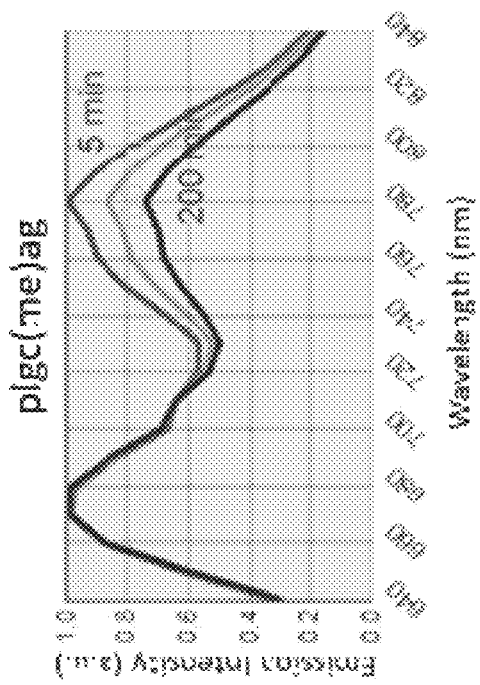
FIG. 7 provides a comparison of cleavable and uncleavable FRET-ACPP substrates used for imaging of ex vivo tumors. FRET-ACPP 2 (7A) contains the cleavable linker (SEQ ID NO:5) oPLGC(Me)AG; FRET-ACPP 3 (7B) contains a slightly cleavable linker oplgc(me)ag; and FRET-ACPP 4 (7C) contains a non-cleavable PEG6 linker.
Figure 7A:
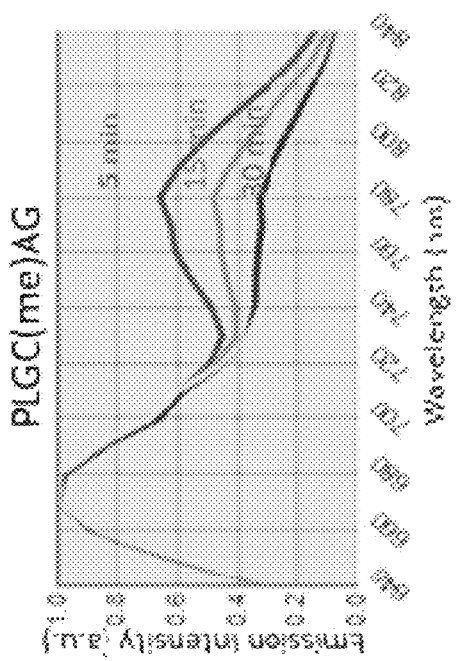
Figure 7C:
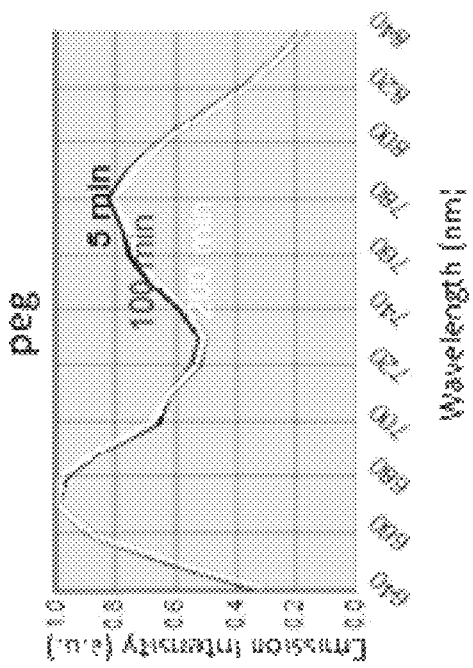

Comparison of Cleavable and Non-Cleavable FRET ACPP Substrates in Ex Vivo Tumor Imaging Careful analysis of the spectra of ACPPs injected into tumors ex vivo show that the L-amino acid linker (SEQ ID NO:5) oPLGC(me)AG of the FRET-ACPP 2 substrate is cleaved rapidly (FIG. 7a), while the D-amino acid control linker oplgc(me)ag of the FRET-ACPP 3 substrate shows much slower cleavage (FIG. 7b), but not zero either. This may explain the modest tumor contrast for Cy5 in the lower left panel of FIG. 6, as well as the slight color change between FIGS. 5c and 5d. A linker made of 6 ethyleneglycol repeats (PEG6) is completely noncleavable (FIG. 7c) and yet further reduces the tumor: background contrast in vivo.

Example 7

Multispectral Imaging of Syngenic MMTV-PyMT Mammary Tumors (Tu) in Mice Whose MMP-2 and MMP-9 are Wild-Type (+/+) or Deficient (−/−)

The comparison of the FRET-ACPP 2 and 3 substrates above shows that tumor contrast is stereospecific, implying enzymatic cleavage, but does not prove that MMP-2 and MMP-9 are the responsible enzymes. Therefore FRET-ACPP 2 substrate was injected into a different mouse model in which MMP-2 and -9 can be genetically knocked-out in the host animal, and greatly downregulated in the syngeneic mammary tumor (FIG. 8). Multispectral contrast of the tumor, over background tissues, developed rapidly (45 min post injection, right two panels) in the animal with normal MMP levels (far right) but not when MMP-2 and -9 were downregulated (middle right). This result confirms that a combination of MMP-2 and -9 activity is responsible for tumor contrast when imaged using the FRET-ACPP 2 substrate.

Example 8

In Vivo Emission Ratio Imaging of MBA-MDA 231 Tumors Using a FRET-ACPP Substrate Shown in FIG. 9 is a brightness modulated hue image obtained from determining the ratio of Cy5 to Cy7 emission intensity in an emission ratio image of a mouse containing MBA-MDA 231 tumor, after injection with the FRET-ACPP 1 substrate. Uncleaved FRET-ACPP 1 substrate displays efficient Cy5-Cy7 FRET. After cleavage of the substrate, the FRET disappears and the ratio of Cy5 to Cy7 fluorescence increases. In FIG. 9, the increased Cy5 to Cy7 ratio is indicated by pseudocoloring pixels with high ratios red, whereas pixels containing efficient FRET fluorescence, indicating the presence of high levels of uncleaved probe, are displayed as light blue. Pixels containing intermediate ratios of Cy5 to Cy7 fluorescence, indicating intermediate cleavage of the FRET-ACPP 1 probe, are colored green and yellow. Autofluorescence from gut can be differentiated by the gut spectrum or reduced by feeding the animal on a purified diet. A hotspot with unexpectedly high Cy5/Cy7 emission ratio (red arrow connecting FIGS. 9A and 9B) was verified by postmortem H&E staining to be an ectopic piece of tumor.

The performance of this FRET-ACPP 1 substrate was verified for the imaging of MDA-MBA-231 xenografts. FIG. 9a shows an emission ratio image of the mouse. Emission ratioing can be calculated almost instantaneously and is therefore more practical in real-time guided surgery, whereas multispectral imaging in systems like the Maestro is slow and contains an arbitrary threshold in the assignment of pixels to one pseudocolor or another. In addition to the intentionally implanted tumor, we also found an unexpected hot spot that showed higher contrast and lower FRET efficiency. This "hot spot" was later verified as tumor by traditional hematoxylin/eosin staining (FIG. 9b).

Example 9

Figure 10A:
FIG. 10 shows various in vivo images of mice implanted with 8119 MMTV-PyMT transgenic mammary tumor cells, using the FRET-ACPP 2 substrate. Each image was constructed using a different imaging technique, including: Maestro multispectral imaging (10A), Cy5/Cy7 emission ratio imaging, where pseudocolor hue indicates the determined emission ratio (10B), and Cy5 intensity imaging (10C).
Figure 10B:
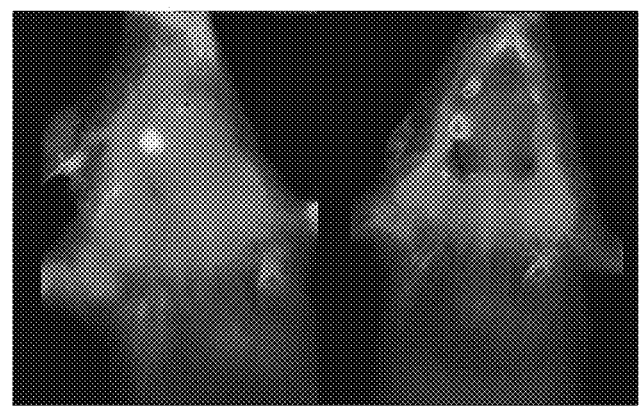
Figure 10C:
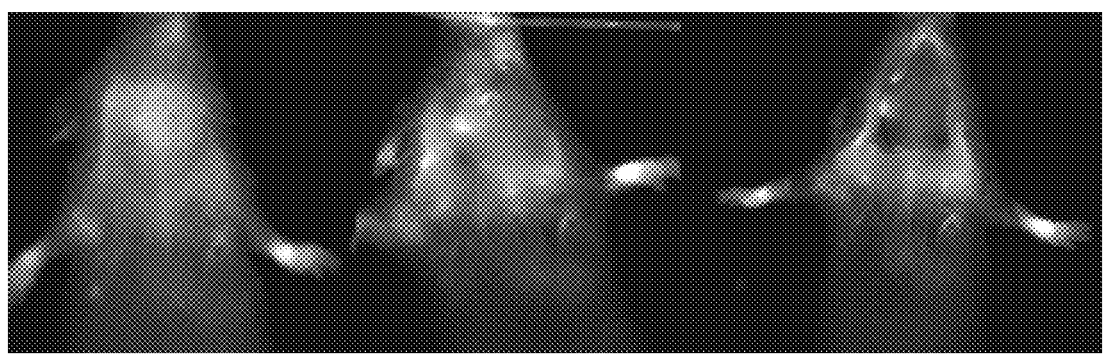

In Vivo Imaging of 8119-Metastatic Lymph Node Mouse Model Using a FRET-ACPP Substrate As shown in FIG. 10, FRET-ACPP substrates are also effective for the imaging of metastatic cancers. In this example, 8119 MMTV-PyMT transgenic mammary tumor cells were implanted into the ear of mice, from which the cells metastasized into cervical lymph nodes. Both the primary tumor in the ear and the downstream lymph node containing metastasis are readily visible 2 hours after probe administration, both by Maestro multispectral imaging (FIG. 10A) and by emission ratio imaging (FIG. 10B). These cancerous cells are much less distinct in images taken using Cy5 intensity alone (FIG. 10C), in which many other confounding factors create non-tumor regions of high intensity, while deemphasizing emissions from the primary tumor.

Example 10

Figures 11A, 11B:
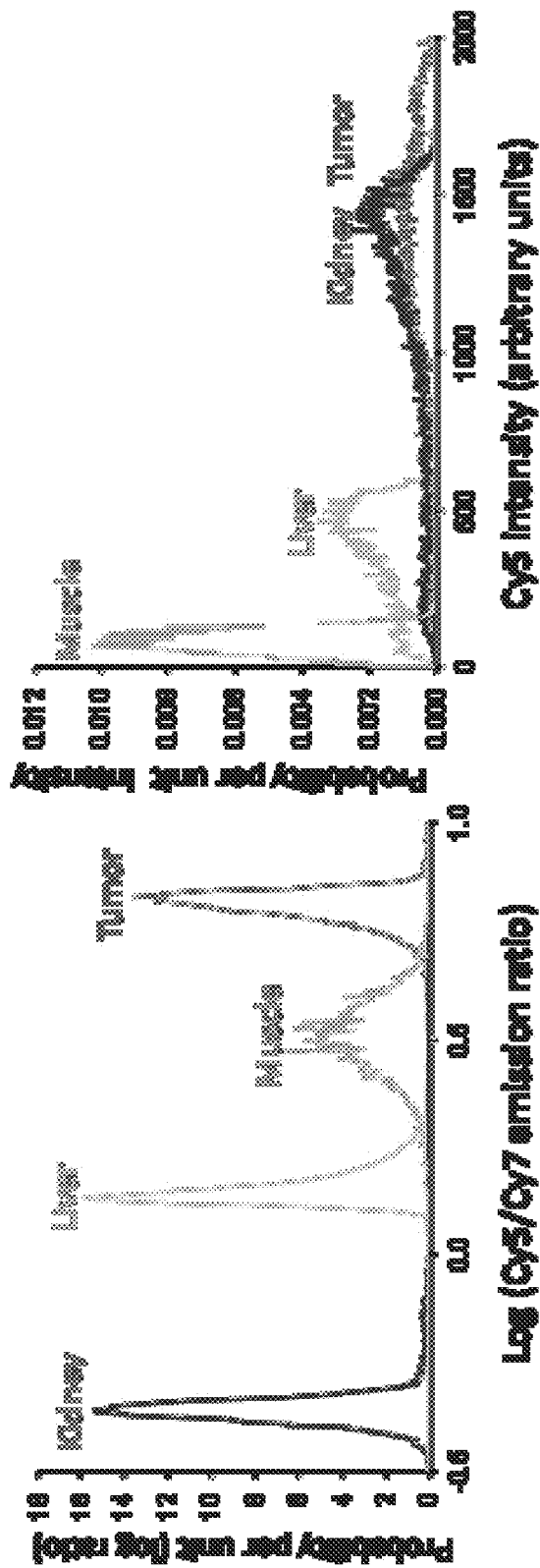
FIG. 11A shows histograms of Cy5/Cy7 emission ratios, 2 hours after injection of FRET-ACPP 2, from tissues from the mouse imaged in FIG. 6B. Ordinate: probability per unit log ratio of finding the log ratio of Cy5/Cy7 emissions as abscissa, measured from the entire dissecting tissue or organ.
FIG. 11B shows histograms of Cy5 emission intensity, 2 hours after injection of FRET-ACPP 2, from tissues from another mouse tumor model. Ordinate: probability per unit intensity of finding the intensity of Cy5 emissions as abscissa, measured from the entire dissecting tissue or organ.

Probability Analysis of Correct Identification of Tissues Using Emission Ratio Imaging and Intensity Imaging of ACPP Substrates FIG. 11 compares the statistical distribution of Cy5/Cy7 emission ratios from a FRET-ACPP (11A) with the distribution of Cy5 intensities from a standard Cy5-labeled ACPP (11B). The emission ratios (FIG. 11A) for each tissue are tightly clustered and well separated from every other tissue. Therefore it is easy to set objective criteria, e.g. Cy5/Cy7 emission ratio>4.5 (log ratio>0.65), to distinguish tumor from other tissues. The simple Cy5 intensities (FIG. 11B) show broader distributions and more overlap between tumor and normal tissues. Much of the tremendous spread of intensities is because intensities naturally decrease with decreasing thickness at the edges of tissues. This is a real problem in surgery, where it is crucial to detect the edge of the tumor. The use of emission ratios negates the effects of tissue thickness, and allows for consistent detection at the thin edge of the tissue. FIGS. 10 and 11 support the conclusion that the use of FRET-ACPPs and emission ratioing permits more robust and objective delineation of tumor boundaries than does the use of single-fluorophore ACPPs imaged using single-channel intensity.

Example 11

Figures 12A, 12B:
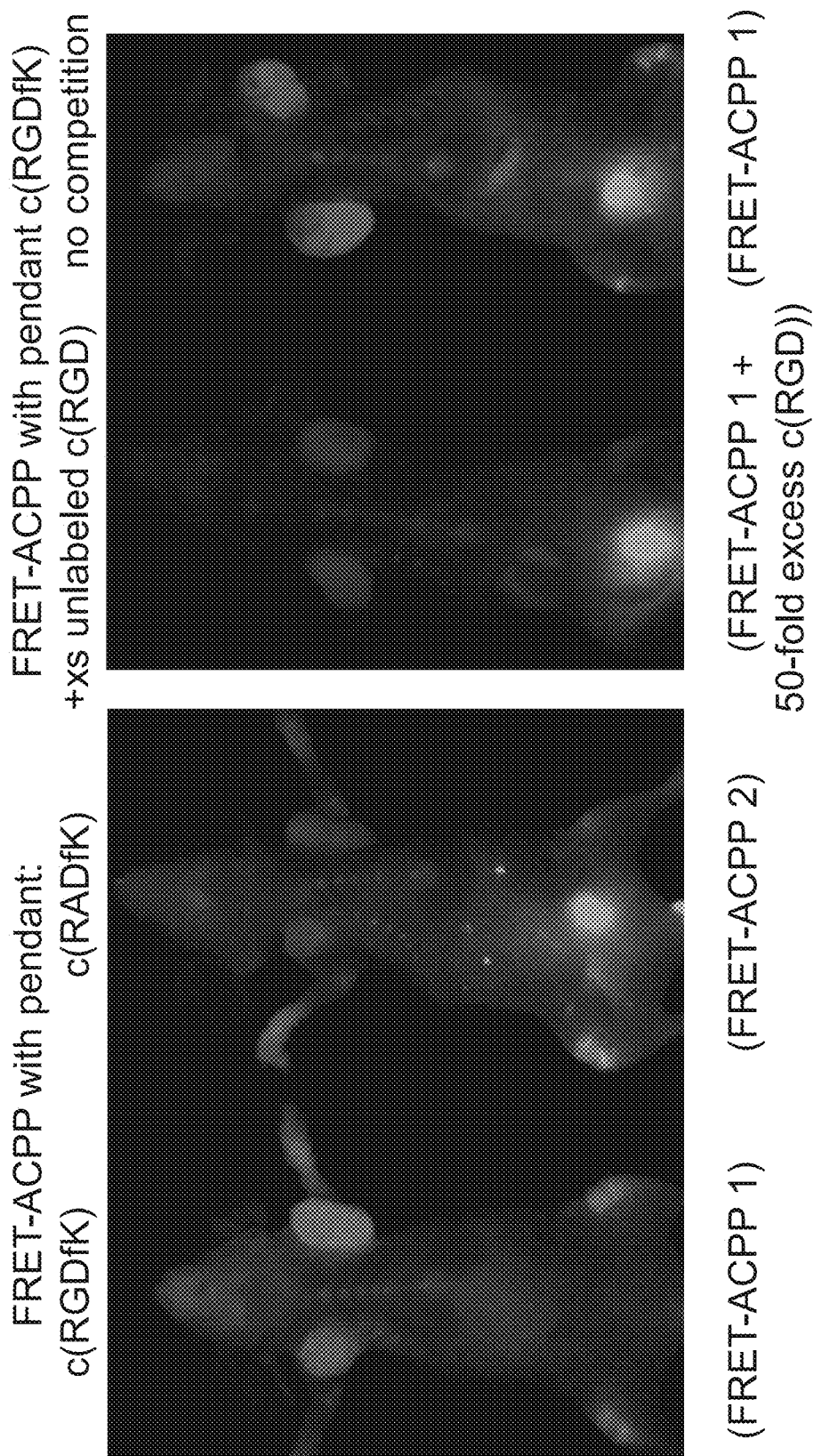
FIG. 12A compares multispectral imaging using FRET-ACPP 1 and FRET-ACPP 2 substrates in the absence of competitive targeting peptides.
FIG. 12B compares multispectral imaging using the FRET-ACPP 1 substrate in the presence and absence of unlabeled c(RGD) peptide.

In Vivo Multispectral Imaging of an HT-1080 Xenographic Mouse Model Using FRET-ACPP Substrates Containing Pendent Targeting Peptides Pendent cyclic(RGD) peptides enhances the imaging potential of FRET-ACPP substrates. FIG. 12A illustrates inclusion of a pendant c(RGDfK) ligand, as in the FRET-ACPP 1 substrate (left mouse), gives further enhancement in tumor brightness and uptake over the control FRET-ACPP 2 (right mouse), in which the pendant ligand is crippled by changing Gly to Ala to make c(RADfK). The results shown in FIG. 12B confirm that this enhancement is due to saturable binding to a receptor because the enhanced contrast is lost by co-injection of a large excess (450 nmol; 50-fold excess) unlabeled c(RGDfK) peptide, to compete with the 9 nmol of FRET-ACPP 1 (left mouse), whereas the right mouse, injected with FRET-ACPP 1 and no competing ligand, looks very similar to the image of the left mouse in FIG. 12A.

Example 12

Synthesis of RACPP Substrate Peptides

The following outlines the synthesis strategies used to construct the RACPP substrate peptides used in examples 13 to 20.

Synthesis of RACPP1

Figure 13A:
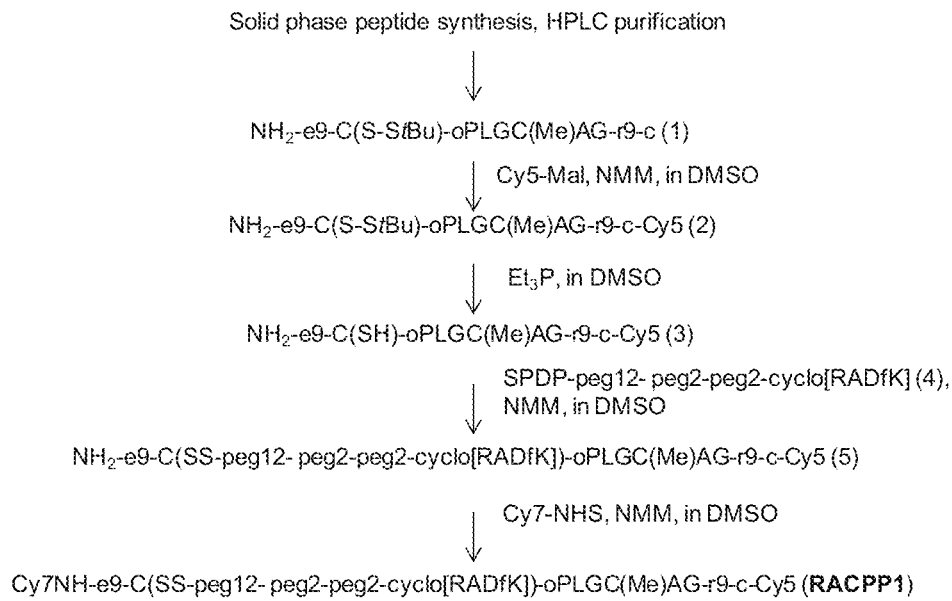
FIG. 13 diagrams the schemes used to synthesize the RACPP1 (13A), uncleavable control (13B), RACPP2 (13C), and RACPP3 (13D) peptide substrates.

According to Scheme 1 (FIG. 13A), $NH_2$-e9-C(SS-tBu)-oPLGC(Me)AG-r9-c-$CONH_2$ (1) was made using regular solid phase Fmoc peptide synthesis, where lower case letters refers to D-amino acids, o-denotes for 5-amino-3-oxopentanoyl a short hydrophilic spacer, C(Me) denotes for S-methylcysteine and the final $CONH_2$ indicates C-terminal amide. The peptide was isolated from the resin by treating it with mixtures containing 92% trifluoroacetic acid (TFA), 2% thioanisole, 2% water and 4% triisopropylsilane (TIPS) for 4 h under $N_2$ atmosphere and filtered. This filtrate was concentrated and then precipitated by addition of ice cold 50% hexanes in methyl tert-butyl ether mixture. Centrifugation was performed to isolate the precipitate that was dried under high vacuum. The peptide was dissolved in dimethyl sulfoxide (DMSO) and purified by high performance liquid chromatography (HPLC) using 5-55% acetonitrile in water and 0.05% TFA over a period of 25 min at 15 mL per min flow rate. The purified product (1) was dried using lyophilization (Mass obtained 3492.6 Da, Mass calculated 3492.8 Da).

To the purified compound 1 (10 mg) DMSO (0.8 mL, anhydrous), Cy5 maleimide (Cy5-Mal, from GE life sciences, ~2 mg), and N-methylmorpholine (NMM, 1 μL) was added under $N_2$ atmosphere and reacted for 3 h. To this reaction mixture (containing compound 2, Mass obtained 4272.0 Da, mass calculated 4271.8 Da, purification at this step is not necessary) triethyl phosphine (TEP, 25 μL) was added and kept at room temperature for another 6 h to get compound 3. Then compound (3) was precipitated by addition of ice cold 50% hexanes in methyl tert-butyl ether mixture. Centrifugation was performed to isolate the precipitate, which was dried under high vacuum and purified by HPLC using 5-55% acetonitrile gradient in water and 0.05% TFA over a period of 25 min to get $NH_2$-e9-C(SH)-oPLGC(Me)AG-r9-c(Cy5)-$CONH_2$ (3, Mass obtained 4183.2 Da, Mass calculated 4183.7 Da).

Figure 14A:
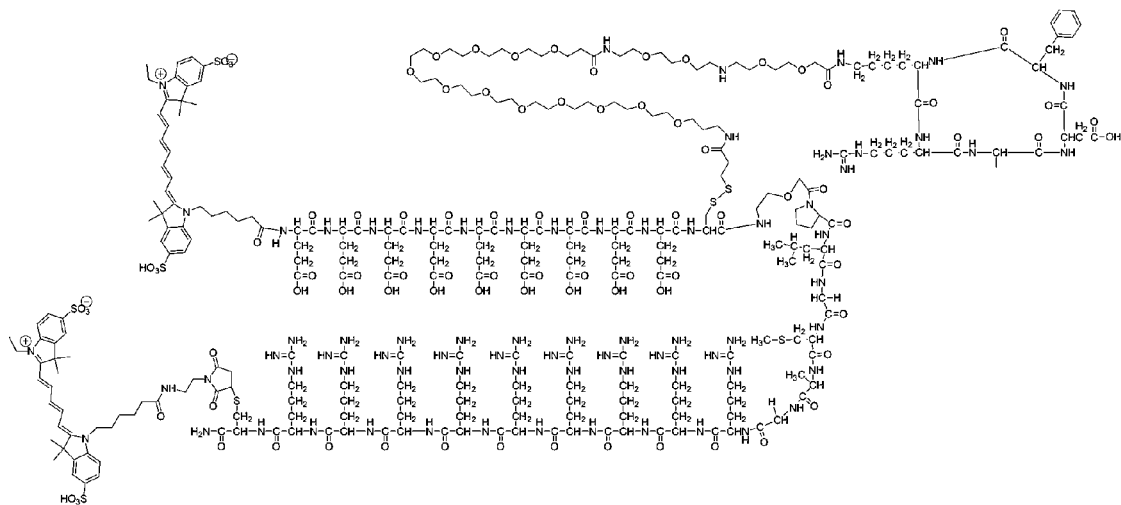
FIG. 14 illustrates the chemical structures of the RACPP1 (14A), uncleavable control (14B), RACPP2 (14C), and RACPP3 (14D) peptide substrates.
Figure 14B:
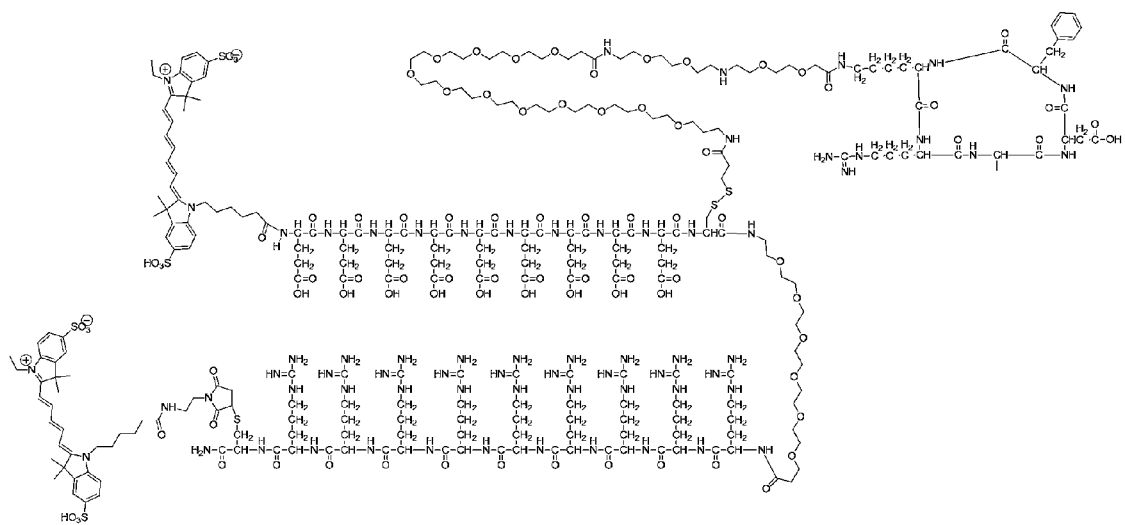
Figure 14C:
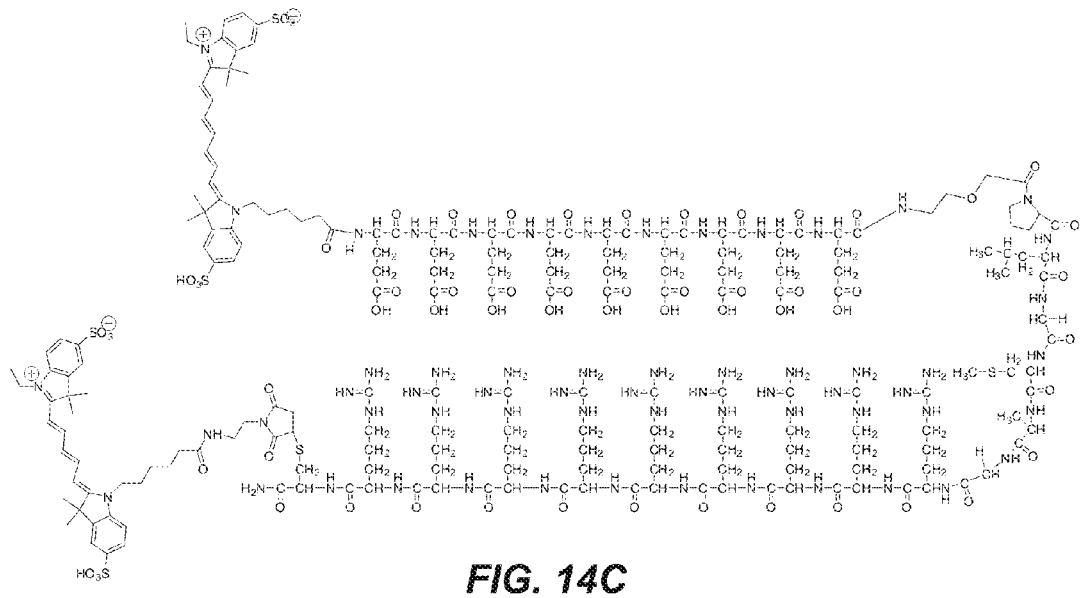
Figure 14D:
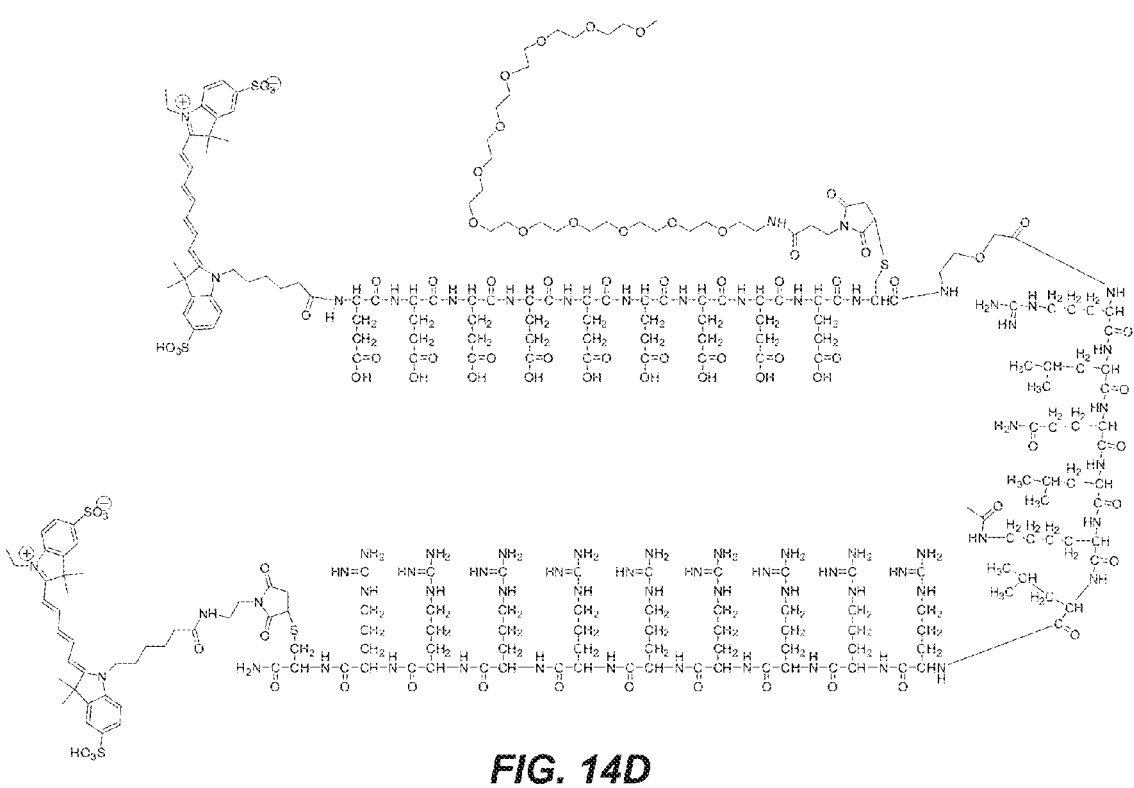

Compound 3 (5 mg), DMSO (0.4 mL, anhydrous), compound 4 (3 mg), and NMM (0.5 μL) was added to a dry reaction vessel under $N_2$ atmosphere and reacted at room temperature for 12 h. Then (note—this reaction mixture contains compound 5, Mass obtained 5777.4 Da, Mass calculated 5777.5 Da, purification at this stage is not mandatory) Cy7 NHS ester (~1.0 mg, from GE life sciences) and NMM (1 μL) was added and kept at room temperature for another 24 h. Then the product was purified by HPLC using 15-45% acetonitrile gradient in water and 0.05% TFA to get RACPP1 (Mass obtained 6442.5 Da, Mass calculated=6442.4 Da; FIG. 14A).

Figure 13B:
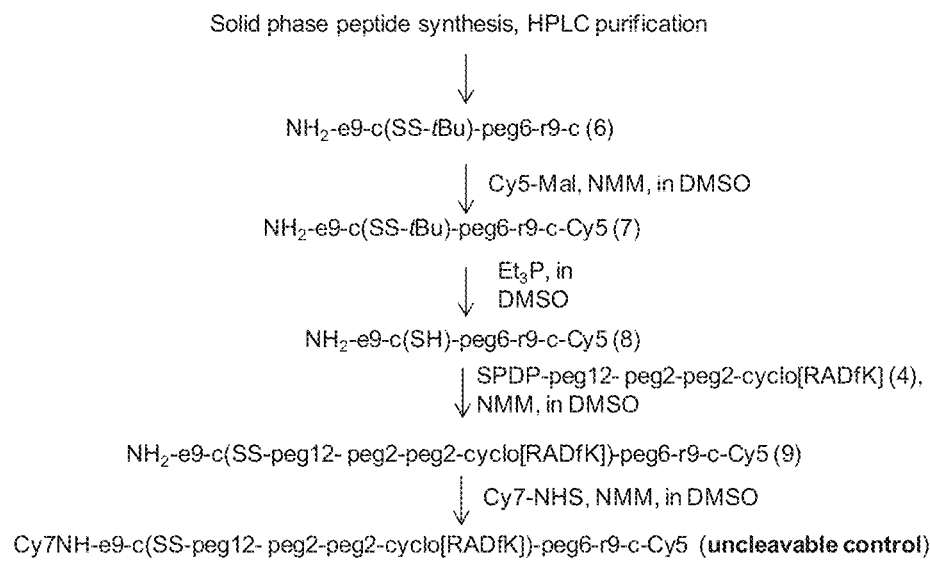

Synthesis of Uncleavable Control:

This compound was synthesized according to the Scheme 2 (FIG. 13B). Compound $NH_2$-e9-c(S-StBu)-peg6-r9-c-$CONH_2$ (6) was generated using regular solid phase Fmoc peptide synthesis, where -peg6- denotes —NH($CH_2$—$CH_2$—O)$_6$—$CH_2$—$CH_2$—CO—. The peptide was isolated by treating the resin with a mixture of 2% thioanisole, 4% TIPS, 2% water and 92% TFA for 4 h under $N_2$ atmosphere and filtered. The filtrate was concentrated and the peptide was precipitated by addition of 50% hexanes in methyl tert-butyl ether. Centrifugation was performed to isolate the precipitate, which was dried under high vacuum to remove any trace amount of solvents. The peptide was dissolved in DMSO, purified by HPLC and dried to obtain compound 6 (Mass obtained 3214.2Da, Mass calculated 3214.6 Da). To a dry reaction vessel compound 6 (12 mg), DMSO (0.7 mL), Cy5-Mal (2 mg, GE life sciences), and NMM (0.5 μL) was added under $N_2$ atmosphere and reacted for 4 h to obtain compound 7 (Mass obtained 3993.0 Da, Mass calculated 3993.5 Da). To this reaction mixture, TEP (25 μl) was added to deprotect the tert-BuSH group. After 6 h, the product was precipitated by adding a $N_2$ purged 50% hexanes in methyl tert-butyl ether mixture. The precipitated compound was isolated by centrifugation and dried under high vacuum. The compound was re-dissolved in DMSO and purified by HPLC using 15-45% acetonitrile gradient in water and 0.05% TFA over a period of 25 min (at 15 ml/min flow rate) and dried to get compound 8 (Mass obtained 3904.8 Da, Mass calculated 3905.3 Da). Compound 8 (3 mg), compound 4 (2 mg, ~2 equivalent), and NMM (0.5 µl) was added to a dry reaction vessel and reacted overnight to yield compound 9 (Mass obtained 5499.0 Da, Mass calculated 5499.2 Da). After the completion (note: purification at this step is not mandatory) of the reaction, Cy7-NHS (1 mg, GE life Sciences) and NMM (0.5 µl) was added and reacted for another 24 h to get the uncleavable control, which was purified using HPLC. LCMS indicated that the purity of the uncleavable control probe was greater than 95% (Mass obtained 6164.0 Da, Mass calculated 6164.0 Da, FIG. 14B).

Synthesis of RACPP2

Figure 13C:
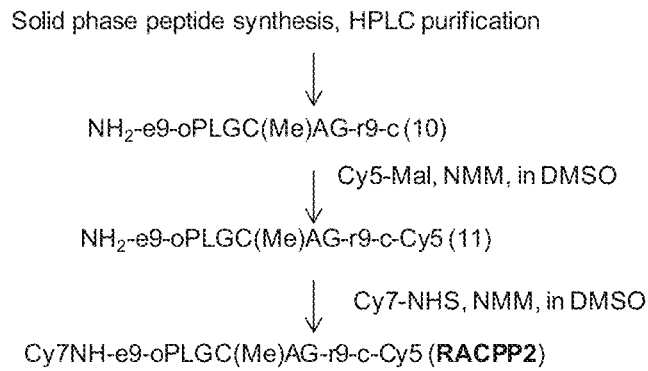

This compound was made according to the Scheme 3 (FIG. 13C). Compound $NH_2$-e9-oPLGC(Me)AG-r9c-$CONH_2$ (10) was synthesized using regular solid phase Fmoc peptide synthesis. The peptide was isolated by treating the resin with mixtures of 2% thioanisole, 4% TIPS, 2% 1,2-ethanedithiol and 92% TFA for 4 h. In order to remove the resins the reaction mixture was filtered under $N_2$ atmosphere. The filtrate was concentrated and the peptide was precipitated by addition of 50% hexanes in methyl tert-butyl ether. Centrifugation was performed to isolate the precipitate, which was dried under high vacuum. The dried compound was re-dissolved in DMSO and purified by HPLC using 5-55% acetonitrile gradient in water and 0.05% TFA over a period of 25 min at 15 ml/min flow rate, and dried using lyophilization (Mass obtained 3302.1 Da, Mass calculated 3301.6). To this dried product 10 (10 mg) DMSO (0.8 mL), Cy5-Mal (~2 mg, from GE life sciences), and NMM (1 µL) were added under $N_2$ atmosphere, reacted for 4 h, and purified by HPLC to get compound 11 (Mass obtained 4080.0 Da, Mass calculated 4080.0). Compound 11 (5 mg), Cy7 NHS ester (~1 mg, from GE life sciences), NMM (1 µL), and DMSO (0.4 mL) were added to a dry reaction vessel and reacted for 24 h at room temperature. Then the reaction mixture was subjected to HPLC purification by using 15-45% acetonitrile in water gradient over a period of 25 min at 15 mL/min flow rate to get RACPP2. The purity of the final product was greater than 95% (Mass obtained 4745.5 Da, Mass calculated 4745.4 Da, FIG. 14C).

Synthesis of RACPP3

Figure 13D:
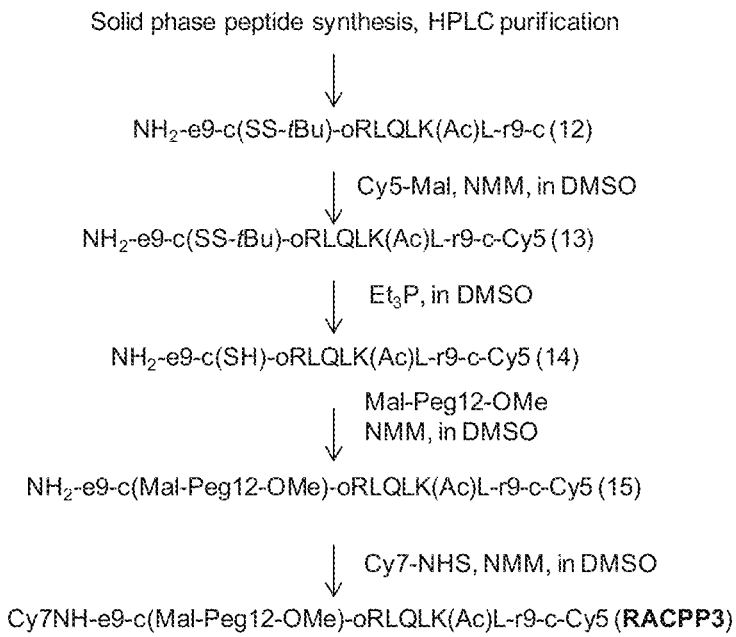

This compound was synthesized according to Scheme 4 (FIG. 13D) by following similar synthetic protocol that was followed for RACPP1 and each reaction was monitored using LCMS. The final compound was obtained with greater than 95% purity and the compound identity was verified using electrospray mass spectroscopy (Mass obtained 5840.0 Da, Mass calculated 5840.7 Da, FIG. 14D).

Synthesis of Compound 4:

To a dry reaction vial SPDP-dPEG®12-NHS ester (5 mg, Product number 10378 from Quanta Biodesign limited, molecular weight 912.08), DMSO (1 mL), Cyclo[Arg-Ala-Asp-D-Phe-Lys(PEG-PEG)] (where PEG=8-amino-3,6 dioxaoctanoic acid) (5 mg, 5.5 µmol, PCI-3954-PI from Peptide International, molecular weight 908.03), and NMM (1 µL) were added and reacted for 6 h. Then the product (4) was purified using preparative HPLC and dried using lyophilization (Mass obtained 1705.0 Da, Mass calculated 1704.9).

Example 13

Generation of Tumor and Metastases Mouse Models

For in vivo imaging, HT-1080 xenograft in athymic nude mice or LM-P or syngeneic PyMT derived 8119 cells in C57BL6 mice were used. Tumors were generated by injecting $10^6$ tumor cells in to mammary fat pads of 5-8 weeks old female mice. Animals that are reached palpable tumor size typically 5-7 mm in size selected for in vivo imaging.

For the metastatic liver model, $5 \times 10^6$ GFP positive 8119 cells in PBS were injected in to the spleen and allowed to circulate for 5 min. Vessels supplying the spleen were cauterized, the spleen removed and wound closed. The cells circulated to the liver and were allowed to grow for 12 days. Cervical lymph node invasion with metastases from primary auricular tumors were generated as previously described (Levenson, R. et al., *Anal Cell Pathol* (Amst) (2012)). Briefly, GFP-labeled 8119 or 4T1 (ATCC) mammary tumor cells were implanted (1-5 M cells) subcutaneously into the auricle of syngeneic adult wild type mice. Cervical lymph node metastases were observed in at approximately 25-50% of the animals by 2-4 weeks following subcutaneous implantation.

Example 14

In Vivo Imaging

Animals were anesthetized using mixture of ketamine (80 mg/kg) and midazolam (5 mg/kg), for syngeneic models hair near the region of interests were removed by applying NAIR hair remover. RACPPs or uncleavable control (9 nmoles) were intravenously injected and then animals were imaged using whole body mouse imager (Maestro, CRI) generally at immediate (typically at 5 min), 45 min, or 2 hr post injections, unless otherwise specified. After 2 hr post-RACPP injection, mice were euthanized by isoflurane over dose followed by cervical disllocation and then the skin was removed and imaged using whole mouse imager (Maestro, CRI). For metastatic lymph node models, animals were injected intravenously with 10 nmoles of RACPP1 or 2 nmoles of ACPPD and imaged at 2 or 24 hours following injection, respectively.

Spectral imaging was carried out by exciting Cy5 at 620 (±10) nm followed by measuring the emission from 640 to 840 nm with 10 nm step size after passing light through tunable LCD emission filter. Cy5 emission intensity images were obtained by exciting at 620 (±10) nm and collecting the emission light tuned at 670 nm. For Ratio imaging, numerator (Cy5) and denominator (Cy7) images were synthesized by integrating spectral images over a defined range at 10 nm intervals (660-720 nm for Cy5 and 760-830 for Cy7). Ratio images were calculated, processed and color encoded using custom software. The ratio value for each pixel was encoded as hue (blue to red scale) and the brightness for each pixel was based on its corresponding brightness in the original Cy5 image Animals with metastatic lymph node were also imaged using customized Olympus (MVX10) fluorescence ratio imaging system Regions of interest (ROI) were delineated using Image J and analyzed. Statistical analyses were performed using 2 tailed Student's t test. Dot density graphs were generated using Sigmaplot (12.3)

Example 15

Histology

Dissected lymph nodes were immediately embedded in Tissue Tek and frozen. Cryosections (10 µm) were obtained serially at the rate of 1 section every 100 µm through the entire lymph node. Histological analyses were performed using Hematoxylin & Eosin (H&E) staining by a pathologist blinded to experimental conditions.

Example 16

Characterization of RACPP Cleavage

RACPP1 and RACPP2 peptide substrates were subjected to MMP-9 (PF140, Calbiochem-EMD) cleavage in Tris buffer (50 mM Tris, 10 mM $CaCl_2$, 150 mM NaCl, 0.05% Brij35, pH 7.4) for 90 mM. The emission spectrum of uncleaved and MMP-9 treated RACPP1 (400 nM) in plasma was measured by exciting the Cy5 at 630 nm and collecting the emission from 640 nm to 840 nm in a cuvette spectrofluorometer (FluorLog®, Horiba Scientific).

For gel electrophoresis MMP-9 treated, untreated and urine samples were run in 10% Tricine containing polyacrylamide gel (Invitrogen) in SDS-tricine buffer for 90 min at 100 my and then imaged both Cy5 ($\lambda_{ex}$=620 (±10) nm, $\lambda_{em}$=670 nm) and Cy7 ($\lambda_{ex}$=734 (±22) nm, $\lambda_{em}$=820 nm) fluorescence using Maestro (CRI, Inc) imager (FIGS. 15A and B, respectively). Prior to loading in to the well, the MMP-9 treated sample was diluted by four fold with running buffer to avoid any saturation of Cy5 emission due to dequenching. All three components (intact uncleaved peptide, r9 and e9 fragments) are well separated and can be seen as distinct bands in the gel (FIG. 15).

Example 17

In Vivo Imaging Using RACPP

Figure 16A:
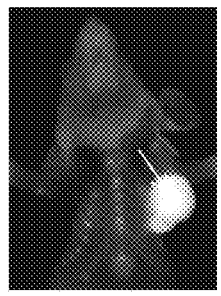
FIG. 16 (A, B) Cy5 intensity images (ex 620 nm, em 670 nm) 2 hr after IV injection of RACPP1 (A) or uncleavable control (B) into mice bearing HT-1080 xenografts, after skin removal. (C, D) Spectrally classified imaging on the same mice where pixels with only Cy5 emission are pseudocolored red (RACPP1 cleaved), and pixels with both Cy5 and Cy7 emission peaks are pseudocolored green, (RACPP1 largely intact). Cleavage of RACPP1 (C) was largely confined to the tumor (red), while the probe remained largely intact in normal tissues (green). The control uncleavable probe (D) remained uncleaved in all tissues (green). White arrows indicate tumor regions. Spectrally classified (E-H) and ratiometric (I-L) imaging of mice bearing subcutaneous LM-P syngeneic grafts following IV injection of RACPP1 (E, G, I, K) or uncleavable control (F, H, J, L). Within 5 minutes following IV injection, neither probe gave contrast between tumor and adjacent normal tissue in either spectrally classified (E, F) or ratio (I, J) images. However, tumors showed strong spectrally classified contrast 2 hr later (G, arrows) correlating with significant Cy5/Cy7 ratio change (K) compared to adjacent normal tissue whereas control probe gave neither spectrally classified (H, arrows) nor ratio tumor contrast (L).
Figure 16B:
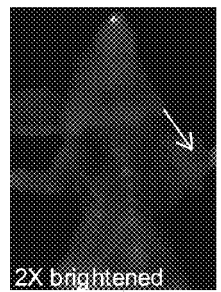
Figure 16C:
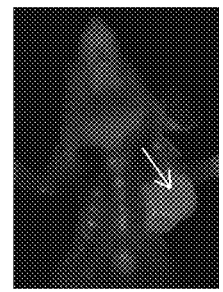
Figure 16D:
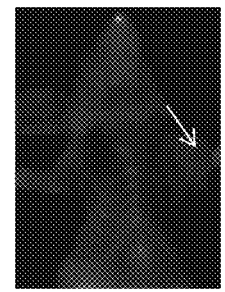
Figure 16E:
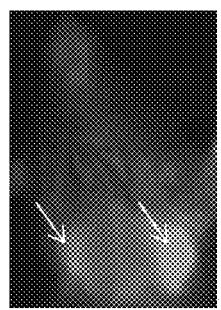
Figure 16F:
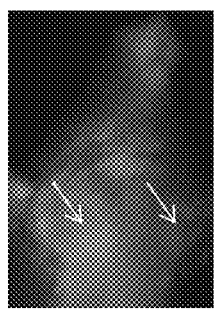
Figure 16G:
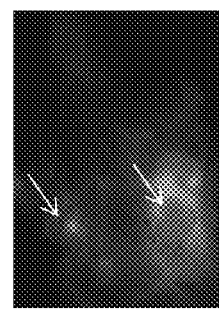
Figure 16H:
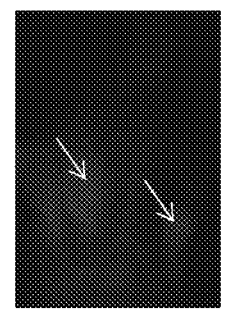
Figure 16I:
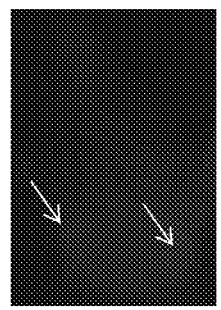
Figure 16J:
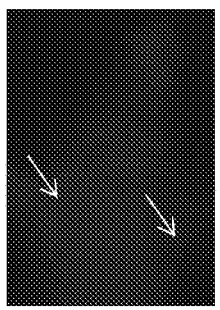
Figure 16K:
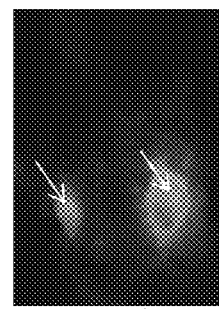
Figure 16L:
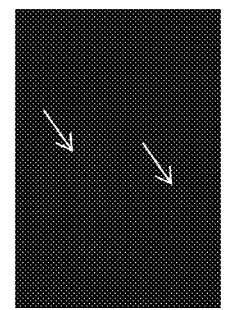

To test tumor dependent Cy5/Cy7 ratiometric change in living mice, we intravenously (IV) injected HT-1080 tumor-bearing nu/nu mice with either RACPP1 (n=4) or an uncleavable control probe (cleavage sequence replaced by a poly(ethyleneglycol) linker (peg6 of equal length, n=4). Direct Cy5 fluorescence imaging of mice injected with RACPP1 (ex 620 nm, em 670 nm, Maestro, CRI at 2 hours post injection) showed high fluorescence intensity in tumor compared to normal tissues (FIG. 16A, arrow on tumor), whereas mice injected with control peptide did not (FIG. 16B). We then performed multispectral imaging of the same mice (ex 620, em 640-840 nm), deconvoluted the spectrum at each pixel according to its dominant signature, and displayed the pseudocolor assigned to that signature (Maestro software, CRI). This spectral classification (Levenson, R. et al., *Anal Cell Pathol* (Amst) (2012), the content of which is hereby expressly incorporated herein by reference in its entirety for all purposes) visually distinguishes the tumor, in which FRET has been disrupted (FIG. 16C, arrow on tumor, red pseudocolor), from normal tissues, in which FRET remains largely intact (green pseudocolor). The same spectral classification showed that control probe remained uncleaved in both tumor and normal tissues (FIG. 16D, arrow on tumor).

Figures 17A, 17B:
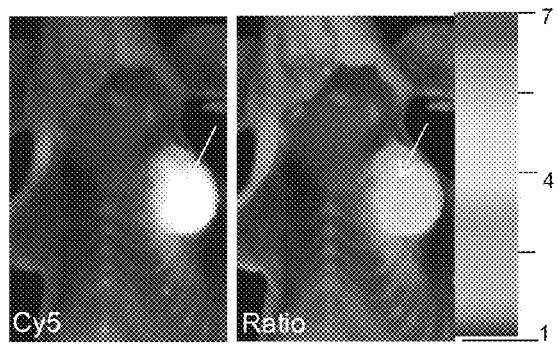
FIG. 17 shows fluorescence (A, C) and Cy5/Cy7 ratiometric (B, D) images of HT-1080 tumor bearing mice 2 hr after IV injection of RACPP1 (A, B) or uncleavable control (C, D) demonstrating tumor (arrows) contrast with the RACPP1 (A, B) but not with uncleavable control (C, D) peptide substrate. Zymogram gel (E) verifies the presence of MMP-2,-9 from three LM-P tumor samples obtained from three different mice (m1, m2 and m3) that were used in this study. Images of Cy5 (F) and Cy7 (G) fluorescence show a two-fold variability in absolute intensity between left and right LM-P tumors in the same mouse. However, the Cy5/Cy7 (H) ratios are approximately equal (5.5 vs. 5.9) between the left and right tumors.
Figures 17C, 17D:
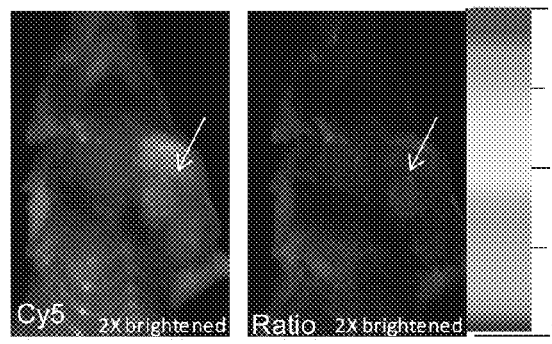

Spectral classification requires computation time and discrete pseudocolors to be assigned, so we also compared traditional displays in which increasing ratios are shown as pseudocolors smoothly varying from blue to red. When we plotted the ratio in all the obtained images, the cleavable probe gave 1.95-fold higher ratio of Cy5 to Cy7 (Cy5/Cy7) emissions in tumor than in adjacent normal tissue (5.54±0.5 vs. 2.84±0.33, n=5, $p<10^{-5}$, FIGS. 17A and B), whereas uncleavable control probe showed lower Cy5/Cy7 ratios that were identical between tumor and adjacent normal tissue (1.27±0.07 vs. 1.26±0.08, n=4, FIGS. 17C and D). The difference between RACPP1 and its uncleavable control was highly significant for both tumor Cy5/Cy7 emission ratio ($p<10^{-6}$) and ratio of Cy5/Cy7 in tumor vs. adjacent normal tissue ($p<7\times10^4$).

Figure 17E:
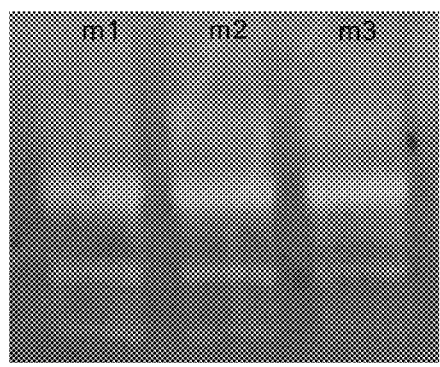
Figures 17F, 17G, 17H:
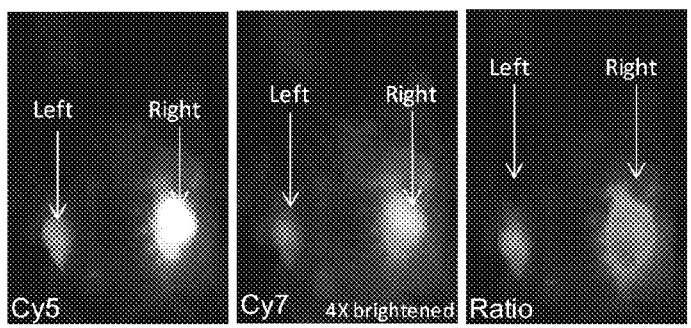

RACPP1 also did well in an immunocompetent, syngeneic model of pancreatic cancer, LM-P (Tseng, W. W. et al., *Clinical cancer research* 16, 3684-3695 (2010))_EN-REF_10, originally derived from liver metastases of transgenic pancreatic tumors. As expected, immediately (~5 min) following IV injection, there was no spectral tumor contrast (FIGS. 16E and F) nor Cy5/Cy7 ratio change (FIGS. 16I and J) with either probe. However, tumors showed strong contrast 2 hours later (FIG. 16G, arrows) correlating with significant Cy5/Cy7 ratio change (FIG. 16K, Cy5/Cy7 ratio in tumor=5.7±0.4 vs. adjacent tissue 3.0±0.2, n=3, $p=2\times10^{-8}$), whereas control probe gave neither spectrally classified tumor contrast (FIG. 16H, arrows) nor Cy5/Cy7 ratio change (FIG. 16L, ratio=1.16±0.15 in tumor vs. 1.12±0.18 in adjacent tissue, n=2 mice). Again, RACPP1 gave higher ratios than uncleavable control for tumor Cy5/Cy7 before ($p<10^{-8}$) or after normalization ($p<3\times10^{-5}$) against adjacent normal tissue. LM-P cells were verified by zymography to contain high MMP-2,-9 activity (FIG. 17E). Varying absolute tumor probe uptake or washout of nonspecific probe (compare left and right tumors in FIG. 17F) did not affect Cy5/Cy7 ratiometric change (FIG. 17H). This result emphasizes the advantage of ratiometric probes over single fluorophore or dequenching probes as tumors with differing probe distribution due to varying size or vascular disturbance may have differing absolute single wavelength intensity. However, ratioing (FIG. 17H) tends to cancel these factors, whereas protease activity has opposite effects on numerator and denominator (FIGS. 17F and G).

Example 18

Enzyme and Tumor Specific Uptake of RACPP

To test the specificity of RACPP1 for MMP-2,-9, we generated a syngeneic graft model ("KO") where MMP-2,-9 levels were genetically reduced in both the tumor (mammary cell line 8119) and the host animal (MMP-2,-9-/- mice). Within 5 min of IV RACPP1 injection, negligible tumor/normal tissue spectral or ratio contrast had developed in either KO (FIG. 18A) or wild type (WT) mice bearing the parent 8119 line with normal MMP-2,-9 activity (FIG. 18B). However, by 45 min, spectral classification revealed tumor to adjacent normal tissue contrast in WT (FIG. 18D) but not in KO (FIG. 18C). Similarly, ratiometric tumor to adjacent normal tissue contrast could be obtained only in WT (FIG. 19D, ratio=1.82±0.14, n=3 mice), not in KO (FIG. 19C, ratio=1.13±0.13, n=3, $p=4\times10^{-5}$). The uncleavable control probe (n=3 mice) did not produce spectrally classified (FIG. 19E-H) or ratiometric (FIG. 19 I-L) tumor contrast in any mice. These results document that RACPP1 is effectively selective for MMP-2,-9 in vivo.

RACPPs have also explained the claim by van Duijnhoven et al. (*J Nucl. Med.* 52, 279-286 (2011)) that ACPP targeting of tumors is due to nonspecific cleavage in the circulation together with higher blood flow to tumors. Their main evidence was that 24 hr after injection, the biodistribution of their radiolabeled ACPPs was similar to that of just the CPP portion. We generated RACPP2 (cleavable sequence=(SEQ ID NO:7) PLGC(Me)AG), an analog of RACPP1 closer in structure to those of van Duijnhoven et al. One to two hours following IV administration of RACPP2 in mice bearing HT-1080 or 8119 tumors, there was significant cleavage in the tumor but not adjacent normal tissues (FIGS. 16C, G, K and 18D, E, F), demonstrating that cleavage was localized to the tumor. However, 24 hr after injection, what little fluorescence still left in the animal showed full cleavage in both tumor and most normal tissues (FIGS. 18G and H). Analysis of RACPP2 excreted in the urine confirmed that it was largely intact at 2 hr but cleaved by 24 hr (FIGS. 15A and B), consistent with the kinetics of in vivo imaging.

Figures 20A, 20B, 20C, 20D:
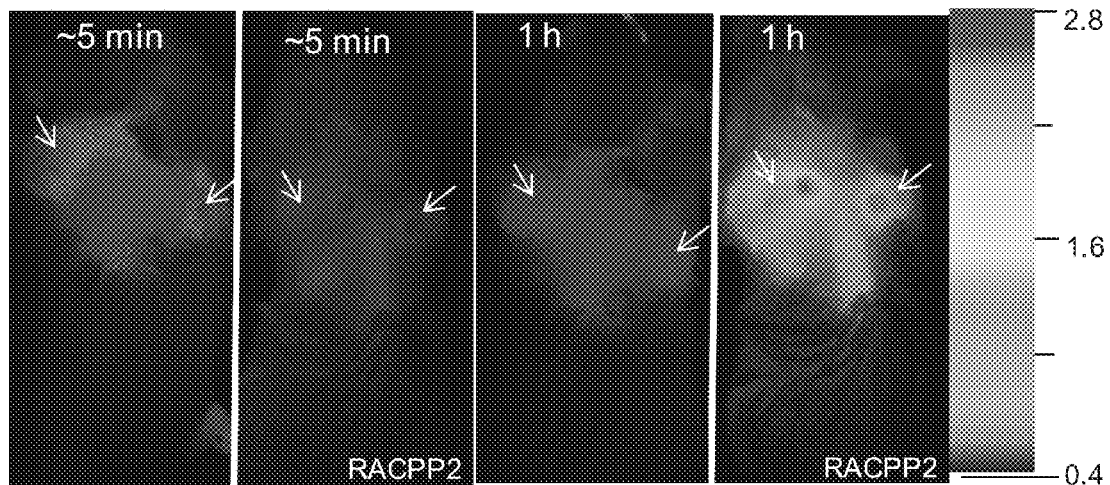
FIG. 20 shows ratio (A-D) and spectral (E-H) images obtained after injecting mixtures of RACPP2 cleaved components (Cy7e9-oPLG (e9) and C(Me)AG-r9-cCyS (r9)) (A, C, E, G) or intact RACPP2 (B, D, F, H) after 5 min (A, B, E, F) and after 1 h (C, D, G, H) following IV injection in 8119 tumor bearing mice. Spectral and ratio based tumor contrast was obtained with RACPP2 (D, H) but not with cleaved components (C, G). In spectral imaging pseudocolor red indicates cleaved probe, pseudocolor green indicates uncleaved probe, and pseudocolor cyan indicates variable fur autofluorescence. White arrows indicate tumor regions.
Figures 20E, 20F, 20G, 20H:
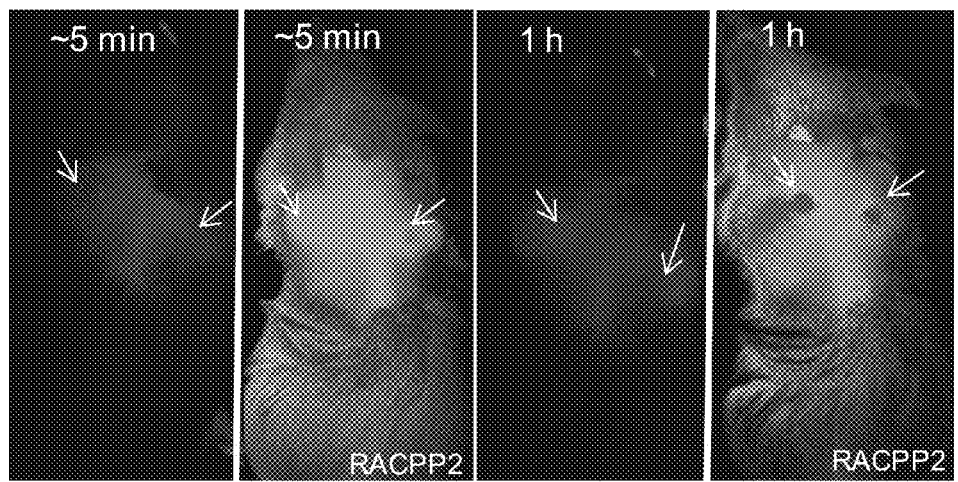

Further evidence against initial systemic cleavage came from experiments in which the two pre-cleaved halves of RACPP2 were injected. Emission ratio imaging showed complete cleavage in both tumor and normal tissues immediately (FIG. 20A, E) as well as at 1 hr post injection (FIG. 20 C, G), quite unlike injection of intact RACPP2 (FIGS. 3E, F and 20D, H). Therefore, injection of RACPP2 or its cleavage products recapitulate the ambiguous results of van Duijnhoven et al. (supra), observed only 24 hours after injection. However, the earlier images of RACPP2 substrate labeling prove that early cleavage is much faster in the tumor than in adjacent normal tissues or the general circulation.

Example 19

RACPPs Enable Detection of Metastases in the Liver

Figure 22B:
FIG. 22 shows Cy5 emission (A) and GFP emission (B) images of harvested liver from 8119 GFP positive metastatic liver metastases model obtained 2 hr following IV injection of standard non-ratiometric Cy5 labeled elastase cleavable ACPP (cleavable sequence=(SEQ ID NO:6) RLQLK(AC) L).
Figure 22A:

Previous single-fluorophore labeled ACPPs gave high uptake into normal liver, which made it unlikely that liver metastases could be accurately distinguished by standard single-wavelength imaging. We have developed a syngeneic model in which GFP-labeled 8119 mammary tumor cells colonize the liver (GFP image, FIG. 21A, E). Gratifyingly, these metastases gave high ratio contrast following RACPP1 injection compared to adjacent normal liver tissue (FIG. 21D). The co-registration between these ratio images and the GFP reference channel (FIG. 21A) is quite good, considering that the wavelengths for RACPP1 penetrate much more deeply than those for GFP. The two individual channels for Cy5 and Cy7 (FIGS. 21B and C, respectively) show many coincident non-tumor accumulations (three of which are marked by arrows) that are largely canceled with ratioing. When the MMP cleavable sequence U (SEQ ID NO:7) PLGC(Me)AG was replaced by an elastase-cleavable sequence, (SEQ ID NO:6) RLQLK(Ac)L (Whitney, M. et al., *J Biol Chem* 285, 22532-22541 (2010), the content of which is hereby expressly incorporated by reference in its entirety for all purposes), the resulting analog, RACPP3, showed spectra before and after cleavage similar to those of RACPP1. This elastase probe showed an even larger difference in ratio between metastases (ratio=5.0±0.35, average of 32 GFP positive metastases from 4 mice) and normal liver (1.49±0.1, p<10-13). Ratio images of RACPP3 (FIG. 21H) again correlated much better with GFP reference images (FIG. 21E) than the constituent Cy5 and Cy7 images did (FIGS. 21F and G). A non-ratiometric analog of RACPP3 (Whitney, M. et al., supra) lacking Cy7 failed to produce any contrast for liver metastases (FIG. 22).

Example 20

Detection of Lymph Node Metastases Using RACPP

Figure 23A:
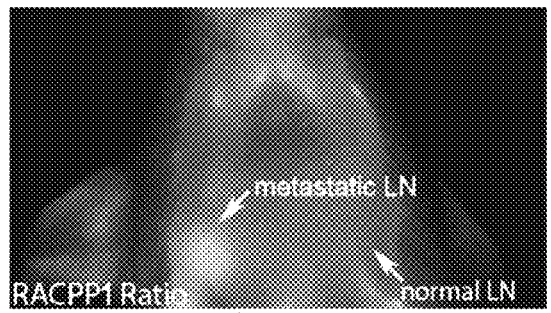
FIG. 23 shows Cy5/Cy7 ratiometric images of mice bearing auricular primary tumors (8119 line) showing increased ratio in pathologically confirmed metastatic LN but not normal LN following IV injection with RACPP1 (A). Mice injected with uncleavable control probe (B) did not show increased ratio in any lymph nodes. Fluorescent images of mice with primary auricular 8119 tumors bearing GFP with ipsilateral lymph node metastases (GFP images in C, E, G) corresponding to increased Cy5/Cy7 ratio following IV injection with RACPP1 (D, F, H). When there was only partial cancer invasion for a given lymph node (E-H, dotted lines showing LN contour), the area of increased ratio (F, H) localized with GFP signal (asterisk). All ratio images (A, B, D, F, H) were identically scaled over a range of 40 (minimum-maximum=0.2-8) to accommodate the wide dynamic range provided by RACPP1. Note that although the lymph node with only 8% cancer invasion (H) had lower Cy5/Cy7 ratio in a restricted region (asterisk) as compared to lymph nodes with more complete invasion (A, D, F). Ratiometric measurements still showed it to be higher than any adjacent normal tissue (insert scale narrowed to visually emphasize the ratiometric change, minimum-maximum=2-5). (H, insert) Ratiometric images ex vivo of dissected metastatic LN and contralateral LN.
Figure 23B:
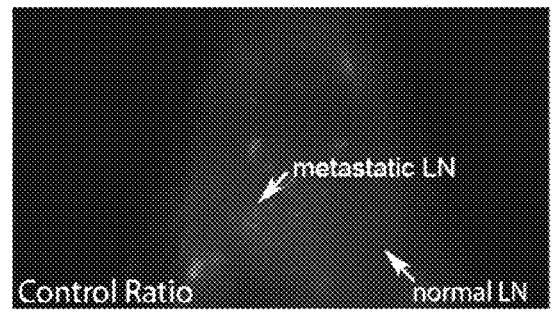
Figure 23C:
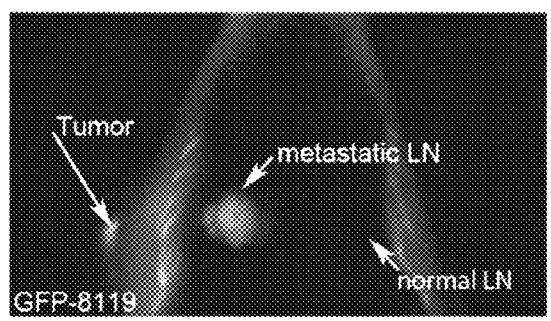
Figure 23D:
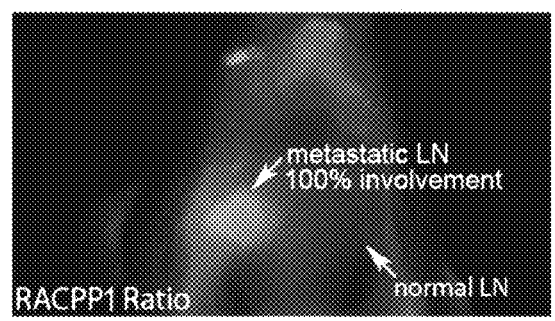
Figure 23E:
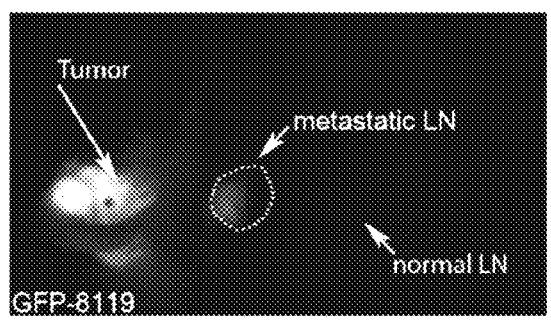
Figure 23F:
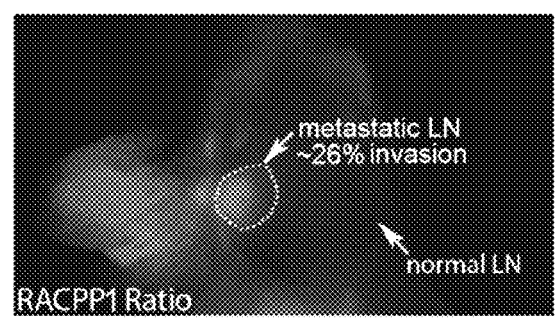
Figure 23G:
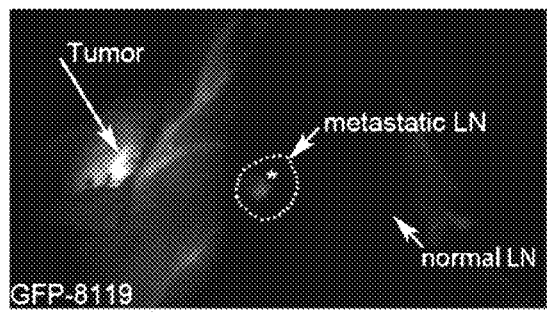
Figure 23H:
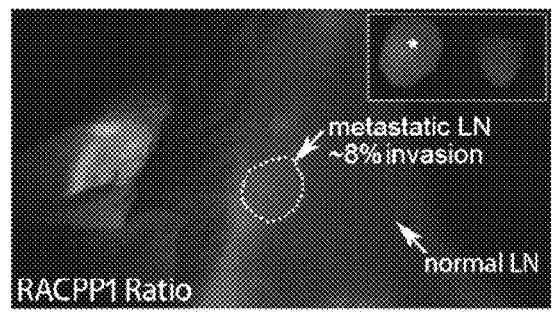

To evaluate cancer involvement of individual lymph nodes (Hoshida, T. et al., *Cancer research* 66, 8065-8075 (2006)) during surgery, mice bearing auricular primary 8119 tumors were IV injected with RACPP1. Within 1-2 hours, we found significantly increased Cy5/Cy7 ratio in lymph nodes that were involved in cancer compared with lymph nodes that were not (FIGS. 23A and 24). Mice injected with the uncleavable control RACPP showed no increased Cy5/Cy7 ratio in either metastatic or normal lymph nodes (FIGS. 23B and 24A). Quantitative analysis of Cy5/Cy7 ratio change showed that RACPP was sensitive enough to detect the presence of metastatic cancer cells even when only a fraction (8-26%) of the lymph node was invaded by cancer (FIGS. 23F, H and 24A). Prospective analysis of lymph node metastases in a second set of mice with primary 4T1 tumors injected with RACPP1 using a discrimination threshold (set at ratio of 1.2 or greater) derived from the first set of 8119 lymph node metastases gave specificity=100% (n=16/16); sensitivity=100% (n=6/6).

Our previous best intensity-only probes were ACPPs attached to Cy5-labeled dendrimers (ACPPD) (Nguyen, Q. T. et al., *Proc Natl Acad Sci USA* 107, 4317-4322 (2010); Olson, E. S. et al., *Proc Natl Acad Sci USA* 107, 4311-4316 (2010)). We compared ACPPD and RACPP1 for their sensitivity and specificity of metastasis detection in lymph nodes following IV injection of either probe into mice bearing primary auricular 8119 tumors. After recording fluorescence images from the exposed nodes in vivo, the presence or absence of metastasis was verified by independent post mortem histology. Although the ratio of ACPPD Cy5 intensities in nodes vs. adjacent normal tissue was significantly higher (p=0.02) for metastatic than non-metastatic nodes, there was considerable overlap preventing perfect discrimination at any threshold. The same measure using only Cy5 intensities for RACPP1, i.e. treating it only as a dequenching probe, gave an even more significant difference (p=0.0007) and complete separation according to node status. Even more robust (p<$10^4$) discriminations of metastatic status were obtained from Cy5/Cy7 ratios of just the node or of the node further ratioed against adjacent normal tissue (FIG. 24B).

Example 21

Synthesis of RACPP Substrate Peptides

The following outlines the synthesis strategies used to construct the RACPP substrate peptides used in examples 22 to 24. RACPPs (5, 10, 15 and 20) were prepared by Fmoc solid phase peptide synthesis and followed the same synthetic procedures that were used for elastase or MMP cleavable RACPPs (Savariar E. N., et al., Manuscript Submitted 2012). Peptides were purified using preparative HPLC and characterized using analytical HPLC combined with mass spectrometry.

All the reagents and solvents were obtained from commercial sources and used without further purification. All the reactions involving Cy5 and Cy7 were carried out under dark or shielded from light. HPLC characterizations and purifications were performed on Agilent 1100 or 1200 with reverse-phase C18 column (Phenomenex) using acetonitrile and water solvent system with 0.05% TFA as additive. Low resolution electrospray ionization (ESI) mass spectrometry was performed using Agilent HPLC connected to an Agilent LCMS trap XCT. UV absorbance was recorded on Cary 3E (Varian) or UV-2700 (Shimadzu). Fluorescence was recorded in quartz cuvettes using a spectrofluorometer (FluoroLog®, Horiba Scientific).

Synthesis of RACPP$_{DPRSFL}$:

According to the scheme outlined in FIG. 26, NH$_2$-e9-c(SS-tBu)-oDPRSFL-r9-c-CONH$_2$ (1) was prepared using conventional solid phase Fmoc peptide synthesis (Prelude, Peptide Technologies, Inc), where lower case letters refer to D-amino acids, "o" denotes 5-amino-3-oxopentanoyl (a short hydrophilic spacer), C(Me) denotes S-methylcysteine and the final CONH$_2$ indicates C-terminal amide. The peptide was isolated from the solid support by treating it with mixtures of 92% trifluoroacetic acid (TFA), 2% thioanisole, 2% water and 4% triisopropylsilane (TIPS) for 5 h under N2 atmosphere and filtered. This filtrate was concentrated and then precipitated by addition of ice cold 50% hexanes in methyl tert-butyl ether mixture. Centrifugation was performed to isolate the pellet that was dried under high vacuum. The peptide was dissolved in dimethyl sulfoxide (DMSO) and purified by high performance liquid chromatography (HPLC) using 5-55% acetonitrile in water and 0.05% TFA. The purified product (1) was dried by lyophilization (mass obtained 3695.7 Da, mass calculated 3696.1 Da).

To the purified compound 1 (20 mg) was added anhydrous DMSO (1 mL), Cy5 maleimide (Cy5-Maleimide, ~3 mg, synthesized from the NHS ester (Majumdar R. B., et al., Bioconjugate Chem. 1993, 4, 105-111) by reaction with 2-aminoethylmaleimide and N-methylmorpholine (NMM) in DMSO, followed by precipitation with ethyl acetate), NMM (1 µL) under N$_2$ atmosphere and reacted for 3 h. To this reaction mixture (contains compound 2, mass obtained 4474.8.0 Da, mass calculated 4275.0 Da, purification at this step is not necessary) triethyl phosphine (TEP, 25 µL) was added and kept at room temperature for another 6 h. Compound 3 was precipitated by addition of ice cold 50% hexanes in methyl tert-butyl ether mixture. The precipitate was collected by centrifugation, dried under high vacuum and purified by HPLC using 15-45% acetonitrile gradient in water and 0.05% to give NH$_2$-e9-c(SH)-oDPRSFL-r9-c(Cy5)-CONH$_2$ (3, mass obtained 4386.6 Da, mass calculated 4386.8 Da). To a dry reaction vessel, was added compound 3 (6 mg), DMSO (0.4 mL, anhydrous), m-dPEG12-Mal (2 mg, Quanta Biodesign, product number 10289), and NMM (0.5 µL) under N$_2$ atmosphere, reacted at room temperature for 12 h, and purified by HPLC using 7-50% acetonitrile gradient in water and 0.05% TFA to give compound 4 (mass obtained 5097.6 Da, mass calculated 5097.7 Da). To a dry reaction vessel was added compound 4 (4 mg), Cy7 NHS ester (~0.60 mg, from GE life sciences), DMSO (0.4 mL), and NMM (1 µL) and reacted at room temperature for 24 h. The product was purified by HPLC using 15-45% acetonitrile gradient in water and 0.05% TFA to give RACPP$_{DPRSFL}$ (5, mass obtained 5762.0 Da, mass calculated=5762.5 Da, FIG. 27A).

All the other RACPPs (10, 15, and 20) were synthesized according to the general scheme outlined in FIG. 26 and followed a similar synthetic protocol as that of RACPP$_{DPRSFL}$ (5). Analytical HPLC combined with mass spectrometry was used to confirm the identity of the compounds (Table 1 and Table 2).

Purity of the final compounds was assessed by analytical HPLC (data not shown) using 5-55% acetonitrile in water gradient over 25 mins at 1 ml/min flow rate.

TABLE 1

List of compounds and their molecular weights used in this study.

| Compound | Mass Obtained (Da) | Mass Calculated (Da) |
|---|---|---|
| NH$_2$-e9-c(StBu)oDPRSFL-r9-c-CONH$_2$ (1) | 3695.7 | 3696.1 |
| NH$_2$-e9-c(StBu) oDPRSFL-r9-c(Cy5)-CONH$_2$ (2) | 4474.8 | 4475.0 |
| NH$_2$-e9-c(SH) oDPRSFL-r9-c(Cy5)-CONH$_2$ (3) | 4386.6 | 4386.8 |
| NH$_2$-e9-c(S-Peg12) oDPRSFL-r9-c(Cy5)-CONH$_2$ (4) | 5097.6 | 5097.7 |
| Cy7-NH-e9-c(S-Peg12) oDPRSFL-r9-c(Cy5)-CONH$_2$ (5, RACPP$_{DPRSFL}$) | 5762.0 | 5762.5 |
| NH$_2$-e9-c(SStBu)oPPRSFL-r9-c-CONH$_2$ (6) | 3678.0 | 3678.1 |
| NH$_2$-e9-c(SStBu) oPPRSFL-r9-c(Cy5)-CONH$_2$ (7) | 4457.2 | 4457.0 |
| NH$_2$-e9-c(SH) oPPRSFL-r9-c(Cy5)-CONH$_2$ (8) | 4368.4 | 4368.9 |
| NH$_2$-e9-c(S-Peg12) oPPRSFL-r9-c(Cy5)-CONH$_2$ (9) | 5079.4 | 5079.7 |
| Cy7-NH-e9-c(S-Peg12) oPPRSFL-r9-c(Cy5)-CONH$_2$ (10, RACPP$_{PPRSFL}$) | 5744.4 | 5744.5 |
| NH$_2$-e9-c(SStBu)-peg6-r9-c-CONH$_2$ (11) | 3214.2 | 3214.6 |
| NH$_2$-e9-c(SStBu)-peg6-r9-c(Cy5)-CONH$_2$ (12) | 3993.0 | 3993.5 |
| NH$_2$-e9-c(SH)-peg6-r9-c(Cy5)-CONH$_2$ (13) | 3904.8 | 3905.3 |
| NH$_2$-e9-c(S-Peg12)-peg6-r9-c(Cy5)-CONH$_2$ (14) | 4616.4 | 4616.1 |
| Cy7-NH-e9-c(S-Peg12)-peg6-r9-c(Cy5)-CONH$_2$ (15, RACPP$_{peg6}$) | 5280.8 | 5281.0 |
| NH$_2$-e9-c(SStBu)oPLGC(Me)AG-r9-c-CONH$_2$ (16) | 3492.6 | 3492.8 |
| NH$_2$-e9-c(SStBu)oPLGC(Me)AG-r9-c(Cy5)-CONH$_2$ (17) | 4271.6 | 4271.8 |
| NH$_2$-e9-c(SH)oPLGC(Me)AG-r9-c(Cy5)-CONH$_2$ (18) | 4183.3 | 4183.7 |
| NH$_2$-e9-c(S-Peg12)oPLGC(Me)AG-r9-c(Cy5)-CONH$_2$ (19) | 4894.0 | 4894.5 |
| Cy7-NH-e9-c(S-Peg12)oPLGC(Me)AG-r9-c(Cy5)-CONH$_2$ (20, RACPP$_{PLGC(Me)AG}$) | 5559.6 | 5559.3 |

TABLE 2

Molecular weights of RACPPs obtained using high resolution mass spectrometry.

| RACPPs | Mono isotopic mass (obtained, Da) | Mono isotopic mass (calculated, Da) |
|---|---|---|
| Cy7-NH-e9-c(S-Peg12) oDPRSFL-r9-c(Cy5)-CONH$_2$ (5, RACPP$_{DPRSFL}$) | 5758.6429 | 5758.6333 |
| Cy7-NH-e9-c(S-Peg12) oPPRSFL-r9-c(Cy5)-CONH$_2$ (10, RACPP$_{PPRSFL}$) | 5740.6650 | 5740.6591 |
| Cy7-NH-e9-c(S-Peg12)-peg6-r9-c(Cy5)-CONH$_2$ (15, RACPP$_{peg6}$) | 5277.4158 | 5277.4147 |
| Cy7-NH-e9-c(S-Peg12)oPLGC(Me)AG-r9-cCy5-CONH$_2$ (20, RACPP$_{PLGC(Me)AG}$) | 5555.5104 | 5555.5097 |

Example 22

Characterization of the RACPP Peptide Substrates

The initial thrombin cleavable ACPP used the substrate sequence DPR↑SFL, which was derived from amino acids 39-44 of the thrombin receptor PAR-1, where ↑ marks the site of cleavage. The (SEQ ID NO:2) PPRSFL cleavage sequence was identified by substitution mutagenesis as a more selective thrombin substrate. The substitution of proline at the P3 position to increase specificity for thrombin over plasmin is consistent with results from previous positional scanning reports (Backes B. J., et al., Nature biotechnology 2000, 18, 187-193). Kinetic analysis was used to determine the susceptibility of (SEQ ID NO:1) DPRSFL (5)

and (SEQ ID NO:2) PPRSFL (10) RACPPs to thrombin, plasmin and factor Xa, the protease that activates prothrombin. In vitro measurements yielded $k_{cat}/K_m=1.2\times10^4$ $M^{-1}s^{-1}$ for thrombin with (SEQ ID NO:1) RACPP$_{DPRSFL}$, compared to the previously reported $k_{cat}/K_m$ of $2.1\times10^4$ $M^{-1}s^{-1}$ for the non-ratiometric (SEQ ID NO:1) DPRSFL ACPP (Olson E. S., et al., Integrative Biology: Quantitative Biosciences from Nano to Macro 2012, 4, 595-605). However, the $k_{cat}/K_m$ values for plasmin ($1.0\times10^4$ $M^{-1}s^{-1}$) and factor Xa ($6.2\times10^3$ $M^{-1}s^{-1}$) were less than 2 fold different than thrombin. In contrast, (SEQ ID NO:2) RACPP$_{PPRSFL}$(10) showed a slightly lower $k_{cat}/K_m$ ($7.3\times10^3$ $M^{-1}s^{-1}$) for thrombin but much greater selectivity over plasmin (14.3 fold lower $k_{cat}/K_m$) and factor Xa, which showed no detectable activity towards RACPP$_{PPRSFL}$.

To confirm that the spectroscopic readout was due to peptide cleavage, the RACPPs (5, 10, and 15) were incubated with enzyme and separated using SDS-polyacrylamide gel electrophoresis (FIG. 29). These gels were analyzed with multispectral imaging (ex 620, em 640-840 nm) and displayed as the ratio of Cy5 (peak~680 nm) to Cy7 (peak~780) emissions in pseudocolors from blue (ratio minimum) to red (ratio maximum) using custom designed software. This direct ratiometric imaging visually distinguished uncleaved probe in which FRET was intact (FIG. 29 blue pseudocolor), from cleaved probe in which FRET was disrupted (FIG. 29 red pseudocolor). Images confirmed that (SEQ ID NO:2) RACPP$_{PPRSFL}$ (10) and (SEQ ID NO:1) RACPP$_{DPRSFL}$ (5) are cleaved by thrombin in a time dependent manner and that (SEQ ID NO:2) RACPP$_{PPSHF}$(10) is selective for thrombin. An MMP cleavable (SEQ ID NO:7) RACPP$_{PLG(Me)AG}$ (20) was also shown as a control that was not cleaved by any of the pro-coagulation enzymes. Because SDS-polyacrylamide gel did not separate intact RACPP from Cy7-anionic fragments, we developed buffer conditions using PEHA-Acetate and agarose gels that showed distinct bands for all the three expected components (FIG. 30).

Probe Analysis Using SDS Polyacrylamide Gel Electrophoresis:

Prior to gel electrophoresis, 1 µM of each RACPP synthesized in Example 21 were cleaved in 150 mM NaCl, 20 mM Tris pH 7.5, 2 mM CaCl$_2$, 1% BSA, and 50 nM enzyme at 37° C. Purified thrombin, plasmin, factor Xa, and MMP-9 (activated) were purchased from EMD Chemicals. Samples were mixed with tricine SDS gel loading buffer and heated to 95° C. for 5 min before loading in 10-20% tricine gels for electrophoresis. Images were taken on a Maestro multispectral imager (CRI Inc.) with 620 nm excitation and collection for Cy5 (660 to 720 nm) and Cy7 (760 to 830 nm) emission, respectively. Ratiometric images were synthesized by dividing the Cy5 emission by the Cy7 emission. Pseudocolors from blue (ratio minimum) to red (ratio maximum) were assigned using custom designed software.

Probe Analysis Using PEHA-Acetate a Arose Gel Electrophoresis:

RACPP$_{LGC(Me)AG}$ and (SEQ ID NO:2) RACPP$_{PPRSFL}$ were cleaved in 150 mM NaCl, 20 mM Tris pH 7.5, and 2 mM CaCl$_2$ or 2×PBS buffer with 100 nM MMP-9 or thrombin at 37° C. respectively. Samples were mixed with PEHA (80 mM pentaethylenehexamine neutralized with acetic acid to make pH 5.6) buffer containing 15% glycerol, loaded on 4% agarose gel in 50 mM PEHA-Acetate pH 5.6, electrophoretically separated, and imaged as above.

Determination of $k_{cat}/K_m$:

Each probe was diluted in Tris cleavage buffer containing 150 mM NaCl, 20 mM Tris pH 7.5, 2 mM CaCl$_2$, and 1% BSA. Stock solutions of probe were made at to 1.2, 0.6, 0.4, and 0.3 µM. Thrombin, factor Xa were diluted to 10, 40, and 200 nM in Tris cleavage buffer. The plate reader (Safire, Tecan) was set at 37° C. in bottom read mode with manual gain setting 110 and kinetic interval of sample measurements every 30 seconds for the first 30 minutes, then every 15 minutes for 2 hours. The excitation and emission wavelengths for Cy5 were set at 630 nm and 680 nm respectively. 50 µl of each concentration of each probe was mixed with 50 µl of each enzyme stock in a black-walled clear-bottom Costar 96 well plate. After mixing, plate reader measurements were started immediately to catch the initial rate of reaction. Percent cleavage was assessed and multiplied by the starting concentration to obtain the total product concentration. The velocity of each reaction was obtained by determination of the slope of the linear portion of the curve on a scatter plot comparing product vs. time. The ratio $k_{cat}/K_m$ was obtained from the reciprocal of the slope of a Lineweaver-Burke plot. Because of concerns about aggregation and intermolecular quenching, substrate concentrations were limited to 1.2 nM, preventing reliable separation of $k_{cat}/K_m$ into numerator and denominator values. For in vivo imaging, which is also performed at submicromolar RACPP concentrations, only the ratio of $k_{cat}$ to $K_m$ matters, not their separate values.

Example 23

Detection of Thrombin Activity in Rapidly Forming Blood Clots

In order to test the specificity of the (SEQ ID NO:2) RACPP$_{PPRSFL}$ (10) peptide substrate in vivo, clot formation was monitored using a tail-clip mouse model. Ten nanomoles of probe was injected intravenously into an adult mouse and the fluorescence signal was monitored over time in clotting blood exuded from a tail wound. After probe administration, ratiometric Cy5/Cy7 imaging was performed immediately, 10, 20, and 40 minutes post injury (FIGS. 31A and B). The fluorescence ratio showed a rapid (within 10 minutes) localized increase at the wound site (arrows), which continued to rise throughout the duration of clotting (max ratio change ~4.0) (blue line). The spatial distribution of fluorescence was not diffuse, but rather showed a gradient suggestive of higher thrombin concentration in the blood closest to the wound.

(SEQ ID NO:2) RACPP$_{PPRSFL}$ (10) was also tested in blood clots from mice that had been pre-injected with the direct and selective thrombin inhibitor hirudin. Addition of hirudin inhibited the ratio increase by >90% (FIG. 31B, red line) which supports the conclusion that the signal in the developing clots is largely thrombin dependent. Not surprisingly the blood pool in the hirudin treated animals grew faster and the mice bled longer as normal coagulation was inhibited (FIG. 32). Likewise, control RACPPs that were cleavable by MMPs (SEQ ID NO:7) (RACPP$_{PLGC(Me)Ag}$, 20) or uncleavable (15), with a poly(ethyleneglycol) linker of matching length (—HN(CH$_2$CH$_2$O)$_6$CH$_2$CH$_2$CO—, "peg6") maintained low and stable Cy5/Cy7 emission ratios at the wound site over 40 minutes of clotting (FIG. 31B, green and purple lines). The addition of purified thrombin or MMP-9 to the developing blood pools from mice that had been injected with either (SEQ ID NO:2) RACPP$_{PPRSFL}$ (10) with hirudin or (SEQ ID NO:7) RACPP$_{PLGC(Me)AG}$ (20) produced spectacular local ratiometric contrast (FIG. 32). This verified the cleavability of the RACPPs for their respective enzyme in each of the negative controls.

Mice were anesthetized with ketamine/xylazine and RACPPs (10 nmol) were administered via bilateral retro-orbital injections. This study reports data from mice that have been injected with either (SEQ ID NO:2) RACPP$_{PPRSFL}$ (with or without hirudin), RACPP$_{peg6}$ (15) or (SEQ ID NO:7) RACPP$_{PLGC(Me)AG}$ (10). (SEQ ID NO:7) RACPP$_{PLGC(Me)AG}$ is closely related to RACPP-2, described in example 12, for imaging MMP-2/-9 activities in tumors and metastases, but (SEQ ID NO:7) RACPP$_{PLGC(Me)AG}$ adds a solubilizing PEG12 chain attached via a D-cys following the polyglutamate sequence.

For thrombin inhibition studies, mice were injected subcutaneously with hirudin (2000 U/mouse; n=3) 20 minutes prior to probe injection Immediately after probe injection the tail was amputated 2.5 mm from its tip and the mouse was placed in the Maestro imager. Multispectral images were acquired by exciting Cy5 at 620±10 nm and collecting the emitted light through a tunable liquid crystal filter from 640 nm to 840 nm with 10 nm step size. Cy5 and Cy7 emission images were generated by integrating from 660 to 720 nm (Cy5) and 760 to 830 nm (Cy7), respectively. Ratiometric images were synthesized by dividing the Cy5 emission by the Cy7 emission and pseudocoloring from blue (ratio minimum) to red (ratio maximum) using custom designed software. The absolute brightness in ratiometric images was encoded from corresponding Cy5 image. For image display, all images were identically scaled for the ratio from 0.2 (blue) to 4 (red). Significance was assessed using an unpaired two-tailed Student's t-test. All animal procedures were approved by UCSD's institutional animal care and use committee.

Example 24

Detection of Thrombin Activity in Atherosclerotic Plaques

The (SEQ ID NO:1) RACPP$_{DPRSFL}$ (5) peptide substrate was also used to image thrombin activity in atherosclerotic plaques present at carotid and aortic arteries in vivo. Thrombin activity was first visualized in atherosclerotic plaques located in the carotid artery, which was surgically exposed in live mice under conditions of normal blood flow (n=2). Mice were imaged under white light (FIG. 33A) followed by direct ratiometric imaging 2.5 hours after probe injection. Thrombin activity was detectable in plaques that could be seen with white light (FIG. 33A) with the most intense signal correlating to plaques localized on the carotid bifurcation (FIG. 33B).

Animals were then euthanized prior to dissection to expose the aortic arch and the lower carotid. Again white light (FIG. 33C) and ratiometric (FIG. 33D) images are shown. The aortic arch, brachiocephalic trunk and carotid arteries all showed significant plaque load by white light. Interestingly, high thrombin activity correlated to only subregions of the plaques and not necessarily to the regions with the thickest plaques. Detailed analysis to correlate thrombin activation with disease pathology (Olson E. S., et al., *Integrative Biology: Quantitative Biosciences from Nano to Macro* 2012, 4, 595-605) will be required to understand the disease significance of localized thrombin activation within plaques.

ApoE$^{-/-}$ mice (Jackson Laboratory) were in a C57/BL6 background and had been backcrossed 10 times. Mice were fed a 0.5% cholesterol diet (Harlan Laboratories) for 3-6 months (Coleman R., et al., *Acta Histochemica* 2006, 108, 415-424). Intraoperative imaging of atherosclerotic plaques was performed 2.5 hours after intravenous injection of 10 nmol of RACPP$_{DPRSFL}$. Prior to imaging, animals were anesthetized with ketamine/xylazine (100 mg/kg, 10 mg/kg) and the carotid arteries were exposed. Other structures, including the carotid bifurcation and the aortic arch, were exposed postmortem. All structures were imaged using a customized fluorescence dissecting microscope (Olympus MVX) with two cameras simultaneously sampling. Excitation was 615-645 nm while Cy5 emission was collected from 665-705 nm and Cy7 emission from 754-816 nm. The ratio of Cy5 to Cy7 emissions was calculated in real time and displayed as described above for Maestro-derived images.

All references, publications, patent applications, issued patents, accession records, databases, websites and document URLs cited herein are expressly incorporated by reference in their entirety for all purposes.

REFERENCES

Jiang, T. et al. Tumor imaging by means of proteolytic activation of cell-penetrating peptides. Proc. Natl. Acad. Sci. U.S.A 101, 17867-17872 (2004).

2 Aguilera, T. A., Olson, E. S., Timmers, M. M., Jiang, T. & Tsien, R. Y. Systemic in vivo distribution of activatable cell penetrating peptides is superior to cell penetrating peptides. Integrative Biology 1, 371-381 (2009).

Olson, E. S. et al. In vivo characterization of activatable cell penetrating peptides for targeting protease activity in cancer. Integrative Biology 1, 382-393 (2009).

4 Olson, E. S. et al. Activatable cell penetrating peptides linked to nanoparticles as dual probes for in vivo fluorescence and MR imaging of proteases. Proc Natl Acad Sci USA 107, 4311-4316 (2010).

Nguyen, Q. T. et al. Surgery with molecular fluorescence imaging using activatable cell-penetrating peptides decreases residual cancer and improves survival. Proc Natl Acad Sci USA 107, 4317-4322 (2010).

6 Whitney, M. et al. Parallel in vivo and in vitro selection using phage display identifies protease dependent tumor targeting peptides. Journal of Biological Chemistry 285, 22532-22541 (2010).

Chen, J., Liu, T. W., Lo, P. C., Wilson, B. C. & Zheng, G. "Zipper" molecular beacons: a generalized strategy to optimize the performance of activatable protease probes. Bioconjugate chemistry 20, 1836-1842 (2009). 8 Linder, K. E. et al. Synthesis, In vitro Evaluation, and In vivo Metabolism of Fluor/Quencher Compounds Containing IRDye 800CW and Black Hole Quencher-3 (BHQ-3). Bioconjugate chemistry 22, 1287-1297 (2011).

9 Ryppa, C. et al. In vitro and in vivo evaluation of doxorubicin conjugates with the divalent peptide E-[c (RGDfK)2] that targets integrin alphavbeta3. Bioconjug. Chem. 19, 1414-1422 (2008).

10 Vartak, D. G., Lee, B. S. & Gemeinhart, R. A. In vitro evaluation of functional interaction of integrin alphavbeta3 and matrix metalloprotease-2. Mol. Pharmaceutics 6, 1856-1867 (2009).

11 Zhu, L. et al. Dual-functional, receptor-targeted fluorogenic probe for in vivo imaging of extracellular protease expressions. Bioconjugate chemistry 22, 1001-1005 (2011).

What is claimed:

1. A compound comprising the structure:

PAP-CL-PCP wherein:
PAP is a polyanionic peptide comprising:
(i) a series of 5 to 9 glutamate residues, and
(ii) a fluorescence acceptor comprising a cyanine;
CL is a first linker, wherein the first linker is a peptide sequence;
PCP is a polycationic peptide comprising:
(i) a series of 5 to 9 arginine residues, and
(ii) a fluorescence donor comprising a cyanine; and
a targeting moiety attached to the polyanionic peptide via a second linker, wherein the targeting moiety is cyclic (RGD) or cyclic(RGDfK).

2. The compound of claim 1, wherein the second linker is attached to a derivatized amino acid in the polyanionic peptide.

3. The compound of claim 1, wherein the second linker comprises poly(ethyleneglycol).

4. The compound of claim 1, wherein the fluorescence donor is attached to a derivatized amino acid in the polycationic peptide.

5. The compound of claim 1, wherein the polyanionic peptide comprises five consecutive glutamate residues.

6. The compound of claim 1, wherein the polycationic peptide comprises eight consecutive arginine residues.

7. The compound of claim 2, wherein the derivatized amino acid in the polyanionic peptide is cysteine.

8. The compound of claim 4, wherein the derivatized amino acid in the polycationic peptide is cysteine.

9. The compound of claim 1, wherein the first linker comprises a peptide having an amino acid sequence selected from the group consisting of (SEQ ID NO: 5) oPLGC$_{Me}$AG, (SEQ ID NO: 7) PLGC$_{Me}$AG, (SEQ ID NO: 8) PLGLAG, (SEQ ID NO: 4) RLQLKL, (SEQ ID NO: 2) PPRSFL, and (SEQ ID NO: 1) DPRSFL.

10. The compound of claim 1, wherein the fluorescence donor is Cy5.

11. The compound of claim 1, wherein the fluorescence acceptor is Cy7.

12. The compound of claim 1, wherein the fluorescence acceptor is a non-fluorescent quencher.

13. A method of detecting a tumor, comprising:
(a) contacting a region of interest with the compound of claim 1;
(b) illuminating the region of interest on the subject with light having a first wavelength, the first wavelength excites the donor fluorophore but not the acceptor fluorophore; and
(c) detecting fluorescent emissions from the donor and acceptor fluorophore at the region of interest.

14. A method for detecting activity of a proteolytic enzyme in a subject in need thereof, comprising:
(a) administering to the subject a compound of claim 1;
(b) illuminating a region of interest on the subject with light having a first wavelength, the first wavelength excites the donor fluorophore but not the acceptor fluorophore; and
(c) detecting fluorescent emissions from the donor and acceptor fluorophores at the region of interest.

15. A method for detecting a cancerous tissue in a subject in need thereof, comprising:
(a) administering to the subject a compound of claim 1; wherein the first linker is cleavable by MMP2, MMP9, or an elastase;
(b) illuminating a region of interest on the subject with light having a first wavelength, the first wavelength excites the donor fluorophore but not the acceptor fluorophore; and
(c) detecting fluorescent emissions from the donor and acceptor fluorophores.

16. The method of claim 15, wherein the cancerous tissue is detected in real-time during a surgical procedure.

17. The method of claim 16, wherein the fluorescent emissions detected in (c) are used to determine the surgical margins for a resection of a tumor or tissue.

18. A method for detecting a blood clot in a subject, comprising:
(a) administering to the subject a compound of claim 1;
(b) illuminating a region of interest on the subject with light having a first wavelength, the first wavelength excites the donor fluorophore but not the acceptor fluorophore; and
(c) detecting fluorescent emissions from the donor and acceptor fluorophores.

19. The method of claim 18, wherein the blood clot is detected in real-time during a surgical procedure.

20. A method for detecting an atherosclerotic plaque in a subject, comprising:
(a) administering to the subject a compound claim 1;
(b) illuminating a region of interest on the subject with light having a first wavelength, the first wavelength excites the donor fluorophore but not the acceptor fluorophore; and
(c) detecting fluorescent emissions from the donor and acceptor fluorophores.

21. The method of claim 20, wherein the atherosclerotic plaque is detected in real-time during a surgical procedure.

22. The method of claim 14, further comprising:
(d) calculating a ratio of fluorescent emissions at a first wavelength near or at an emission maximum of the donor fluorophore: fluorescent emissions at a second wavelength near or at an emission maximum of the acceptor fluorophore.

23. The method of claim 22, further comprising displaying an image of the one or more regions of interest on the subject, the image being pseudocolored according to the ratio of fluorescent emissions at a first wavelength near or at an emission maximum of the donor fluorophore: fluorescent emissions at a second wavelength near or at an emission maximum of the acceptor fluorophore.

24. The method of claim 14, further comprising:
(d) deconvoluting a multispectral image of the region of interest to determine fluorescent emission contributions from the donor and acceptor fluorophores.

25. The method of claim 14, further comprising:
(d) displaying a multispectral image of the region of interest, the multispectral image comprising information on the fluorescent emissions of the donor and acceptor fluorophores.

26. The method of claim 25, wherein the multispectral image is pseudocolored according to one or more threshold values.

27. The method of claim 25, wherein the multispectral image is pseudocolored according to a continuous gradient of component contributions.

28. The method of claim 14, wherein the first linker comprises a peptide having an amino acid sequence selected from (SEQ ID NO: 5) oPLGC$_{Me}$AG, (SEQ ID NO:7) PLGC$_{Me}$AG, (SEQ ID NO: 8) PLGLAG, and (SEQ ID NO:4) RLQLKL.

29. The method of claim 18, wherein the first linker comprises a peptide having an amino acid sequence selected from (SEQ ID NO:2) PPRSFL and (SEQ ID NO: 1) DPRSFL.

* * * * *

SEQUENCE LISTING

<160> NUMBER OF SEQ ID NOS: 44

<210> SEQ ID NO 1
<211> LENGTH: 6
<212> TYPE: PRT
<213> ORGANISM: Artificial Sequence
<220> FEATURE:
<223> OTHER INFORMATION: ACPP cleavable by thrombin

<400> SEQUENCE: 1

Asp Pro Arg Ser Phe Leu
1               5

<210> SEQ ID NO 2
<211> LENGTH: 6
<212> TYPE: PRT
<213> ORGANISM: Artificial Sequence
<220> FEATURE:
<223> OTHER INFORMATION: optimized ACPP cleavable by thrombin

<400> SEQUENCE: 2

Pro Pro Arg Ser Phe Leu
1               5

<210> SEQ ID NO 3
<211> LENGTH: 6
<212> TYPE: PRT
<213> ORGANISM: Artificial Sequence
<220> FEATURE:
<223> OTHER INFORMATION: ACPP cleavable linker

<400> SEQUENCE: 3

Pro Leu Gly Cys Ala Gly
1               5

<210> SEQ ID NO 4
<211> LENGTH: 6
<212> TYPE: PRT
<213> ORGANISM: Artificial Sequence
<220> FEATURE:
<223> OTHER INFORMATION: ACPP clevable linker

<400> SEQUENCE: 4

Arg Leu Gln Leu Lys Leu
1               5

<210> SEQ ID NO 5
<211> LENGTH: 7
<212> TYPE: PRT
<213> ORGANISM: Artificial Sequence
<220> FEATURE:
<223> OTHER INFORMATION: FRET-ACPP2 linker cleavable by MMP-2/9
<220> FEATURE:
<221> NAME/KEY: MOD_RES
<222> LOCATION: (1)..(1)
<223> OTHER INFORMATION: modified by attachment to 5-amino-3-
      oxopentanoyl moiety
<220> FEATURE:
<221> NAME/KEY: MOD_RES
<222> LOCATION: (5)..(5)
<223> OTHER INFORMATION: METHYLATION

<400> SEQUENCE: 5

Xaa Pro Leu Gly Cys Ala Gly
1               5

<210> SEQ ID NO 6
<211> LENGTH: 6

```
<212> TYPE: PRT
<213> ORGANISM: Artificial Sequence
<220> FEATURE:
<223> OTHER INFORMATION: ACPP linker cleavable by elastase
<220> FEATURE:
<221> NAME/KEY: MOD_RES
<222> LOCATION: (5)..(5)
<223> OTHER INFORMATION: ACETYLATION

<400> SEQUENCE: 6

Arg Leu Gln Leu Lys Leu
1               5

<210> SEQ ID NO 7
<211> LENGTH: 6
<212> TYPE: PRT
<213> ORGANISM: Artificial Sequence
<220> FEATURE:
<223> OTHER INFORMATION: RACPP1 linker cleavable by MMP
<220> FEATURE:
<221> NAME/KEY: MOD_RES
<222> LOCATION: (4)..(4)
<223> OTHER INFORMATION: METHYLATION

<400> SEQUENCE: 7

Pro Leu Gly Cys Ala Gly
1               5

<210> SEQ ID NO 8
<211> LENGTH: 6
<212> TYPE: PRT
<213> ORGANISM: Artificial Sequence
<220> FEATURE:
<223> OTHER INFORMATION: ACPP linker cleavable by MMP-2

<400> SEQUENCE: 8

Pro Leu Gly Leu Ala Gly
1               5

<210> SEQ ID NO 9
<211> LENGTH: 6
<212> TYPE: PRT
<213> ORGANISM: Artificial Sequence
<220> FEATURE:
<223> OTHER INFORMATION: cleavable linker
<220> FEATURE:
<221> NAME/KEY: misc_feature
<222> LOCATION: (6)..(6)
<223> OTHER INFORMATION: Xaa can be any amino acid

<400> SEQUENCE: 9

Pro Leu Gly Leu Ala Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: ACPP cleavable linker

<400> SEQUENCE: 10

Glu Ser Pro Ala Tyr Tyr Thr Ala
1               5

<210> SEQ ID NO 11
<211> LENGTH: 5
<212> TYPE: PRT
<213> ORGANISM: Artificial Sequence
```

```
<220> FEATURE:
<223> OTHER INFORMATION: ACPP cleavable linker
<220> FEATURE:
<221> NAME/KEY: MOD_RES
<222> LOCATION: (5)..(5)
<223> OTHER INFORMATION: ACETYLATION

<400> SEQUENCE: 11

Arg Leu Gln Leu Lys
1               5

<210> SEQ ID NO 12
<211> LENGTH: 5
<212> TYPE: PRT
<213> ORGANISM: Artificial Sequence
<220> FEATURE:
<223> OTHER INFORMATION: ACPP linker cleavable by MMP-9
<220> FEATURE:
<221> NAME/KEY: MISC_FEATURE
<222> LOCATION: (3)..(3)
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (5)..(5)
<223> OTHER INFORMATION: Ser or Thr

<400> SEQUENCE: 12

Pro Arg Xaa Xaa Xaa
1               5

<210> SEQ ID NO 13
<211> LENGTH: 10
<212> TYPE: PRT
<213> ORGANISM: Artificial Sequence
<220> FEATURE:
<223> OTHER INFORMATION: ACPP linker cleavable by MMP-11

<400> SEQUENCE: 13

Gly Gly Ala Ala Asn Leu Val Arg Gly Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: ACPP linker cleavable by MMP-14

<400> SEQUENCE: 14

Ser Gly Arg Ile Gly Phe Leu Arg Thr Ala
1               5                   10

<210> SEQ ID NO 15
<211> LENGTH: 5
<212> TYPE: PRT
<213> ORGANISM: Artificial Sequence
<220> FEATURE:
<223> OTHER INFORMATION: ACPP linker cleavable by urokinase plasminogen
      activator (uPA)

<400> SEQUENCE: 15

Ser Gly Arg Ser Ala
1               5

<210> SEQ ID NO 16
<211> LENGTH: 4
```

```
<212> TYPE: PRT
<213> ORGANISM: Artificial Sequence
<220> FEATURE:
<223> OTHER INFORMATION: ACPP linker cleavable by a lysosomal enzyme

<400> SEQUENCE: 16

Gly Phe Leu Gly
1

<210> SEQ ID NO 17
<211> LENGTH: 4
<212> TYPE: PRT
<213> ORGANISM: Artificial Sequence
<220> FEATURE:
<223> OTHER INFORMATION: ACPP linker cleavable by a lysosomal enzyme

<400> SEQUENCE: 17

Ala Leu Ala Leu
1

<210> SEQ ID NO 18
<211> LENGTH: 6
<212> TYPE: PRT
<213> ORGANISM: Artificial Sequence
<220> FEATURE:
<223> OTHER INFORMATION: ACPP linker cleavable by cathepsin D
<220> FEATURE:
<221> NAME/KEY: MOD_RES
<222> LOCATION: (3)..(3)
<223> OTHER INFORMATION: ethylation
<220> FEATURE:
<221> NAME/KEY: misc_feature
<222> LOCATION: (4)..(4)
<223> OTHER INFORMATION: Xaa can be any amino acid

<400> SEQUENCE: 18

Pro Ile Cys Xaa Phe Phe
1               5

<210> SEQ ID NO 19
<211> LENGTH: 8
<212> TYPE: PRT
<213> ORGANISM: Artificial Sequence
<220> FEATURE:
<223> OTHER INFORMATION: ACPP linker cleavable by cathepsin K

<400> SEQUENCE: 19

Gly Gly Pro Arg Gly Leu Pro Gly
1               5

<210> SEQ ID NO 20
<211> LENGTH: 6
<212> TYPE: PRT
<213> ORGANISM: Artificial Sequence
<220> FEATURE:
<223> OTHER INFORMATION: ACPP linker cleavable by prostate-specific
      antigen

<400> SEQUENCE: 20

His Ser Ser Lys Leu Gln
1               5

<210> SEQ ID NO 21
<211> LENGTH: 10
<212> TYPE: PRT
<213> ORGANISM: Artificial Sequence
<220> FEATURE:
<223> OTHER INFORMATION: ACPP linker cleavable by herpes simplex virus
      protease
```

<400> SEQUENCE: 21

Leu Val Leu Ala Ser Ser Ser Phe Gly Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: ACPP linker cleavable by HIV protease

<400> SEQUENCE: 22

Gly Val Ser Gln Asn Tyr Pro Ile Val Gly
1               5                   10

<210> SEQ ID NO 23
<211> LENGTH: 10
<212> TYPE: PRT
<213> ORGANISM: Artificial Sequence
<220> FEATURE:
<223> OTHER INFORMATION: ACPP linker cleavable by cytomegalovirus
      protease

<400> SEQUENCE: 23

Gly Val Val Gln Ala Ser Cys Arg Leu Ala
1               5                   10

<210> SEQ ID NO 24
<211> LENGTH: 4
<212> TYPE: PRT
<213> ORGANISM: Artificial Sequence
<220> FEATURE:
<223> OTHER INFORMATION: ACPP linker cleavable by caspase-3

<400> SEQUENCE: 24

Asp Glu Val Asp
1

<210> SEQ ID NO 25
<211> LENGTH: 6
<212> TYPE: PRT
<213> ORGANISM: Artificial Sequence
<220> FEATURE:
<223> OTHER INFORMATION: ACPP linker cleavable by interleukin 1-beta
      converting enzyme

<400> SEQUENCE: 25

Gly Trp Glu His Asp Gly
1               5

<210> SEQ ID NO 26
<211> LENGTH: 9
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (4)..(4)
<223> OTHER INFORMATION: aminocaproic acid linker

<400> SEQUENCE: 26

Glu Asp Ala Xaa Arg Arg Arg Arg Arg
1               5

<210> SEQ ID NO 27

-continued

```
<211> LENGTH: 14
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (8)..(8)
<223> OTHER INFORMATION: aminocaproic acid linker

<400> SEQUENCE: 27

Glu Asp Asp Asp Asp Lys Ala Xaa Arg Arg Arg Arg Arg Arg
1               5                   10

<210> SEQ ID NO 28
<211> LENGTH: 21
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (12)..(12)
<223> OTHER INFORMATION: aminocaproic acid linker

<400> SEQUENCE: 28

Glu Glu Glu Asp Asp Asp Glu Glu Glu Asp Ala Xaa Arg Arg Arg Arg
1               5                   10                  15

Arg Arg Arg Arg Arg
            20

<210> SEQ ID NO 29
<211> LENGTH: 17
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (8)..(8)
<223> OTHER INFORMATION: aminocaproic acid linker

<400> SEQUENCE: 29

Glu Asp Asp Asp Asp Lys Ala Xaa Arg Arg Arg Arg Arg Arg Arg Arg
1               5                   10                  15

Arg

<210> SEQ ID NO 30
<211> LENGTH: 19
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (10)..(10)
<223> OTHER INFORMATION: aminocaproic acid linker

<400> SEQUENCE: 30

Arg Arg Arg Arg Arg Arg Arg Arg Arg Xaa Glu Glu Glu Glu Glu Glu
1               5                   10                  15

Glu Glu Glu

<210> SEQ ID NO 31
<211> LENGTH: 14
<212> TYPE: PRT
<213> ORGANISM: Artificial Sequence
<220> FEATURE:
```

```
<223> OTHER INFORMATION: ACPP core imaging substrate (A-X2-B)
<220> FEATURE:
<221> NAME/KEY: MOD_RES
<222> LOCATION: (5)..(5)
<223> OTHER INFORMATION: aminocaproic acid linker

<400> SEQUENCE: 31

Glu Glu Glu Glu Xaa Arg Arg Arg Arg Arg Arg Arg Arg
1               5                   10

<210> SEQ ID NO 32
<211> LENGTH: 21
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (12)..(12)
<223> OTHER INFORMATION: aminocaproic acid linker

<400> SEQUENCE: 32

Glu Glu Glu Glu Glu Asp Asp Asp Asp Lys Ala Xaa Arg Arg Arg
1               5                   10                  15

Arg Arg Arg Arg Arg
            20

<210> SEQ ID NO 33
<211> LENGTH: 17
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (8)..(8)
<223> OTHER INFORMATION: aminocaproic acid linker

<400> SEQUENCE: 33

Glu Asp Asp Asp Asp Lys Ala Xaa Arg Arg Arg Arg Arg Arg Arg
1               5                   10                  15

Arg

<210> SEQ ID NO 34
<211> LENGTH: 20
<212> TYPE: PRT
<213> ORGANISM: Artificial Sequence
<220> FEATURE:
<223> OTHER INFORMATION: ACPP core imaging substrate (A-X2-B)

<400> SEQUENCE: 34

Glu Glu Glu Glu Glu Asp Asp Asp Asp Lys Ala Arg Arg Arg Arg
1               5                   10                  15

Arg Arg Arg Arg
            20

<210> SEQ ID NO 35
<211> LENGTH: 17
<212> TYPE: PRT
<213> ORGANISM: Artificial Sequence
<220> FEATURE:
<223> OTHER INFORMATION: ACPP core imaging substrate (A-X2-B)

<400> SEQUENCE: 35

Asp Asp Asp Asp Asp Asp Lys Ala Arg Arg Arg Arg Arg Arg Arg
1               5                   10                  15
```

Arg

```
<210> SEQ ID NO 36
<211> LENGTH: 21
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (10)..(10)
<223> OTHER INFORMATION: aminocaproic acid linker
<220> FEATURE:
<221> NAME/KEY: MOD_RES
<222> LOCATION: (13)..(13)
<223> OTHER INFORMATION: aminocaproic acid linker
<220> FEATURE:
<221> NAME/KEY: MOD_RES
<222> LOCATION: (16)..(16)
<223> OTHER INFORMATION: aminocaproic acid linker
<220> FEATURE:
<221> NAME/KEY: MOD_RES
<222> LOCATION: (19)..(19)
<223> OTHER INFORMATION: aminocaproic acid linker

<400> SEQUENCE: 36

Glu Glu Asp Asp Asp Asp Lys Ala Arg Xaa Arg Arg Xaa Arg Arg Xaa
1               5                   10                  15

Arg Arg Xaa Arg Arg
            20

<210> SEQ ID NO 37
<211> LENGTH: 9
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (4)..(4)
<223> OTHER INFORMATION: aminocaproic acid linker

<400> SEQUENCE: 37

Glu Asp Ala Xaa Arg Arg Arg Arg Arg
1               5

<210> SEQ ID NO 38
<211> LENGTH: 14
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (8)..(8)
<223> OTHER INFORMATION: aminocaproic acid linker

<400> SEQUENCE: 38

Glu Asp Asp Asp Asp Lys Ala Xaa Arg Arg Arg Arg Arg Arg
1               5                   10

<210> SEQ ID NO 39
<211> LENGTH: 21
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: MOD_RES
<222> LOCATION: (12)..(12)
<223> OTHER INFORMATION: aminocaproic acid linker
```

```
<400> SEQUENCE: 39

Glu Glu Glu Asp Asp Asp Glu Glu Asp Ala Xaa Arg Arg Arg
1               5                   10                  15

Arg Arg Arg Arg Arg
                20

<210> SEQ ID NO 40
<211> LENGTH: 21
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: misc_feature
<222> LOCATION: (12)..(12)
<223> OTHER INFORMATION: Xaa can be any amino acid

<400> SEQUENCE: 40

Glu Glu Glu Glu Glu Asp Asp Asp Asp Lys Ala Xaa Arg Arg Arg
1               5                   10                  15

Arg Arg Arg Arg Arg
                20

<210> SEQ ID NO 41
<211> LENGTH: 20
<212> TYPE: PRT
<213> ORGANISM: Artificial Sequence
<220> FEATURE:
<223> OTHER INFORMATION: ACPP core imaging substrate (A-X2-B)

<400> SEQUENCE: 41

Glu Glu Glu Glu Glu Asp Asp Asp Asp Lys Ala Arg Arg Arg Arg
1               5                   10                  15

Arg Arg Arg Arg
                20

<210> SEQ ID NO 42
<211> LENGTH: 17
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: misc_feature
<222> LOCATION: (8)..(8)
<223> OTHER INFORMATION: Xaa can be any amino acid

<400> SEQUENCE: 42

Glu Asp Asp Asp Asp Lys Ala Xaa Arg Arg Arg Arg Arg Arg Arg
1               5                   10                  15

Arg

<210> SEQ ID NO 43
<211> LENGTH: 21
<212> TYPE: PRT
<213> ORGANISM: Artificial Sequence
<220> FEATURE:
<223> OTHER INFORMATION: ACPP core imaging substrate (A-X2-B)
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
<222> LOCATION: (13)..(13)
<223> OTHER INFORMATION: Xaa can be any amino acid
```

```
<220> FEATURE:
<221> NAME/KEY: misc_feature
<222> LOCATION: (16)..(16)
<223> OTHER INFORMATION: Xaa can be any amino acid
<220> FEATURE:
<221> NAME/KEY: misc_feature
<222> LOCATION: (19)..(19)
<223> OTHER INFORMATION: Xaa can be any amino acid

<400> SEQUENCE: 43

Glu Glu Asp Asp Asp Asp Lys Ala Arg Xaa Arg Arg Xaa Arg Arg Xaa
1               5                   10                  15

Arg Arg Xaa Arg Arg
            20

<210> SEQ ID NO 44
<211> LENGTH: 17
<212> TYPE: PRT
<213> ORGANISM: Artificial Sequence
<220> FEATURE:
<223> OTHER INFORMATION: ACPP core imaging substrate (A-X2-B)

<400> SEQUENCE: 44

Asp Asp Asp Asp Asp Asp Lys Ala Arg Arg Arg Arg Arg Arg Arg Arg
1               5                   10                  15

Arg
```